United States Patent
Nam et al.

(10) Patent No.: US 9,523,079 B2
(45) Date of Patent: *Dec. 20, 2016

(54) CARDIAC REPAIR BY REPROGRAMMING OF CARDIAC FIBROBLASTS INTO CARDIOMYOCYTES

(71) Applicant: The Board of Regents of the University of Texas System, Austin, TX (US)

(72) Inventors: Young-Jae Nam, Nashville, TN (US); Kunhua Song, Aurora, CO (US); Eric N. Olson, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/697,955

(22) Filed: Apr. 28, 2015

(65) Prior Publication Data

US 2015/0307847 A1    Oct. 29, 2015

Related U.S. Application Data

(63) Continuation of application No. 13/402,609, filed on Feb. 22, 2012, now Pat. No. 9,017,661.

(60) Provisional application No. 61/445,390, filed on Feb. 22, 2011.

(51) Int. Cl.
| | |
|---|---|
| A61K 48/00 | (2006.01) |
| C12N 5/071 | (2010.01) |
| A61P 9/00 | (2006.01) |
| C12N 5/077 | (2010.01) |
| C07K 14/47 | (2006.01) |
| A61K 31/7105 | (2006.01) |
| A61K 38/17 | (2006.01) |
| A61K 45/06 | (2006.01) |
| A61K 38/00 | (2006.01) |

(52) U.S. Cl.
CPC ......... *C12N 5/0657* (2013.01); *A61K 31/7105* (2013.01); *A61K 38/17* (2013.01); *A61K 45/06* (2013.01); *C07K 14/4702* (2013.01); *A61K 38/00* (2013.01); *C12N 2501/40* (2013.01); *C12N 2770/00043* (2013.01)

(58) Field of Classification Search
None
See application file for complete search history.

(56) References Cited

U.S. PATENT DOCUMENTS

| | | |
|---|---|---|
| 2008/0279835 A1 | 11/2008 | Henning et al. |
| 2013/0216503 A1* | 8/2013 | Srivastava ........... C12N 5/0657 424/93.7 |

FOREIGN PATENT DOCUMENTS

| | | |
|---|---|---|
| WO | WO 99/62940 | 12/1999 |
| WO | WO 02/02148 | 1/2002 |
| WO | WO 2008/088882 | 7/2008 |
| WO | WO 2009/151907 | 12/2009 |
| WO | WO 2010/075575 | 7/2010 |
| WO | WO 2011/139688 | 11/2011 |
| WO | WO 2011/163531 | 12/2011 |

OTHER PUBLICATIONS

Alexander and Bruneau, "Lessons for cardiac regeneration and repair through development," *Trends Mol. Med.*, 16:426-34, 2010.
Armstrong et al., "Treatment of acute ST-elevation myocardial infarction," *Cardiovascular Medicine*, 963-977, 2007.
Hasson, et al., "Mutations in human TBX5 [corrected] cause limb and cardiac malformation in Holt-Oram syndrome," *Nat. Genet.*, 15:30-5, 1997.
Dai, et al., "The transcription factors GATA4 and dHAND physically interact to synergistically activate cardiac gene expression through a p300-dependent mechanism," *J. Biol. Chem.*, 277:24390-8, 2002.
Ghosh, et al., "Physical interaction between TBX5 and MEF2C is required for early heart development," *Mol. Cell. Biol.*, 29:2205-18, 2009.
Ieda, et al., "Direct reprogramming of fibroblasts into functional cardiomyocytes by defined factors," *Cell*, 142:375-86, 2010.
Kohei, et al., "Direct conversion of cardiac fibroblasts into cardiomyocyte-like cells in vivo," *Circulation*, vol. 124, 2011.
Li, et al., "In vivo reprogramming of murine cardiac fibroblasts into induced cardiomyocytes," *Circulation*, vol. 124, 2011.
Loffredo, et al., "Bone marrow-derived cell therapy stimulates endogenous cardiomyocyte progenitors and promotes cardiac repair," *Cell Stem Cell*, 8:389-98, 2011.
Maitra, et al., "Interaction of Gata4 and Gata6 with Tbx5 is critical for normal cardiac development," *Dev. Biol.*, 326:368-77, 2009.
McDermott, et al., "hMEF2C gene encodes skeletal muscle- and brain-specific transcription factors," *Mol. Cell. Biol.*, 13:2564-77, 1993.
Melo et al., "Gene and cell-based therapies for heart disease," *FASEB*, 18:648-663, 2004.
Molkentin, et al., "Mutational analysis of the DNA binding, dimerization, and transcriptional activation domains of MEF2C," *Mol. Cell. Biol.*, 16:2627-36, 1996.
Office Action issued in U.S. Appl. No. 13/402,609, mailed Feb. 4, 2014.
Office Action issued in U.S. Appl. No. 13/402,609, mailed Jun. 11, 2014.
Office Action issued in U.S. Appl. No. 13/402,609, mailed Mar. 27, 2013.
Olson, "Gene regulatory networks in the evolution and development of the heart," *Science*, 313:1922-7, 2006.
Parmacek, "Myocardin-related transcription factors: critical coactivators regulating cardiovascular development and adaptation," *Circ Res.*, 100:633-644, 2007.

(Continued)

*Primary Examiner* — Scott Long
*Assistant Examiner* — Arthur S Leonard
(74) *Attorney, Agent, or Firm* — Parker Highlander PLLC

(57) ABSTRACT

The present invention involves the use of transcription factors including Tbx5, Mef2C, Hand2, myocardin and Gata4 to reprogram cardiac fibroblasts into cardiomyocytes, both in vitro and in vivo. Such methods find particular use in the treatment of patients post-myocardial infarction to prevent or limit scarring and to promote myocardial repair.

15 Claims, 62 Drawing Sheets

(56) References Cited

OTHER PUBLICATIONS

PCT International Preliminary Report on Patentability issued in International Application No. PCT/US2012/026113, mailed Sep. 6, 2013.

PCT International Search Report and Written Opinion issued in International Application No. PCT/US2012/026113, mailed Jun. 4, 2012.

Russell, et al., "Molecular cloning of the human HAND2 gene," *Biochim. Biophys. Acta.*, 1443:393-9, 1998.

Song et al., "Heart repair by reprogramming non-myocytes with cardiac transcription factors," *Nature*, 485:599-604, 2012.

Terrett, et al., "Holt-Oram syndrome is a genetically heterogeneous disease with one locus mapping to human chromosome 12q," *Nat. Genet.*, 6:401-4, 1994.

Thygesesn et al., "The definitions of acute coronary syndrome, myocardial infarction, and unstable angina," *Curr Cardiol Rep.*, 3(4):268-272, 2001.

White, et al., "Assignment of the transcription factor GATA4 gene to human chromosome 8 and mouse chromosome 14: Gata4 is a candidate gene for Ds (disorganization)," *Genomics*, 27:20-6, 1995.

Yao et al., "Repeated autologous bone marrow mononuclear cell therapy in patients with large myocardial infarction," *European Journal of Heart Failure*, 11:691-698, 2009.

Zang, et al., "Cooperative interaction between the basic helix-loop-helix transcription factor dHAND and myocyte enhancer factor 2C regulates myocardial gene expression," *J. Biol. Chem.*, 279:54258-63, 2004.

Office Action issued in Japanese Application No. 2013-555521, mailed Jan. 28, 2016, and English language translation thereof.

\* cited by examiner

| Gene Ontology Category | P-Value |
|---|---|
| muscle contraction | 2.56E-16 |
| mesoderm development | 6.56E-16 |
| muscle organ development | 3.84E-12 |
| heart development | 6.78E-05 |

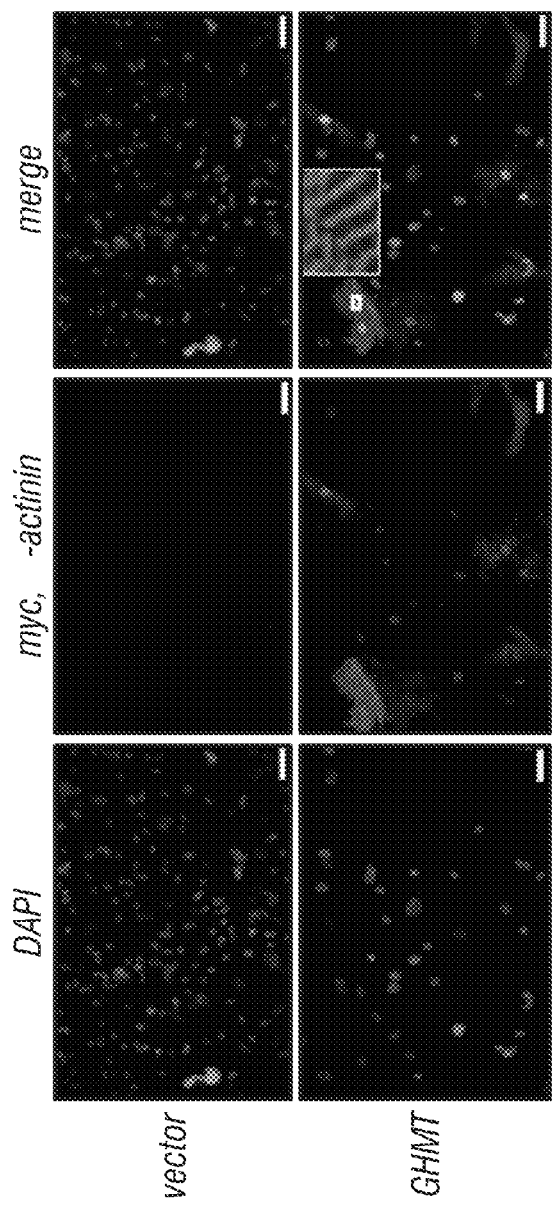
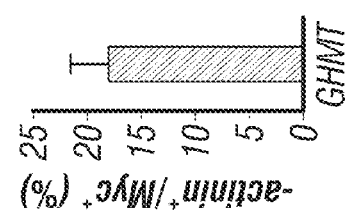
FIG. 18A
FIG. 18B

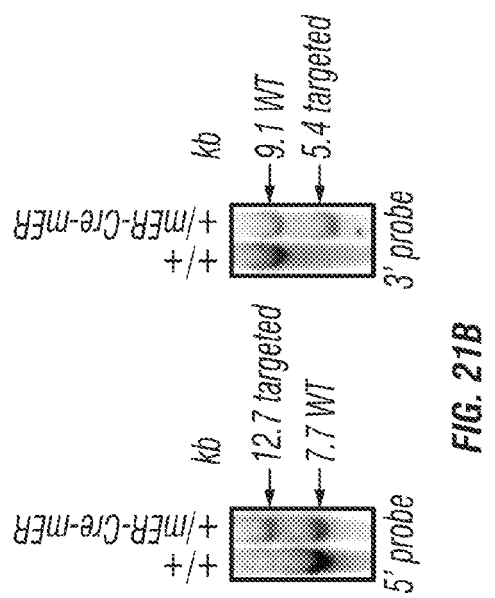
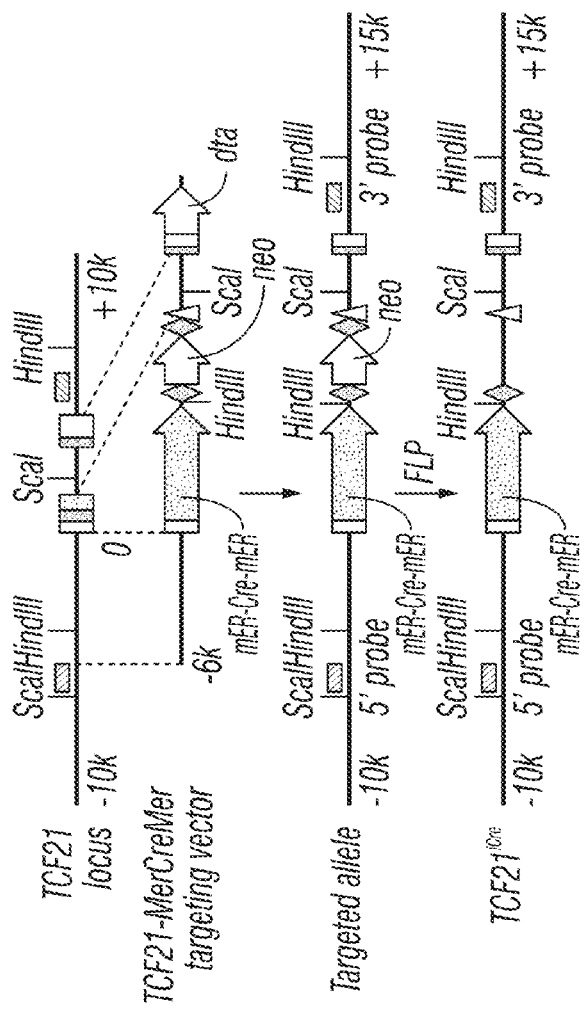
FIG. 21B
FIG. 21A

CARDIAC REPAIR BY REPROGRAMMING OF CARDIAC FIBROBLASTS INTO CARDIOMYOCYTES

This application is a continuation of U.S. application Ser. No. 13/402,609, filed Feb. 22, 2012, now U.S. Pat. No. 9,017,661, which claims benefit of priority to U.S. Provisional Application Ser. No. 61/445,390, filed Feb. 22, 2011, the entire contents of which are hereby incorporated by reference.

The invention was made with government support under grant no. 1U01 HL100401-01 awarded by the National Institutes of Health (NHLBI). The government owns certain rights in the invention.

BACKGROUND OF THE INVENTION

1. Field of the Invention

The present invention relates generally to the fields of cardiology, developmental biology and molecular biology. More particularly, it concerns gene regulation and cellular physiology in cardiomyocytes. Specifically, the invention relates to the use various transcription factors to reprogram cardiac fibroblasts into cardiomyocytes and the use of such factors in the prevention of scarring and repair in post-myocardial infarction.

2. Description of Related Art

Myocardial infarction (MI) or acute myocardial infarction (AMI), commonly known as a heart attack, is the interruption of blood supply to a part of the heart, causing heart cells to die. This is most commonly due to occlusion (blockage) of a coronary artery following the rupture of a vulnerable atherosclerotic plaque, which is an unstable collection of lipids (fatty acids) and white blood cells (especially macrophages) in the wall of an artery. The resulting ischemia (restriction in blood supply) and oxygen shortage, if left untreated for a sufficient period of time, can cause damage or death (infarction) of heart muscle tissue (myocardium). Heart attacks are the leading cause of death for both men and women worldwide.

An MI is a medical emergency which requires immediate medical attention. Treatment attempts to salvage as much myocardium as possible and to prevent further complications, thus the phrase "time is muscle." Oxygen, aspirin, and nitroglycerin may be administered. Morphine was classically used if nitroglycerin was not effective; however, it may increase mortality in the setting of NSTEMI. Coronary intervention (PCI) or fibrinolysis are recommended in those with an STEMI. In people who have multiple blockages and who are relatively stable, or in a few emergency cases, bypass surgery may be an option. However, more effective treatment options are needed, particularly those preventing post-MI scarring that leads to loss of cardiac function.

SUMMARY OF THE INVENTION

Thus, in accordance with the present invention, there is provided a method of reprogramming a cardiac fibroblast comprising contacting the cardiac fibroblast with Tbx5, Mef2C and Hand2. Contacting may comprise delivering Tbx5, Mef2C and Hand2 proteins to the cardiac fibroblast. One or more of the Tbx5, Mef2C and Hand2 may comprise a heterologous cell permeability peptide (CPP). The method may further comprise contacting the cardiac fibroblast with Gata4, with myocardin, or with both Gata4 and myocardin. Contacting may comprise delivering Tbx5, Mef2C and Hand2 expression cassettes to the cardiac fibroblasts, such as expression cassettes comprised in replicable vectors, including viral vectors (e.g., adenoviral vectors or retroviral vectors) or non-viral vectors (optionally disposed in a lipid delivery vehicle). The method may further comprising contacting the cardiac fibroblast with a Gata4 expression cassette, a myocardin expression cassette or both a Gata4 and a myocardin expression cassette.

In another embodiment, there is provided a method of treating a subject having suffered a myocardial infarct (MI) comprising delivering to the subject the Tbx5 and Mef2C or Tbx5 and Mef2C expression cassettes. The method may comprise administration of Tbx5 and Mef2C proteins to the subject, for example, with Tbx5 and/or Mef2C comprising a heterologous cell permeability peptide (CPP). The method may further comprise delivering to the subject one, two or all three of Hand2, myocardin and/or Gata4 proteins. The method may alternatively comprise administration of Tbx5 and Mef2C expression cassettes to the subject, and may further comprise delivering to the subject one, two or all three of Hand2, myocardin and/or Gata4 expression cassettes. The expression cassettes are comprised in replicable vectors, such as viral vectors (e.g., adenoviral vectors or retroviral vectors), or non-viral vectors (optionally including those disposed in a lipid delivery vehicle). The Tbx5 and Mef2C or Tbx5 and Mef2C expression cassettes may be delivered 24 hours to one month following the MI, and may further comprise delivering Hand2, myocardin and/or Gata4 or Hand2, myocardin and/or Gata4 expression cassettes within 24 hours to one month following MI. The proteins or expression cassettes may be delivered multiple times, such as 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 times. The proteins expression cassettes may be delivered daily. The proteins or expression cassettes may be delivered via intracardiac injection. The subject may be further administered oxygen, aspirin, and or nitroglycerin, or further administered percutaneous coronary intervention, or further administered a fibrinolytic. The MI may be non-ST-elevated MI or ST-elevated MI.

In yet another embodiment, there is provided a method preventing or delaying development of cardiac hypertrophy or heart failure in a subject having suffered a myocardial infarct (MI) comprising providing to the subject the Tbx5 and Mef2C or Tbx5 and Mef2C expression cassettes. The method may further comprise administering to the subject a secondary anti-hypertrophic or heart failure therapy, such as a PKD inhibitor, a beta blocker, an ionotrope, a diuretic, ACE-I, AII antagonist, BNP, a $Ca^{++}$ blocker, or an HDAC inhibitor. Preventing or delaying may comprise preventing or delaying cardiac hypertrophy. Preventing or delaying may also comprise preventing or delaying one or more of decreased exercise capacity, decreased cardiac ejection volume, increased left ventricular end diastolic pressure, increased pulmonary capillary wedge pressure, decreased cardiac output or cardiac index, increased pulmonary artery pressures, increased left ventricular end systolic and diastolic dimensions, increased left and right ventricular wall stress, increased wall tension, decreased quality of life, and/or increased disease related morbidity or mortality. The method may further comprising administering Hand2, myocardin and/or Gata4 proteins or Hand2, myocardin and/or Gata4 expression cassettes to the subject.

Additional embodiments include:
  a method of reducing decrease in exercise tolerance of a subject having suffered a myocardial infarction comprising administering to the subject Tbx5 and Mef2C or Tbx5 and Mef2C expression cassettes;

a method of reducing hospitalization of a subject having suffered a myocardial infarction comprising administering to the subject Tbx5 and Mef2C or Tbx5 and Mef2C expression cassettes;

a method of improving quality of life of a subject having suffered a myocardial infarction comprising administering to the subject Tbx5 and Mef2C or Tbx5 and Mef2C expression cassettes;

a method of decreasing morbidity of a subject having suffered a myocardial infarction comprising administering to the subject Tbx5 and Mef2C or Tbx5 and Mef2C expression cassettes;

a method of decreasing mortality of a subject having suffered a myocardial infarction comprising administering to the subject Tbx5 and Mef2C or Tbx5 and Mef2C expression cassettes;

wherein each of the foregoing methods may rely upon and comprises any of the preceding embodiments, including in particular further comprising administering Hand2, myocardin and/or Gata4 or Hand2, myocardin and/or Gata4 expression cassettes to the subject.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIGS. 1A-B) Immunofluorescent staining for cardiac markers, αMHC-GFP and β-actinin. Adult TTFs (FIG. 1A) and CFs (FIG. 1B) isolated from αMHC-GFP reporter mice were transduced by retroviruses carrying GHMT or vector. Immunocytochemistry was performed after 14 days of transduction. Sarcomeric structures were observed (bottom panel). White boxes are enlarged in insets. Scale bar, 40 μm. (FIG. 1C) Measurement of calcium transients in the indicated cell types. Representative calcium transient traces depicted as Fura-2 Ratios (340/380 nm) in the indicated cell types. iCLMs were derived from adult CFs and display a pattern of calcium transients most similar to neonatal ventricular cardiomyocytes. (FIG. 1D) Summary of reprogramming efficiency by GHMT or GMT.

(FIG. 2A) LAD ligated hearts were injected with retroviral GHMT and retroviral Tomato marker. One month later, cardiomyocytes were isolated from injured hearts and visualized under a fluorescent microscope. Upper panel shows tomato staining and lower panel shows phase contrast image. Scale bar, 40 μm. (FIG. 2B) Lineage tracing of reprogrammed cells by GHMT in FSP1-cre; Rosa26-LacZ mice following MI. β-gal+ cardiomyocytes (blue) originate from fibroblasts. X-gal staining was performed 3 weeks post-MI. β-gal+ cells were barely observed in uninjured heart (left). Sections from two different severities of MI with GFP-infection are shown; mild (second from the left) and severe (third from the left). While GFP-infected myocardium showed only β-gal+ non-cardiomyocytes (middle four panels), GHMT-infected myocardium showed extensive β-gal+ non-cardiomyocytes and cardiomyocytes (right). Black boxes in top panels are enlarged in lower panels. Scale bar, 100 μm. (FIG. 2B) While no β-gal+ cells in GFP-infected injured hearts expressed cTnT (second from the left), a fraction of β-gal+ cells in GHMT-infected injured hearts expressed cTnT (right four panels) and displayed organized sarcomeres (right). β-gal+ cells marked by an indicated number in the upper panels represent cTnT+ cells marked by a corresponding number in lower panels. White boxes in right panels are enlarged in insets. Sections of injured hearts were at the border zone. The section of uninjured heart is from LV. Scale bar, 40 μm. (FIG. 2D) Quantification of β-gal+ cardiomyocytes in LV per section in uninjured (56 sections from one mouse), GFP-infected injured (168 sections at 4 levels with an interval of 250 μm below LAD ligation site from three mice) and GHMT-infected injured heart of FSP1-cre; Rosa26-LacZ mice (20 sections at 4 levels with an interval of 250 μm below LAD ligation site from 2 mice). Data are presented as mean±std. (FIG. 2E) Tamoxifen treated Tcf21iCre; Rosa26RtdT mice were subjected to LAD ligation followed by injection of GFP or GHMT retroviruses. One month later, hearts were sectioned and stained for cTnT and visualized for tomato. 1, 2, and 3 show cardiomyocytes positive for tomato in the border zone. Scale bars, 40 μm. (FIG. 2F) Quantification of tomato-positive cardiomyocytes per section in Tcf21 lineage-tagged hearts following the indicated treatments. Twenty sections from one uninjured heart, 12 sections at 4 levels with an interval of 250 μm below LAD ligation site from 2 hearts, and 8 sections at 4 levels with an interval of 250 μm below LAD ligation site from 1 heart, were examined. Data are presented as mean±std. (FIG. 2G) Formation of iCLMs in hindlimb following cardiotoxin injury. Sections were stained for cTnT (red) and wheat germ agglutinin (WGA) to visualize cell boundaries (green). Scale bar, 40 μm. (FIG. 2H) Serial sections of injured skeletal muscle stained for cTnT (red), fast and slow skeletal muscle MHC (red) and WGA (green), as indicated. Scale bar, 40 μm. (FIG. 2I) Quantification of iCLMs in injured mouse hindlimb. Percentage of cTnT+myocytes in injured area=100·(number of cTnT+ myocytes/(number of cTnT+myocytes+number of myocytes with central nuclei). The injured area of the tibialis anterior muscle was immunostained for cTnT expression. Numbers of cTnT+ myocytes and myocytes with central nuclei were counted from 2 mice injected with GFP virus and 4 mice injected with GHMT viruses. cTnT positive myocytes were not observed in GFP-injected muscle. Data are presented as mean±std.

(FIG. 3) Cx43 staining between β-gal+ and β-gal− cardiomyocytes at the border zone. β-gal+ cells marked by an indicated letter in the upper panel represent cTnT+ cells marked by a corresponding letter in the lower panel. Gap junctions (green) were observed between β-gal+ and β-gal− cardiomyocytes (A and B) and between β-gal+ cardiomyocytes (C and D). Scale bar, 40 um. (FIG. 3B) In vivo reprogrammed cardiomyocytes (β-gal+−cardiomyocytes) demonstrating similar contractility and $Ca^{2+}$ transients to bona fide ventricular cardiomyocytes (β-gal− cardiomyocytes). The β-gal+−cardiomyocytes were labeled with a fluorogenic β-gal substrate C12FDG in green under a fluorescence microscope. Representative traces of sarcomere shortening were recorded from field-stimulated β-gal− cardiomyocyte (top) and β-gal+−cardiomyocytes (middle and bottom). Fifteen β-gal− cardiomyocytes (6 cardiomyocytes isolated from injured FSP1-Cre; Rosa26-LacZ mice and 9 cardiomyocytes isolated from uninjured wild type mice) and 7 β-gal+−cardiomyocytes with striated morphology were examined. All β-gal− cardiomyocytes display functional patterns as shown (top). Type A β-gal+−cardiomyocytes, 5 of 7 (71.4%) display a similar pattern of contractility and $Ca^{2+}$ transients to bona fide ventricular cardiomyocytes, whereas Type B β-gal+−cardiomyocytes, 2 of 7 (28.6%) demonstrate immature contractility (bottom).

(FIG. 4A) Evaluation of cardiac function by EF and FS using echocardiography at 24 hours, 2 weeks, and 3 weeks post-MI. Mice at the age of 8 weeks were subjected to LAD ligation followed by intramyocardial injection of GFP or GHMT retroviruses. Data are presented as mean±std. *: $p<0.05$, **: $p<0.005$, ns: not statistically significant. (FIG. 4B) Evaluation of cardiac function at 6 and 12 weeks post-MI by cardiac MRI. EF and stroke volume were assessed. Mice at the age of 8 weeks were ligated and injected with retroviruses carrying either GFP or GHMT. Cardiac function of these mice 6 weeks and 12 weeks post-MI were examined by MRI. Data are presented as mean±std. *: $p<0.05$, : $p<0.005$. (FIG. 4C) Comparison of the extent of cardiac fibrosis and scar formation between GFP and GHMT infected myocardium following MI. Cardiac fibrosis was evaluated at 5 different levels of the LV (L1-L5) by trichrome staining 4 weeks after LAD ligation. The ligation site was marked as X. The severity of cardiac fibrosis was classified as mild (fibrotic area <20%), moderate (fibrotic area 20-40%) or severe (fibrotic area >40%) in each group. The number indicates the number of hearts showing indicated severity out of total number of hearts subjected to MI in each group. Scale bar, 1 mm. (FIG. 4D) Quantification of cardiac fibrosis in the heart sections displayed in FIG. 4B. Fibrotic area (%)=(the sum of fibrotic area at levels 3 and 4/the sum of myocardial area in the LV at levels 3 and 4)×100. : $p<0.005$.

(FIG. 5A) Transgenic mice harboring an αMHC-GFP transgene, which is expressed specifically in cardiomyocytes, were generated. Adult fibroblasts isolated from tail-tip or heart were infected with retroviruses encoding candidate cardiac transcription factors. Cells were analyzed for the expression of GFP and/or cardiac markers by flow cytometry. (FIG. 5B) Schematic of αMHC-GFP transgene. A 5.5 kb genomic fragment upstream of the mouse αMHC gene and also encompassing exons 1-3 and intronic sequences, as described previously (Subramaniam et al., 1991), was cloned upstream of a neomycin-resistance cassette followed by an Internal Ribosomal Entry Sequence (IRES) and a GFP reporter, followed by a human growth hormone (hGH) polyadenylation sequence. (FIG. 5C) Phase and fluorescent images of cells and tissues isolated from αMHC-GFP transgenic mice demonstrating cardiomyocyte-specific expression of the transgene. (FIG. 5D) Phase contrast (upper panels) and GFP fluorescent images (lower panels) of a typical cardiomyocyte isolated from an adult αMHC-GFP transgenic mouse (left panels) and GHMT-induced cardiac-like myocyte (iCLM) from CFs isolated from an αMHC-GFP transgenic mouse (right panels). Intensity of GFP fluorescence is similar in cardiomyocyte and iCLM.

(FIG. 7A) Representative flow cytometry plots for analyses of αMHC-GFP+ cells after 9 days of transduction. The indicated combinations of cardiac transcription factors were transduced into adult TTFs isolated from αMHC-GFP reporter mice. Six factors include GATA4 (G), HAND2 (H), Tbx5 (T), MEF2C (M), Mesp1 (Ms), Nkx2-5 (N). Five factors are six factors minus Nkx2-5. The numbers in each plot indicate the percentage of αMHC-GFP+ cells. Dead cells were excluded by propidium iodide (PI) staining Cells transduced with empty vector retrovirus were used as a control. (FIG. 7B) Summary of flow cytometry analyses. Percentage of αMHC-GFP+ cells following infection of TTFs with retroviruses expressing 6 factors, 5 factors (GHMMsT) or 4 factors (5 factors minus one factor) (left panel); 4 factors (GHMT) or 4 factors minus one (middle panel); 3 factors (HMT), 3 factor minus one, or individual factors (G, H, M, T) (right panel). Data from two independent experiments are presented as mean±std.

(FIG. 9A) Flow cytometry plots for analysis of positive cells for two cardiac markers, cTnT and αMHC-GFP, in adult TTFs at the indicated time points after retroviral transduction of GHMT (upper panel) or GMT (lower panel). Cells transduced with empty vector retrovirus were used as a control. (FIG. 9B) Summary of the flow cytometry analysis in FIG. 9A. The slight decline in the percentage of double-positive cells with time may be due to proliferation of uninduced fibroblasts.

(FIG. 10A) Flow cytometry plots for analyses of positive cells for two cardiac markers, cTnT and αMHC-GFP, induced by GHMT or GMT in adult CFs after 7 days of transduction. Cells transduced with empty vector retrovirus were used as a control. (FIG. 10B) Flow cytometry plots for analyses of positive cells for two endogenous cardiac markers, cTnT and cTnI, induced by GHMT. Cells transduced with empty retrovirus were used as a control.

(FIG. 12A) Two types of α-actinin positive induced cardiac-like myocytes (iCLMs) are observed in CFs and TTFs transduced with GHMT. The cell type on the left (referred to as cell type A) displays highly organized sarcomeres, whereas the cell type on the right (referred to as cell type B) shows more diffuse α-actinin staining Scale bar, 40 μm. (FIG. 12B) Quantification of iCLMs derived from adult CFs. Numbers of cell type A, B, and DAPI in 15 randomly chosen fields from two independent experiments were counted Data are presented as mean±std. (FIG. 12C) Quantification of iCLMs derived from adult TTFs. Numbers of cell types A and B, and DAPI-stained cells in 20 randomly chosen fields from four independent experiments were counted. Data are presented as mean±std.

(FIG. 13A) Experimental design. Adult CFs were transduced with empty vector or GHMT retroviruses and harvested 2 or 4 weeks after infection. (FIG. 13B) Microarray design. RNA isolated from infected and uninfected CFs, and adult heart was analyzed for gene expression profile by microarray using illumina Mouse-6 Beadchip (Illumina) comprised of 45,281 probes. (FIG. 13C) Heatmap of microarray data illustrating differentially expressed genes in CFs, vector-transduced CFs, GHMT-transduced CFs and adult heart. Red indicates upregulated genes whereas green indicates down-regulated genes. (FIG. 13D) Gene Ontology analysis by PANTHER Expression tool (world-wide-web at pantherdb.org) categorizes genes that are up-regulated in GHMT transduced CFs. (FIG. 13E) Heatmap of selected genes. Genes that encode for cardiac contractile proteins, cardiac peptides, $Ca^{2+}$ handling proteins, cardiac transcription factors and cardiac metabolism are up-regulated in GHMT transduced CFs, as seen in adult heart, compared to vector transduced CFs. In contrast, genes encoding non-myocyte markers are down-regulated. S100A4 (FSP1), COL16A1 and COL1A1 are fibroblast markers. TAGLN2 is a smooth muscle marker. PLP2 is an epithelial-enriched gene.

(FIG. 15A) Neonatal cardiomyocytes and fibroblasts immunostained for α-actinin (red) and prolyl 4-hydroxylase, beta polypeptide (P4HB) (green), respectively. These two markers do not co-localize. Boxed area is enlarged in inset and shows sarcomeres. Nuclei were stained with DAPI. Scale bar, 40 μm. (FIG. 15B) Adult CFs transduced with empty vector or GHMT retroviruses were immunostained for α-actinin (red) and P4HB (green). Nuclei were stained with DAPI (blue). CFs transduced with empty vector stained P4HB-positive and α-actinin negative (left panel). CFs transduced with GHMT retroviruses staining positive for α-actinin were classified into three categories (A, B and C) based on the staining pattern of P4HB. A, P4HB positive staining; B, weak but detectable P4HB staining; and C, undetectable P4HB staining Scale bar, 40 μm. (FIG. 15C) Cells of each category (A, B and C) described in FIG. 15B were quantified as percentage of total α-actinin+ cells. Data are presented as mean±std.

(FIG. 17A) Experimental design and schematic diagrams of lentiviral vectors. CFs isolated from adult mice were transduced with tetracycline-inducible viruses encoding GMT described previously 7, and HAND2 tagged with a Myc-epitope. Doxycycline (Dox) was added to induce expression of factors on day 2 and removed on day 12, as indicated. Expression of cardiac markers was analyzed on day 30 by immunostaining for α-actinin and Myc. (FIG. 17B) Immunostaining for α-actinin (red) and Myc (green) in lentiviral GHMTtransduced CFs. Dox was present in the culture for 29 days (upper panels) or withdrawn at day 12 (lower panels). Boxed regions are enlarged to show sarcomere-like structures. Note that upon removal of Dox, Myc staining disappeared but α-actinin staining was maintained (lower panels). Nuclei were stained with DAPI (blue).

FIGS. 18A-B. Induction of iCLMs by GHMT is cell-autonomous. (FIG. 18A) Immunostaining for α-actinin (red) and Myc (green) in retroviral GHMTtransduced CFs. Boxed regions are enlarged to show sarcomere-like structures. Nuclei were stained with DAPI (blue). (FIG. 18B) Quantification of percentage of α-actinin positive cells in Myc positive cells. α-actinin and Myc positive cells were counted in 37 randomly chosen fields from two independent experiments. Data are presented as mean±std.

(FIG. 19A) Illustration of intramyocardial retrovirus injection at five separate areas of the border zone in an infracted heart. (FIG. 19B) Four days after MI and subsequent GFP-retrovirus injection, the heart was harvested and sectioned. H&E staining and immunohistochemistry were performed. GFP expression (green) (right) was only detected in the ischemic area surrounded with a white line (left). Staining with secondary antibody alone was used as a negative control. Scale bar, 100 μm. (FIG. 19C) Immunohistochemistry of border zone showing expression of cTnT (red) and GFP (green) at different magnifications. GFP did not co-localize with cTnT expression Nuclei were stained with DAPI (blue). Scale bars, 40 μm (upper), 20 μm (lower). (FIG. 19D) Quantification of GFP+ cells per heart section. GFP+ cells were counted from 8 sections at 8 levels at intervals of 250 μm below the LAD ligation site.

(FIG. 20A) Three weeks after MI and subsequent GHMMsNT- or GHMMsT-retrovirus injection, the hearts of FSP1-cre/Rosa26-LacZ mice were harvested and stained with a β-gal substrate. GHMMsT-infected hearts showed more β-gal+-cardiomyocyte-like cells than GHMMsNT-infected hearts. Regions indicated by black box (left) were enlarged in middle and right panels. Scale bar, 40 μm. (FIG. 20B) Quantification of β-gal+ cardiomyocytes in LV per section in uninjured (56 sections from one mouse), GFP-infected injured (168 sections from three mice), GHMMsNT (189 sections from four mice), GHMMsT (66 sections from two mice) and GHMT-infected injured heart of FSP1-cre/Rosa26-LacZ mice (20 sections from 2 mice). All sections were taken at 4 levels with an interval of 250 μm below LAD ligation site. Data are presented as mean±std.

FIGS. 21A-E. Generation of Tcf21iCre/+ knockin mice and characterization of Tcf21 lineage tagged cells. (FIG. 21A) Structure of Tcf21 locus and strategy for generation of Tcf21iCre/+ knock-in mice. A targeting strategy to knock-in an inducible Cre (MerCreMer) into the Tcf21 locus to replace the first exon of the Tcf21 gene. Mice with the targeted allele were crossed with FLPe transgenic mice which removes the neomycin resistant cassette to generate Tcf21iCre/+ mice. The red and blue bars represent the 5' and 3' probes for Southern blot analysis, respectively. ♦ denotes FLP (Flippase Recognition Target) site. (FIG. 21B) Confirmation of targeting by Southern blot analysis. Genomic DNA digested with Sca I was hybridized to 5' probe, shown in a. The wild-type (WT) band migrated at 7.7 kb, but the targeted band migrated at 12.7 kb. Genomic DNA digested with Hind III and hybridized to 3' probe, shown in a. The WT band migrated at 9.1 kb and the targeted band migrated at 5.4 kb. Genotypes were shown on top. (FIG. 21C) Schematic of experimental design to isolate Tcf21 lineage tagged cells in adult mouse heart. Tcf21iCre/+(Tcf21-MerCreMer) mice were crossed with R26RtdT (Rosa26-Tomato) mice to obtain mice carrying Tcf21iCre/+: R26RtdT alleles. Activation of Cre in Tcf21-expressing cells was induced by gavage of mice with tamoxifen for 3 consecutive days. One week later, hearts were digested and Tcf21 lineage tagged cells were sorted for Tomato expression. RNA was isolated from dissociated heart cells and Tomato+ cells. (FIG. 21D) qPCR was performed to detect expression of genes marking different cell types. Fibroblast-specific markers are enriched in Tomato+Tcf21-lineage tagged cells (upper panel). In contrast, cardiomyocyte-markers (CM) and vascular smooth muscle cellmarkers (VSMC) were undetectable or negligibly expressed (lower panel). These findings indicate that Tcf21 reliably marks cardiac fibroblasts in mouse hearts. Relative gene expression is determined by comparing expression of sorted Tomato+ cells to dissociated heart cells. (FIG. 21E) Immunohistochemistry for Tcf21 lineage tagged cells. Heart sections from tamoxifen-induced mice carrying Tcf21iCre/+: R26RtdT alleles were stained for P4HB (fibroblasts), SM22a (smooth muscle cells), isolectin B4 (endothelial cells), and cTnT (cardiomyocytes). Tcf21 lineage tagged cells co-stain with the cardiac fibroblast marker (P4HB) but not with cardiomyocyte or other non-cardiomyocyte markers. Scale bar, 40 μm.

(FIG. 23A) Schematic of genetic fate mapping study of cardiomyocytes. αMHC-MerCreMer transgenic mice were crossed with Rosa26-LacZ reporter mice. Following administration of tamoxifen for 7 consecutive days, the LacZ reporter gene switches on in the majority of cardiomyocytes. LAD ligation was then performed 7 days after gavage of the last dose of tamoxifen and retroviruses encoding GFP or GHMT were injected into the heart. At day 45, mice were sacrificed and LacZ expression was determined in histological sections of the heart. The presence of a higher percentage of LacZ-negative cardiomyocytes in GHMT-injected hearts reflects the reprogramming of unlabeled cells to a cardiac fate. (FIG. 23B) Transverse sections of αMHC-MerCreMer; Rosa26-LacZ hearts, either uninjured (left), or injured and infected with GFP retroviruses (center) or GHMT retroviruses (right) were stained to detect β-galactosidase activity (blue). The boxed regions are enlarged in the lower panels. Scale bar, 2 mm (upper), 40 μm (middle and lower). (FIG. 23C) Quantification of beta-galactosidase negative cardiomyocytes in the border zone of LAD ligated mice injected with GFP or GHMT retroviruses, as indicated. Three sections at three different levels with intervals of 250 μm below LAD ligation site from each heart were examined. Data is presented as mean±std. The p-value was calculated with two-tail t-test.

DETAILED DESCRIPTION OF ILLUSTRATIVE EMBODIMENTS

Figure 1A:
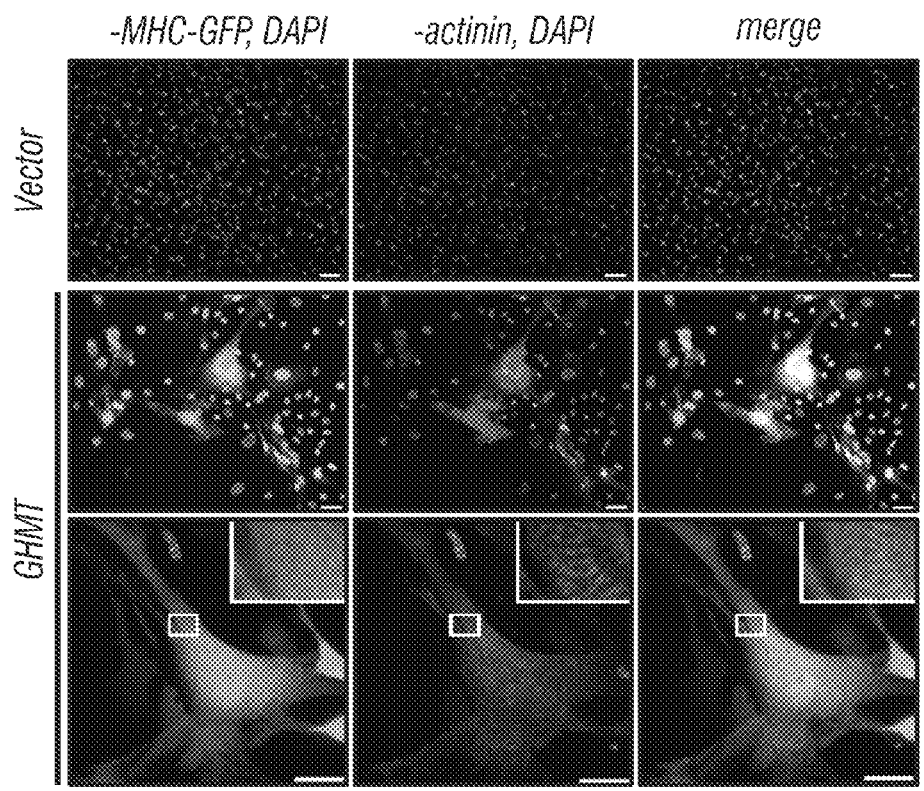
FIGS. 1A-D. Reprogramming fibroblasts toward a cardiac phenotype in vitro by GHMT.

Heart failure is one of the leading causes of morbidity and mortality in the world. In the U.S. alone, estimates indicate that 3 million people are currently living with cardiomyopathy and another 400,000 are diagnosed on a yearly basis. Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars.

One particularly severe manifestation of heart disease is myocardial infarction (MI). Typically, MI results from an acute thrombocytic coronary occlusion that occurs in a coronary artery as a result of atherosclerosis and causes myocardial cell death, i.e., an infarct. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. Cardiac hypertrophy is an adaptive response of the heart to virtually all forms of cardiac disease, including myocardial infarction. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

Treatment with pharmacological agents still represents the primary mechanism for reducing or eliminating the manifestations of heart failure, including those resulting from MIs. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure. If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. More importantly, none of these agents are capable of reversing the damage caused by an acute coronary event, and thus are only compensatory, and only then to a certain degree. The prognosis for patients with DCM is variable, and depends upon the degree of ventricular dysfunction, with the majority of deaths occurring within five years of diagnosis. The present invention therefore provides a revolutionary way to address MI by preventing or limiting the damage that leads to loss of cardiac function. By providing a series of cardiac transcription factors, one can now convert cardiac fibroblasts, which are responsible for scarring in post-ischemic myocardium, into cardiomyocytes, which are capable of regenerating cardiac muscle, thereby replacing tissues lost due to the infarction as well as reducing function-impairing scarring. These and other aspects of the invention are described in detail below.

I. TRANSCRIPTION FACTORS

A transcription factor (sometimes called a sequence-specific DNA-binding factor) is a protein that binds to specific DNA sequences, thereby controlling the movement (or transcription) of genetic information from DNA to mRNA. Transcription factors perform this function alone or with other proteins in a complex, by promoting (as an activator), or blocking (as a repressor) the recruitment of RNA polymerase (the enzyme that performs the transcription of genetic information from DNA to RNA) to specific genes.

A defining feature of transcription factors is that they contain one or more DNA-binding domains (DBDs), which attach to specific sequences of DNA adjacent to the genes that they regulate. Additional proteins such as coactivators, chromatin remodelers, histone acetylases, deacetylases, kinases, and methylases, while also playing crucial roles in gene regulation, lack DNA-binding domains, and, therefore, are not classified as transcription factors.

The present invention involves the inventor's observation that certain well-known transcription factors can combine to reprogram cardiac fibroblasts into cardiomyocytes, and can do so in situ without the need for complicated ex vivo culturing steps and readministration. In particular, it is shown that Tbx5 and Mef2C are crucial to achieving the fibroblast-cardiomyocyte conversion, while Myocardin, Hand 2 and Gata4 are able to enhance the effect. Thus, combinations including Tbx5+Mef2C, Tbx5+Mef2C+Hand2, Tbx5+Mef2C+Gata4, Tbx5+Mef2C+Gata4+Hand2, Myocardin+Tbx5+Mef2C, Myocardin+Tbx5+Mef2C+

Hand2, Myocardin+Tbx5+Mef2C+Gata4 and Myocardin+ Tbx5+Mef2C+Gata4+Hand2 are contemplated, as well as the addition of other factors.

A. Tbx5

T-box transcription factor TBX5 is a protein that in humans is encoded by the TBX5 gene. This gene is a member of a phylogenetically conserved family of genes that share a common DNA-binding domain, the T-box. T-box genes encode transcription factors involved in the regulation of developmental processes. This gene is closely linked to related family member T-box 3 (ulnar mammary syndrome) on human chromosome 12. The encoded protein may play a role in heart development and specification of limb identity. Mutations in this gene have been associated with Holt-Oram syndrome, a developmental disorder affecting the heart and upper limbs. Several transcript variants encoding different isoforms have been described for this gene. See Basson et al. (1997) and Terrett et al. (1994).

TBX5 (T-box 5); mRNA=NM_000192 (SEQ ID NO: 1); Protein=NP_000183 (SEQ ID NO: 2).

B. Mef2C

Myocyte-specific enhancer factor 2C also known as MADS box transcription enhancer factor 2, polypeptide C is a protein that in humans is encoded by the MEF2C gene. MEF2C is a transcription factor in the Mef2 family. The gene is located at 5q14.3 on the minus strand and is 200,723 bases in length. The encoded protein has 473 amino acids with a predicted molecular weight of 51.221 kD. Three isoforms have been identified. Several post translational modifications have been identified including phosphorylation on serine-59 and serine-396, sumoylation on lysine-391, acetylation on lysine-4 and proteolytic cleavage. The mature protein is found in the nucleus and the gene's expression is maximal in the post natal period.

MEF2C has been shown to interact with MAPK7, EP300, Sp1 transcription factor, TEAD1, SOX18, HDAC4, HDAC7 and HDAC9. This gene is involved in cardiac morphogenesis and myogenesis and vascular development. It may also be involved in neurogenesis and in the development of cortical architecture. Mice without a functional copy of the Mef2c gene die before birth and have abnormalities in the heart and vascular system. In humans mutations of this gene have resulted in severe psychomotor retardation, periodic tremor and an abnormal motor pattern with mirror movement of the upper limbs observed during infancy, hypotonia, abnormal EEG, epilepsy, absence of speech, autistic behavior, bruxism, and mild dysmorphic features, mild thinning of the corpus callosum and delay of white matter myelination in the occipital lobes. See McDermott et al. (1993) and Molkentin et al. (1996).

MEF2C (myocyte enhancer factor 2C); mRNA=NM_002397 (SEQ ID NO: 3); Protein=NP_002388 (SEQ ID NO: 4).

C. GATA4

Transcription factor GATA-4 is a protein that in humans is encoded by the GATA4 gene. This gene encodes a member of the GATA family of zinc finger transcription factors. Members of this family recognize the GATA motif which is present in the promoters of many genes. This protein is thought to regulate genes involved in embryogenesis and in myocardial differentiation and function. Mutations in this gene have been associated with cardiac septal defects as well as reproductive defects. GATA4 has been shown to interact with NKX2-5, TBX5, ZFPM2, Serum response factor, HAND2 and HDAC2. See White et al. (1995).

GATA4 (GATA binding protein 4); mRNA=NM_002052 (SEQ ID NO: 5); Protein=NP_002043 (SEQ ID NO: 6).

D. Hand2

Heart- and neural crest derivatives-expressed protein 2 is a protein that in humans is encoded by the HAND2 gene. The protein encoded by this gene belongs to the basic helix-loop-helix family of transcription factors. This gene product is one of two closely related family members, the HAND proteins, which are asymmetrically expressed in the developing ventricular chambers and play an essential role in cardiac morphogenesis. Working in a complementary fashion, they function in the formation of the right ventricle and aortic arch arteries, implicating them as mediators of congenital heart disease. In addition, this transcription factor plays an important role in limb and branchial arch development. See Russell et al. (1999).

HAND2 (heart and neural crest derivatives expressed 2); mRNA=NM_021973 (SEQ ID NO: 7); Protein=NP_068808 (SEQ ID NO: 8).

E. Myocardin

Myocardin is a protein that in humans is encoded by the MYOCD gene. Myocardin is a smooth muscle and cardiac muscle-specific transcriptional coactivator of serum response factor. When expressed ectopically in nonmuscle cells, myocardin can induce smooth muscle differentiation by its association with serum response factor (SRF).

MYOCD (myocardin); mRNA=NM_001146312.1 (SEQ ID NO: 9); Protein=NP_001139784.1 (SEQ ID NO: 10).

III. PROTEIN DELIVERY

The present invention, in one aspect, relates to the production and formulation of transcription factors as well as their delivery to cells, tissues or subjects. In general, recombinant production of proteins is well known and is therefore no described in detail here. The discussion of nucleic acids and expression vectors, found below, is however incorporated in this discussion.

A. Purification of Proteins

It will be desirable to purify proteins according to the present invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

B. Cell Permeability Peptides

The present invention contemplates the use of a cell permeability peptide (also called a cell delivery peptide, or cell transduction domain) linked to transcription factors. Such domains have been described in the art and are generally characterized as short amphipathic or cationic peptides and peptide derivatives, often containing multiple lysine and arginine resides (Fischer, 2007). Other examples are shown in Table 1, below.

TABLE 1

CDD/CTD PEPTIDES

| | SEQ ID NO: |
|---|---|
| GALFLGWLGAAGSTMGAKKKRKV | 9 |
| RQIKIWFQNRRMKWKK | 10 |
| RRMKWKK | 11 |
| RRWRRWWRRWWRRWRR | 12 |
| RGGRLSYSRRRFSTSTGR | 13 |
| YGRKKRRQRRR | 14 |
| RKKRRQRRR | 15 |
| YARAAARQARA | 16 |
| RRRRRRRR | 17 |
| KKKKKKKK | 18 |
| GWTLNSAGYLLGKINLKALAALAKXIL | 19 |
| LLILLRRRIRKQANAHSK | 20 |
| SRRHHCRSKAKRSRHH | 21 |
| NRARRNRRRVR | 22 |
| RQLRIAGRRLRGRSR | 23 |
| KLIKGRTPIKFGK | 24 |
| RRIPNRRPRR | 25 |
| KLALKLALKALKAALKLA | 26 |
| KLAKLAKKLAKLAK | 27 |
| GALFLGFLGAAGSTNGAWSQPKKKRKV | 28 |
| KETWWETWWTEWSQPKKKRKV | 29 |
| LKKLLKKLLKKLLKKLLKKL | 30 |
| QAATATRGRSAASRPTERPRAPARSASRPRRPVE | 31 |
| MGLGLHLLVLAAALQGAKSKRKV | 32 |
| AAVALLPAVLLALLAPAAANYKKPKL | 33 |
| MANLGYWLLALFVTMWTDVGLCKKRPKP | 34 |
| LGTYTQDFNKFHTFPQTAIGVGAP | 35 |
| DPKGDPKGVTVTVTVTGKGDPXPD | 36 |
| PPPPPPPPPPPPPP | 37 |
| VRLPPPVRLPPPVRLPPP | 38 |
| PRPLPPPRPG | 39 |
| SVRRRPRPPYLPRPRPPPFFPPRLPPRIPP | 40 |
| TRSSRAGLQFPVGRVHRLLRK | 41 |
| GIGKFLHSAKKFGKAFVGEIMNS | 42 |
| KWKLFKKIEKVGQNIRDGIIKAGPAVAVVGQATQIAK | 43 |
| ALWMTLLKKVLKAAAKAALNAVLVGANA | 44 |
| GIGAVLKVLTTGLPALISWIKRKRQQ | 45 |
| INLKALAALAKKIL | 46 |
| GFFALIPKIISSPLPKTLLSAVGSALGGSGGQE | 47 |
| LAKWALKQGFAKLKS | 48 |
| SMAQDIISTIGDLVKWIIQTVNXFTKK | 49 |
| LLGDFFRKSKEKIGKEFKRIVQRIKQRIKDFLANLVPRTES | 50 |
| PAWRKAFRWAWRMLKKAA | 51 |
| KLKLKLKLKLKLKLKL | 52 |

C. Protein Delivery

In general, proteins are delivered to cells as a formulation that promotes entry of the proteins into a cell of interest. In a most basic form, lipid vehicles such as liposomes. For example, liposomes, which are artificially prepared vesicles made of lipid bilayers have been used to delivery a variety of drugs. Liposomes can be composed of naturally-derived phospholipids with mixed lipid chains (like egg phosphatidylethanolamine) or other surfactants. In particular, liposomes containing cationic or neutral lipids have been used in the formulation of drugs. Liposomes should not be confused with micelles and reverse micelles composed of monolayers, which also can be used for delivery.

A wide variety of commercial formulations for protein delivery are well known including PULSin™, Lipodin-Pro, Carry-MaxR, Pro-DeliverIN, PromoFectin, Pro-Ject, Chariot™ Protein Delivery reagent, BioPORTER™, and others.

Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or mimetic, and can stabilize it to the effects of in vivo environment.

IV. NUCLEIC ACID DELIVERY

As discussed above, in certain embodiments, expression cassettes are employed to express a transcription factor product, either for subsequent purification and delivery to a cell/subject, or for use directly in a genetic-based delivery approach. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |

TABLE 2-continued

Promoter and/or Enhancer

| Promoter/Enhancer | References |
|---|---|
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulk et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the α-actin promoter (Moss et al., 1996), the troponin 1 promoter (Bhaysar et al., 1996); the $Na^+/Ca^{2+}$ exchanger promoter (Barnes et al., 1997), the dystrophin promoter (Kimura et al., 1997), the α7 integrin promoter (Ziober and Kramer, 1996), the brain natriuretic peptide promoter (LaPointe et al., 1996) and the αB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

C. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

V. METHODS OF TREATING MYOCARDIAL INFARCTION

As discussed above, the present invention provides for new post-MI therapies. In one embodiment of the present invention, methods for the treatment of subjects following an MI provides for one or more of the following outcomes as compared to an untreated patient: increased exercise capacity, increased blood ejection volume, decreased left ventricular end diastolic pressure, decreased pulmonary capillary wedge pressure, increased cardiac output, improved cardiac index, decreased pulmonary artery pressures, decreased left ventricular end systolic and diastolic dimensions, and decreased left ventricular wall stress, decreased wall tension and decreased wall thickness-same for right ventricle. In addition, the treatment may prevent progression to cardiac hypertrophy and ultimately heart failure.

Treatment regimens would vary depending on the clinical situation. However, in general, the treatment would begin at a time following an MI when the patient has been stabilized, but before significant cardiac fibroblast mobilization and scarring has begun. The patient may or may not be undergoing one or more other therapies for either prevention or treatment of an MI, or prevention or treatment of MI-related sequelae. This would mean initiating a treatment within about 24, 36, 38, 72, 96 hours of an MI, or within about 5, 6, 7, 8, 9 or 10 days of an MI. The therapy may continue for as long as cardiac fibroblasts would be active within the ischemic zone, such as up to 7 days, 14 days 21 days, 28 days, 1 month, 2 months, 3 months or longer.

A. Combined Therapies

In another embodiment, it is envisioned to use the transcription therapy inhibitor of the present invention in combination with other MI and post-MI therapeutic modalities, such as those discussed above. Combinations may be achieved by contacting cardiac cells/patients with a single composition or pharmacological formulation that includes both agents, or by contacting the cell with two distinct compositions or formulations, at the same time, wherein one composition includes the expression construct and the other includes the agent. Alternatively, the therapy using transcription factors may precede or follow administration of the other agent(s) by intervals ranging from minutes to weeks. In embodiments where the other agent and transcription factors are applied separately to the cardiac cells/patient, one would generally ensure that a significant period of time did not expire between the time of each delivery, such that the agent and transcription factors would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either transcription factors, or the other agent will be desired. In this regard, various combinations may be employed. By way of illustration, where the transcription factors are "A" and the other agent is "B," the following permutations based on 3 and 4 total administrations are exemplary:

| A/B/A | B/A/B | B/B/A | A/A/B | B/A/A | A/B/B |
|---|---|---|---|---|---|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated.

B. Standard MI Therapeutic Intervention

Therapies for acute myocardial infarction are designed to restore perfusion as soon as possible to rescue the infracted myocardium. This is typically done by pharmaceutical intervention or by mechanical means, such as percutaneous coronary intervention (PCI) or coronary artery bypass grafting. Recent studies suggest that these treatments are more effective if the following guidelines are followed: <90 min for PCI and <30 min for lytics. Treatments outside these windows were associated with increased mortality and significantly increased risk of readmission for acute myocardial infarction or heart failure.

1. Drug Therapies

Thrombolytic therapy improves survival rates in patients with acute myocardial infarction if administered in a timely fashion in the appropriate group of patients. If PCI capability is not available within 90 minutes, then choice is to administer thrombolytics within 12 hours of onset of symptoms in patients with ST-segment elevation greater than 0.1 mV in 2 or more contiguous ECG leads, new left bundle-branch block (LBBB), or anterior ST depression consistent with posterior infarction. Tissue plasminogen activator (t-PA) is preferred over streptokinase as achieving a higher rate of coronary artery patency; however, the key lies in speed of the delivery.

Aspirin has been shown to decrease mortality and re-infarction rates after myocardial infarction. Again, delivery should be immediate, which should be chewed if possible. The treatment should continues indefinitely in the absence of obvious contraindication, such as a bleeding tendency or an allergy. Clopidogrel may be used as an alternative in cases of a resistance or allergy to aspirin (dose of 300 mg), but a higher dose of clopidogrel may have added benefit.

Platelet glycoprotein (GP) IIb/IIIa-receptor antagonist is another therapy in patients with continuing ischemia or with other high-risk features and to patients in whom a percutaneous coronary intervention (PCI) is planned. Eptifibatide and tirofiban are approved for this use, and abciximab also can be used for 12-24 hours in patients with unstable angina or NSTEMI in whom a PCI is planned within the next 24 hours.

Heparin and other anticoagulant agents have an established role as adjunct agents in patients receiving t-PA, but not in patients receiving streptokinase. Heparin is also indicated in patients undergoing primary angioplasty. Low molecular-weight heparins (LMWHs) have been shown to be superior to UFHs in patients with unstable angina or NSTEMI. Bivalirudin, a direct thrombin inhibitor, has shown promise in STEMI if combined with high-dose clopidogrel.

Nitrates have no apparent impact on mortality rate in patients with ischemic syndromes, but they are useful in symptomatic relief and preload reduction, so much so that all patients with acute myocardial infarction are given nitrates within the first 48 hours of presentation, unless contraindicated (i.e., in RV infarction). Beta-blockers may reduce the rates of reinfarction and recurrent ischemia, and thus are administered to patients with MIs unless a contraindication is present.

ACE inhibitors reduce mortality rates after myocardial infarction and thus are administered as soon as possible as long as no contraindications are and the patient remains stable. ACE inhibitors have the greatest benefit in patients with ventricular dysfunction. Continue ACE inhibitors indefinitely after myocardial infarction. Angiotensin-receptor blockers may be used as an alternative in patients who develop adverse effects, such as a persistent cough, although initial trials need to be confirmed.

2. PCI and Other Surgical Intervention

PCI is the treatment of choice in most patients with STEMI, assuming a door to balloon time of less than 90 minutes. PCI provides greater coronary patency (>96% thrombolysis), lower risk of bleeding, and instant knowledge about the extent of the underlying disease. Studies have shown that primary PCI has a mortality benefit over thrombolytic therapy. The choice of primary PCI should be individualized to each patient's presentation and timing. Primary PCI is also the treatment of choice in patients with cardiogenic shock, patients in whom thrombolysis failed, and those with high risk of bleeding or contraindications to thrombolytic therapy.

Emergent or urgent coronary artery graft bypass surgery is indicated in patients in whom angioplasty fails and in patients who develop mechanical complications such as a VSD, LV, or papillary muscle rupture.

C. Pharmacological Therapeutic Agents

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

In addition to the transcription factors of the present invention, it should be noted that any of the following may be used to develop new therapeutic regimens in combination with the transcription factors.

1. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of athersclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thryroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

2. Antiarteriosclerotics

Non-limiting examples of an antiarteriosclerotic include pyridinol carbamate.

3. Antithrombotic/Fibrinolytic Agents

In certain embodiments, administration of an agent that aids in the removal or prevention of blood clots may be combined with administration of a modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

4. Blood Coagulants

In certain embodiments wherein a patient is suffering from a hemorrhage or an increased likelihood of hemorrhaging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamin K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

5. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrythmic agents (calcium channel blockers) and miscellaneous antiarythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

b. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

e. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

6. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherally acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a sulfonamide derivative.

Arylethanolamine Derivatives.

Non-limiting examples of arylethanolamine derivatives include amosulalol, bufuralol, dilevalol, labetalol, pronethalol, sotalol and sulfinalol.

Benzothiadiazine Derivatives.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethiazide, methyclothiazide, meticrane, metolazone, paraflutizide, polythizide, tetrachlormethiazide and trichlormethiazide.

N-Carboxyalkyl(Peptide/Lactam) Derivatives.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives.

Non-limiting examples of dihydropyridine derivatives include amlodipine, felodipine, isradipine, nicardipine, nifedipine, nilvadipine, nisoldipine and nitrendipine.

Guanidine Derivatives.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines.

Non-limiting examples of hydrazines/phthalazines include budralazine, cadralazine, dihydralazine, endralazine, hydracarbazine, hydralazine, pheniprazine, pildralazine and todralazine.

Imidazole Derivatives.

Non-limiting examples of imidazole derivatives include clonidine, lofexidine, phentolamine, tiamenidine and tolonidine.

Quanternary Ammonium Compounds.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives.

Non-limiting examples of reserpine derivatives include bietaserpine, deserpidine, rescinnamine, reserpine and syrosingopine.

Suflonamide Derivatives.

Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

7. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

d. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

D. Surgical Therapeutic Agents

In certain aspects, the secondary therapeutic agent may comprise a surgery of some type, such as PCI. Surgery, and in particular a curative surgery, may be used in conjunction with other therapies, such as the present invention and one or more other pharmacologic agents. Such surgical approaches for vascular and cardiovascular diseases and disorders are well known to those of skill in the art, and are described elsewhere in this document.

E. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render drugs, proteins or delivery vectors stable and allow for uptake by target cells. Aqueous compositions of the present invention comprise an effective amount of the drug, vector or proteins, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Adult TTFs and CFs were isolated by an explanting method in which fibroblasts migrate from minced tissue and grow in fibroblast growth medium. Fibroblasts were transduced with a mixture of polybrene (Sigma; 6 µg/ml) and fresh retroviruses expressing transcription factors, made from Platinum E cells (Cell Biolabs). Twenty-four hours after viral transduction, the viral medium was changed to a cardiac induction medium. The medium was changed every two days. Expression of cardiac genes was analyzed by flow cytometry, real-time PCR, and immunocytochemistry. Adult mice, 8-10 weeks old, underwent either a sham operation or ligation of the LAD at 1.5 mm distal to the left atrial appendage. Concentrated retroviruses ($\sim 10^8$ pfu viruses) were injected into the border zone using a gastight 1710 syringe (Hamilton). Cardiac function was assessed using echocardiography and hearts were harvested from euthanized animals for histological studies. Isolation of adult cardiomyocytes, electrophysiological measurements, histological and immunohistochemistry analysis were performed as described previously (19-22).

Isolation of Primary Fibroblasts.

Tail-tip fibroblasts (TTFs): Adult mouse tails were skinned and cut into small pieces which were plated on tissue culture dishes and cultured in DMEM supplemented with 15% FBS and antibiotics. The medium was changed every 2 to 3 days. TTFs migrated out after 2 or 3 days. One week later, TTFs were frozen or replated for viral transduction. Cardiac fibroblasts (CFs): Adult (older than 4 weeks of age) mouse hearts were minced into small pieces and plated on tissue culture dishes. Three minutes later, culture medium (DMEM:199 (4:1), 15% FBS and antibiotics) was gently added to the dishes. CFs started to migrate out of the minced heart tissue after two days. The medium was replaced every two days. Ten days later, CFs were frozen or replated for viral transduction.

Generation of Retroviruses.

Retroviral plasmid DNA was generated by subcloning EGFP, Myc-tagged Nkx2-5, GATA4, Tbx5, HAND2, MEF2C, and FLAG-tagged MesP1 cDNAs into the retroviral vector pBabe-X (Kitamura et al., 1995). Ten micrograms of retroviral plasmid DNA was transfected using Fugene 6 (Roche) into the Platinum E cells (Cell Biolabs) which were plated on a 10-cm tissue culture dish at a density of 3×106 per dish, 24 hours prior to transfection. Twelve hours after transfection, medium was changed to 12 ml of fresh medium (DMEM supplemented with 10% FBS and antibiotics). After 36 hours of transfection, viral medium was harvested and filtered through a 0.45 μm cellulose filter. The viral supernatant was mixed with polybrene (Sigma) to a final concentration of 6 μg/ml.

Viral Transduction.

TTFs and CFs were plated on tissue culture dishes pre-coated with SureCoat (Cellutron) at a density of $0.8 \times 10^4$/cm$^2$. After 24 hours, the fibroblast growth medium was replaced with freshly made viral mixture with polybrene. Twenty four hours later, viral medium was replaced with induction medium, composed of 10% of conditioned medium obtained from neonatal rat/mouse cardiomyocytes, DMEM/199 (4:1), 10% FBS, 5% horse serum, antibiotics, non-essential amino acids, essential amino acids, B-27, insulin-selinum-transferin, vitamin mixture, and sodium pyruvate (Invitrogen). Conditioned medium was filtered through a 0.22 μm pore size cellulose filter. Medium was changed every two days until cells were harvested. qPCR, Western blot analysis and immunocytochemistry Total RNA was extracted from cultured cells and cDNA was synthesized by reverse transcription. All qPCR probes were obtained from Applied Biosystems. Western blots were performed with anti-Myc (Santa Cruz, clone A-14 1:1000), and anti-FLAG (Sigma, 1:2000) antibody. For immunocytochemistry, cells were fixed in 4% paraformaldehyde and incubated with primary antibodies: anti-GFP (Torrey Pines Biolabs 1:400), anti-cTnT (Thermo Scientific 1:400), anti-Myc (Santa Cruze, clone A-14 1:200), anti-P4HB (Protein-Tech, 1:200), and anti-α-actinin (Sigma, 1:400). After washing with PBS, Alexa fluorogenic secondary antibodies (Invitrogen) were used to detect the signal.

DNA Microarray.

Total RNA was isolated from uninfected CFs, CFs transduced with either empty vector or GHMT retroviruses and adult heart. Microarray analysis was performed on the platform of illumina Mouse-6 Beadchip by the DNA Microarray Core Facility at University of Texas Southwestern Medical Center. Data were analyzed using GeneSpring GX software (Agilent).

Flow Cytometry Analysis.

For the initial assay to detect αMHC-GFP expression, adherent cells were washed with PBS and detached from culture dish by treatment with accutase (Millipore) for 10 min at 37° C. Cells were then washed with 2% FBS in PBS and filtered through a cell strainer. Cells were incubated with propidium iodide (1:1000 dilution in 1% FBS in PBS) for 15 min at room temperature. Dead cells were excluded by propidium iodide staining and live cells were analyzed for GFP expression using FACS Caliber (BD Sciences) and FlowJo software. For intracellular staining for cardiac specific markers, cells were fixed with 4% paraformaldehyde for 15 min after being harvested as described above. Fixed cells were washed with PBS and permeabilized with saponin for 10 min at room temperature. After being washed with PBS, cells were incubated with 5% goat and donkey serum in PBS at room temperature for 30 min followed by incubation with primary antibodies (rabbit polyclonal anti-GFP antibody (Invitrogen) at a 1:100 dilution and mouse monoclonal anti-cTnT antibody (Thermo Scientific) at a 1:400 dilution in 0.2% goat and donkey serum in PBS) for 30 min at room temperature. After being washed with PBS twice, cells were incubated with secondary antibodies for 30 min at room temperature. Secondary antibodies were goat anti-rabbit Alexa fluor 488 (Invitrogen) at a 1:200 dilution and donkey anti-mouse Cy5 (Jackson Laboratory) at a 1:400 dilution in PBS containing 0.2% goat and donkey serum. Cells were washed with PBS three times, and then analyzed for GFP and cTnT expression using FACS Caliber (BD sciences) and FlowJo software.

Sorting of TCF21-Expressing Cells and Gene Expression.

Three month-old Tcf21iCre/+: R26RtdT mice were induced with 0.2 mg/gm tamoxifen for 3 consecutive days by gavaging and a week later, hearts were isolated and processed (atria and aorto-pulmonary trunk were removed) to generate single cell suspension for FACS sorting as described previously (Russell et al., 2011). The suspension was filtered through tissue strainers, centrifuged at 400 g for 5 minutes and resuspended in 10% CM media (10% Hyclone FBS, 3:1 DMEM/M-199, 1% 1 mol/L HEPES, 1.2% antibiotic/antimycotic) before sorting with a MoFlo flow cytometer (Cytomation Inc) using Summit software. For transcript analysis, sorted cells were collected into lysis buffer for RNA extraction (RNAqueous Micro kit from Ambion). A fraction of each sample was also collected into PBS for post sort assessment of purity. Complimentary DNA was synthesized using Superscript III reverse transcriptase (Invitrogen) and random hexamers (Roche). Gene expression profiles were generated using standard qPCR methods with iTAQ SYBR Green master mix (Bio-Rad) on a CFX96 instrument (Bio-Rad). Samples were run in triplicate and normalized to cyclophilin expression. Fold enrichment was determined with respect to the unsorted population.

MI-Surgery and Intramyocardial Injection of Retroviruses.

Mice were anesthetized with isoflurane, intubated with a polyethylene tube (size 60), and then ventilated with a volume-cycled rodent respirator with a 2-3 ml/cycle at a respiratory rate of 120 cycles/min. Thoracotomy was performed at the third intercostals space and self-retaining microretractors were placed to separate the third and fourth rib to visualize the LAD. A 7.0 prolene suture (Ethicon, Johnson & Johnson, Brussels, Belgium) was then passed under the LAD at 1.5 mm distal to the left atrial appendage, immediately after the bifurcation of the left main coronary artery. The LAD was doubly ligated. The occlusion was confirmed by the change of color (becoming paler) of the anterior wall of the left ventricle. Sham-operated mice underwent the same procedure without ligation. Immediately after ligation of the LAD, 50 μl of concentrated retrovirus were injected into the border zone of MI at 5 different areas using a gastight 1710 syringe (Hamilton). The chest wall was then closed with a 5.0 Dexon absorbable suture (Tyco Healthcare, United States Surgical, USA), and the skin was closed with Topical Tissue Adhesive (Abbott Laboratory, IL, USA). Mice were extubated and allowed to recover from surgery under a heating lamp. The mouse surgeon was blinded to the study. Mice with FS>30% 1 day post-MI were removed from the study.

Transthoracic Echocardiography.

Cardiac function was evaluated by two-dimensional transthoracic echocardiography on conscious mice using a VisualSonics Vevo2100 imaging system. Fractional shortening (FS) and ejection fraction (EF) were used as an index of cardiac contractile function. M-mode tracings were used to measure LV internal diameter at end diastole (LVIDd) and end systole (LVIDs). FS was calculated according to the following formula:

FS (%)=[(LVIDd−LVIDs)/LVIDd]×100

EF is estimated from (LVEDV-LVESV)/LVEDV 100%. Left ventriclular end systolic, LVESV; end diastolic volume, LVEDV. All measurements were performed by an experienced operator blinded to the study.

Cardiac MRI.

Six and twelve weeks after MI, the cardiac function of mice was re-evaluated by cardiac MRI using a 7T small animal MR scanner (Varian, Inc, Palo Alto, Calif.) with a 38 mm birdcage RF coil. Under anesthesia by inhalation of 1.5-2% isoflurane mixed in with medical-grade air via nose-cone, the animals were placed prone on a mouse sled, (Dazai Research Instruments) equipped with a pneumatic respiratory sensor and ECG electrodes for cardiac sensing, head first with the heart centered with respect to the center of the RF coil. The mouse chests were shaved and a conducting gel was applied to optimize ECG contact between electrodes and mouse. All MRI acquisitions were gated using both cardiac and respiratory triggering. The bore temperature was kept at 35° C. to assure adequate and constant heart rate. Two-dimensional (2D) gradient echo images on three orthogonal planes (transverse, coronal and sagittal) were acquired to determine the long-axis of the heart in each mouse. Axial images perpendicular to the long axis of the heart were chosen for cine-imaging. Cine images at 12 phases per cardiac cycle was obtained with an echo time of 2.75 ms, repetition time=EKG R-R interval/12, flip angle of 45°, and NEX=4. Each scan consisted of seven to ten contiguous slices from apex to LV outflow with 1 mm thickness, a matrix size of 128×128, and a field of view of 30×30 mm. Epicardial and endocardial borders were manually traced for calculation of left ventriclular end systolic and end diastolic volume (LVESV, LVEDV) using NIH ImageJ software. Total LV volumes were calculated as the sum of all slice volumes. Stroke volume was calculated by the equation, LVEDV-LVESV. EF was calculated by the equation, (LVEDV-LVESV)/LVEDV 100%. Investigators performing MRI acquisition and analysis were blinded to the assignment of mice group.

Induction of Cre by Tamoxifen Administration.

Tamoxifen (Sigma) was dissolved in sesame oil (90%) and ethanol (10%) at a concentration of 50 mg/ml. To induce Cre activity, tamoxifen (0.2 mg/g body weight) was administered by gavage with a 22-gauge feeding needle into mice bearing Tcf21iCre/+:R26RtdT or αMHC-MerCreMer (Sohal et al., 2001); Rosa26-LacZ for three to five or seven consecutive days, respectively. Mice were analyzed or subjected to MI surgery at day 8 post-oral gavage of the last dosage.

Isolation of Adult Mouse Cardiomyocytes, Measurement of Cardiomyocyte Sarcomere Shortening and $Ca^{2+}$ Transients.

Mouse cardiomyocytes were isolated using enzymatic digestion and mechanical dispersion methods previously described21. In brief, after retrograde perfusion with $Ca^{2+}$-free Krebs-Ringer buffer (KR, 35 mM NaCl, 4.75 mM KCl, 1.19 mM $KH_2PO_4$, 16 mM $Na_2HPO_4$, 134 mM sucrose, 25 mM $NaCO_3$, 10 mM Glucose, 10 mM HEPES, pH 7.4, with NaOH) and following collagenase solution (Collagenase I, 8 mg/mL), the LV myocytes were separated using a fine scalpel and scissors. After gentle trituration, cells were kept in KB solution (10 mM Taurine, 70 mM Glutamic acid, 25 mM KCl, 10 mM $KH_2PO_4$, 22 mM Glucose, 0.5 mM EGTA, pH 7.2 with KOH) and studied within 6 hrs at room temperature. To examine myocyte contractile capacity, isolated cardiomyocytes were incubated with 33 μm C12FDG for 30 mins. The green C12FDG+ cardiomyocytes were identified by a fluorescence microscope. Adult cardiomyocytes from wild type mice incubated with C12FDG were used to determine autofluorescence of cardiomyocytes. C12FDG+ cardiomyocytes and C12FDG− cardiomyocytes were field stimulated at 1 Hz while being superfused with extracellular buffer at room temperature. Images were acquired at 240 Hz through a ×60 microscope objective using a variable field rate CCD camera (IonOptix, Milton, Mass.). Cell length was measured by a video edge-detection system, using an IonOptix interface system. Real-time Fourier analyses of images of cardiomyocytes were performed to measure their sarcomere lengths and contraction profiles. The traces were recorded at steady-state conditions. These were achieved normally after 5 min of stimulation. Only rod-shaped, clearly striated cardiomyocytes that were $Ca^{2+}$ tolerant were used in the experiments. Intracellular $Ca^{2+}$ transients were measured as previously described (Tandan et al., 2009; Laugwitz et al., 2005; Luo et al., 2005; Grynkiewicz et al., 1985). Cells are loaded with 5 μM fura-2-acetoxymethyl ester (Fura-2 AM) in extracellular buffer (140 mM NaCl, 5 mM KCl, 1.8 mM $CaCl_2$, 1 mM $MgCl_2$, 10 mM glucose and 10 mM Hepes) containing 0.1% BSA and 1% pyruvate for 30 min at room temperature while shielded from light, then cells are washed with extracellular buffer twice and kept in this buffer with 0.1% BSA and 1% pyruvate until use. Cells are plated on 0.01% polylysine plus 0.1% gelatin coated glass coverslips (Deckglaser, Germany). The glass coverslip is fit in the bottom of a perfusion chamber. The cells are perfused with extracellular buffer at room temperature. Fura-2 fluorescence is measured by illuminating the cells with an alternating 340/380 nm light every 1-2 s. Changes in intracellular $Ca^{2+}$ concentration ($[Ca^{2+}]$) are derived from changes in the ratio of fluorescence intensity at 340 and 380 nm. The fluorescence ratio R=(fluorescence intensity at 340 nm excitation−background intensity at 340 nm excitation)/(fluorescence intensity at 380 nm−background intensity at 380 nm) were calibrated in $[Ca^{2+}]$ using the following equation (Grynkiewicz et al., 1985):

$$[Ca^{2+}] = \frac{K_d * \beta * (R - R_{min})}{(R_{max} - R)}$$

where $R_{min}$ and $R_{max}$ are the ratios obtained, respectively, in the absence of $Ca^{2+}$ (solution devoid of $Ca^{2+}$ and containing 10 mM EGTA, 10 μM ionomycin and 40 μM BAPTA-AM) and at saturating $Ca^{2+}$ (solution containing 2 mM $Ca^{2+}$ and 10 μM ionomycin). Kd=224 nM is the dissociation constant of Fura-2 and =(fluorescence intensity at 380 nm excitation in absence of $Ca^{2+}$/fluorescence intensity at 380 nm excitation at saturating $Ca^{2+}$). Analyses were carried out with the specialized data analysis software (IonWizard, IonOptix Corp.).

Calcium Transient Measurements in Spontaneous Beating Cardiomyocytes.

For calcium imaging, beating iCLMs, cultured neonatal mouse atria myocytes, neonatal mouse ventricular cardiomyocytes, or isolated adult mouse ventricular cardiomyocytes were loaded with 5 μM Fura-2 AM (Invitrogen) together with 0.1% Pluronic F-127 (Invitrogen) in modified Tyrode solution (140 mM NaCl, 5 mM KCl, 1.8 mM CaCl$_2$, 1 mM MgCl$_2$, 10 mM glucose, and 10 mM Hepes, pH 7.4) containing 0.1% BSA and 1% pyruvate for 30 min at 37° C. while shielded from light. Before imaging, the cells were washed and allowed to de-esterify the Fura-2 AM for 30 minutes in Tyrode solution at room temperature as described previously (Luo et al., 2005). Ca$^{2+}$ imaging was performed using the PTI (Photon Technology International) Ca$^{2+}$ Imaging System (Birmingham, N.J.) with an automated fluorescence microscope and a CCD camera. A glass coverslip was inserted into the bottom of a perfusion chamber. The cells were perfused with modified Tyrode solution, and calcium transients in individual spontaneous beating cell were calculated by measurement of Ca$^{2+}$-induced fluorescence at both 340 and 380 nm.

Example 2

Results

A core set of evolutionarily conserved transcription factors (GATA4, HAND2, MEF2, MesP1, Nkx2-5, and Tbx5) controls cardiac gene expression and heart development (Olson, 2006; Wu, 2008). Recently, GATA4, MEF2C, and Tbx5 were reported to be capable of converting fibroblasts to cardiomyocyte-like cells in vitro7. The inventors sought to define the optimal combination of core cardiac transcription factors necessary and sufficient for reprogramming of fibroblasts into beating cardiac-like myocytes and to determine if these factors could restore cardiac function to injured hearts through reprogramming of endogenous cardiac fibroblasts to cardiomyocyte-like cells in vivo. Toward this goal, the inventors generated retroviruses to express each of the six core cardiac transcription factors (GATA4 (G), and HAND2 (H), MEF2C (M), MesP1 (Ms), Nkx2-5 (N), and Tbx5 (T)) in fibroblasts derived from mice bearing a cardiac-specific αMHC-GFP transgene (FIGS. 5A-D and 6).

Figure 7A:
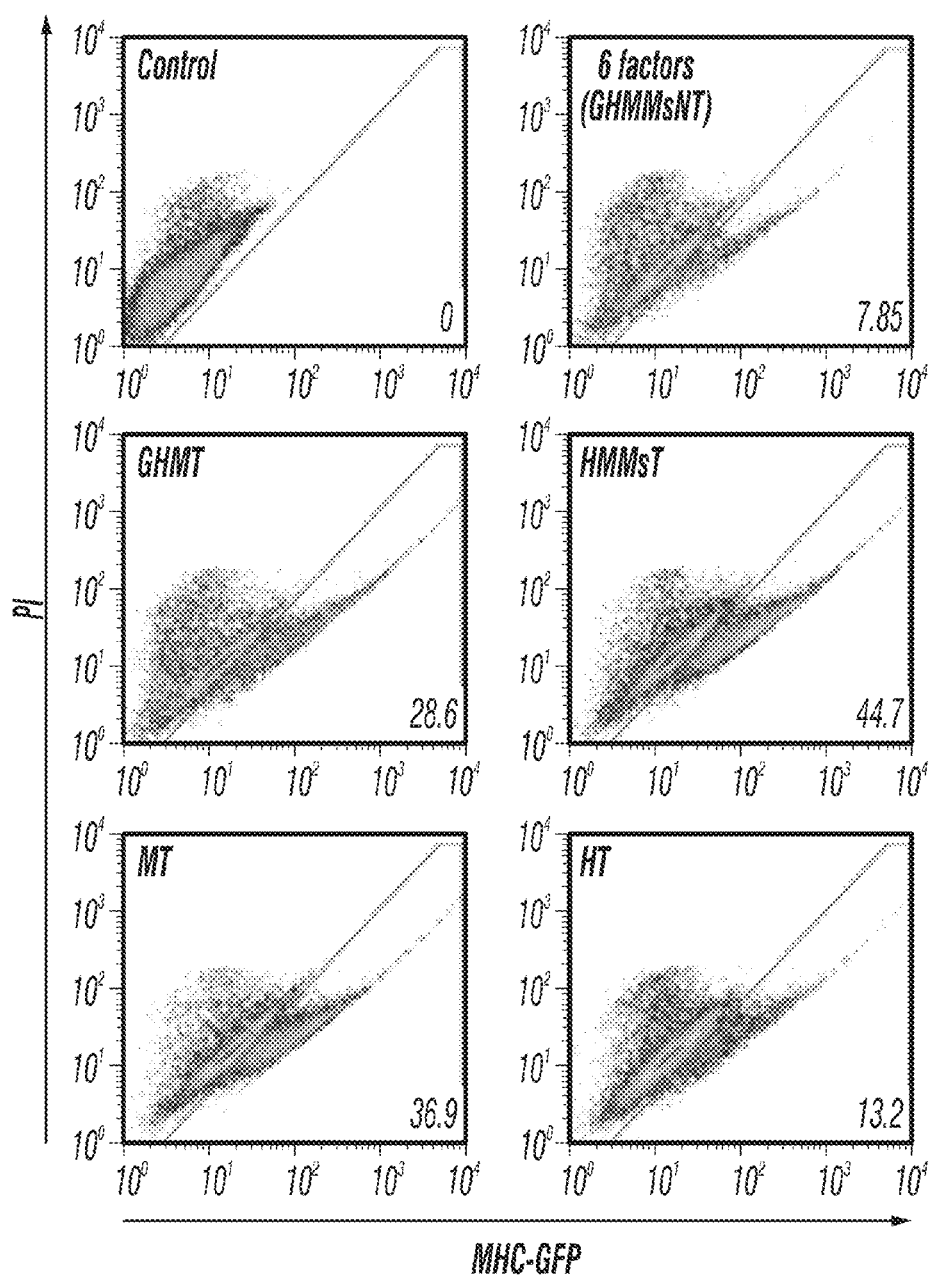
FIGS. 7A-B. Screening for transcription factors able to reprogram adult TTFs toward a cardiac fate.
Figure 7A:
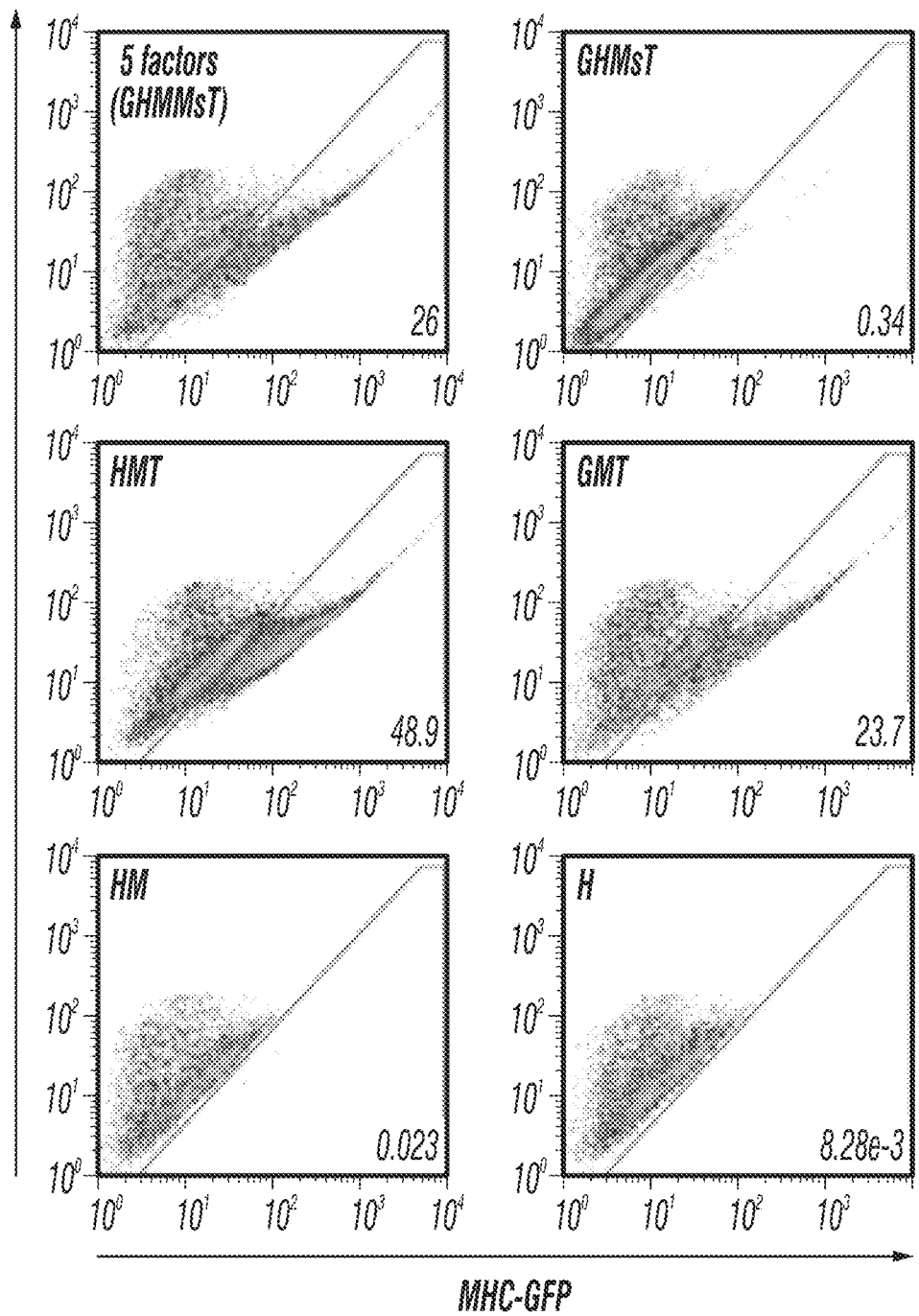
Figure 7A:
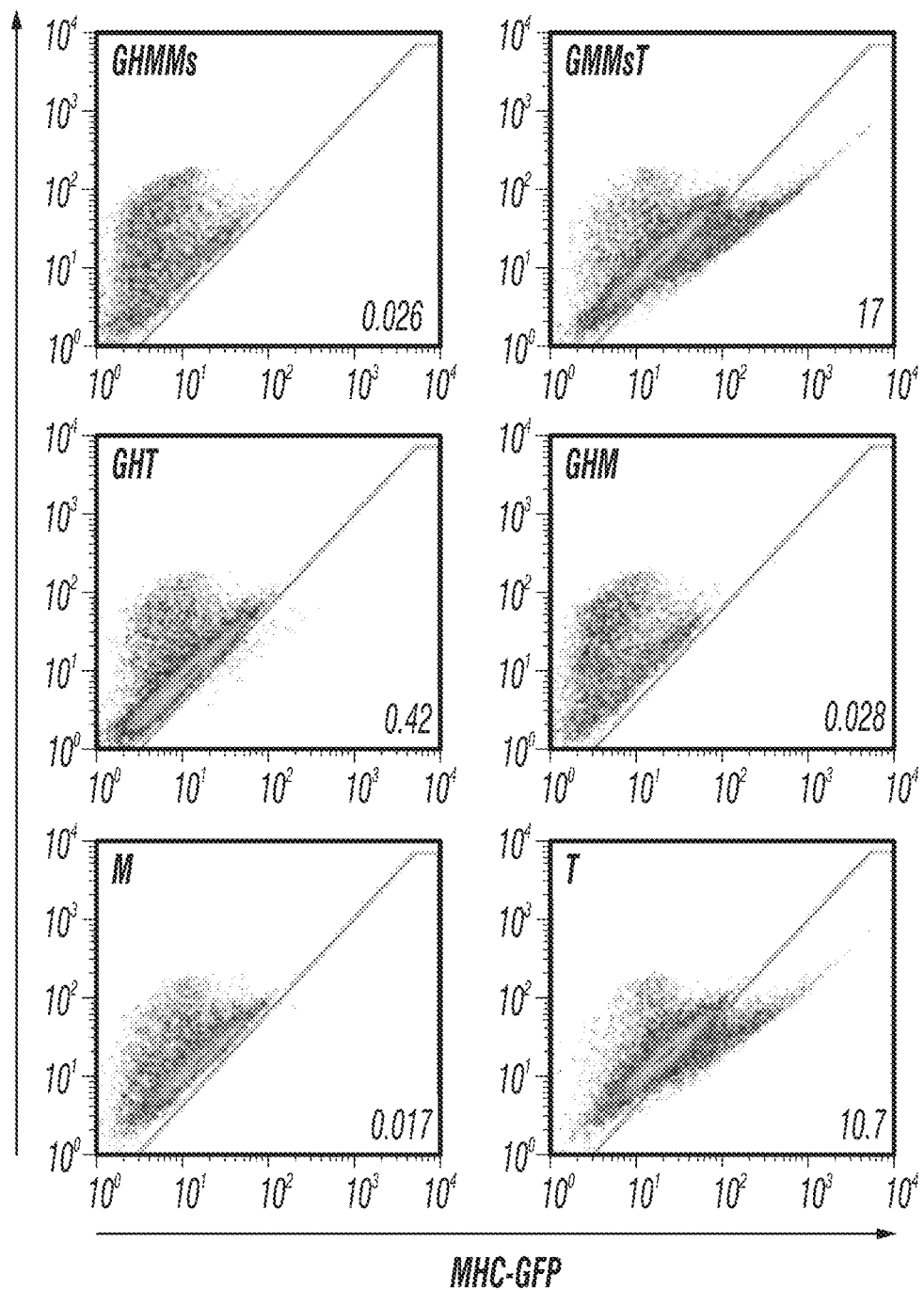
Figure 7B:
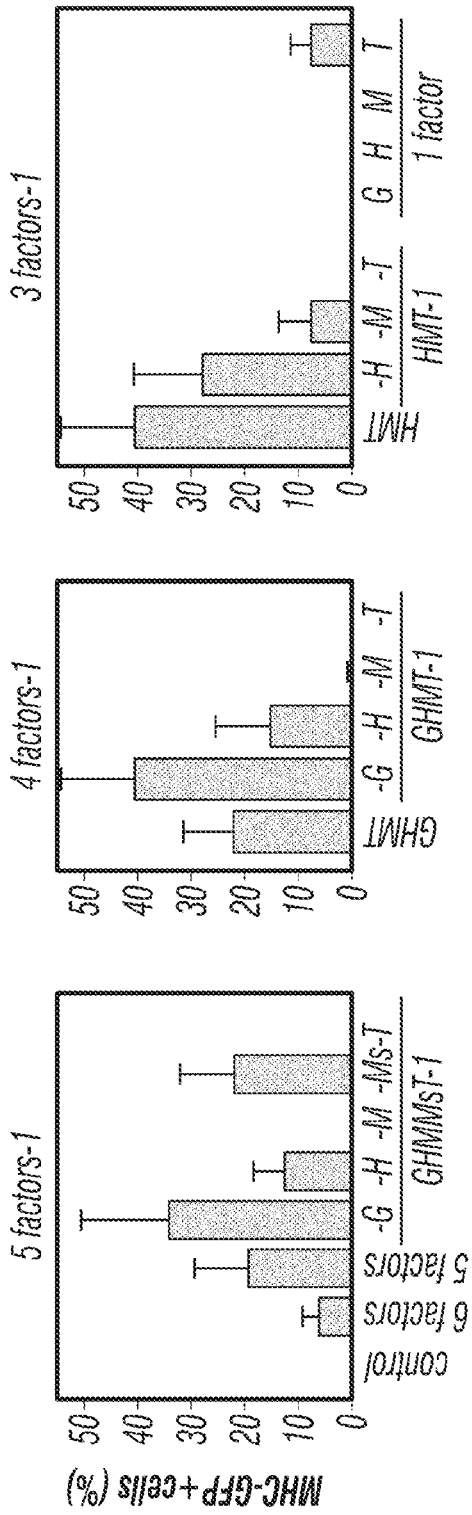

Potential cardiogenic activity of the above 6 factors (G, H, M, Ms, N, T) in adult mouse tail-tip fibroblasts (TTFs) was quantified by analysis of GFP+ cells by flow cytometry after 9 days of transduction. No GFP+ cells were observed in fibroblast cultures transduced with viral backbone or without infection. However, the 6 factors together generated a small population of cells (~6%) positive for GFP (FIGS. 7A-B). After several rounds of withdrawing one factor, the inventors identified multiple combinations, including GHMMsT, GHMT, HMMsT, GMT, HMT, and MT, that were capable of inducing a high percentage of αMHC-GFP+ cells (FIGS. 7A-B). The cooperativity amongst the different factors is consistent with their ability to synergistically activate cardiac gene expression and to activate each other's expression (Olson, 2006; Zang et al., 2004; Dai et al., 2002; Maitra et al., 2009; Ghosh et al., 2009).

Figure 8:
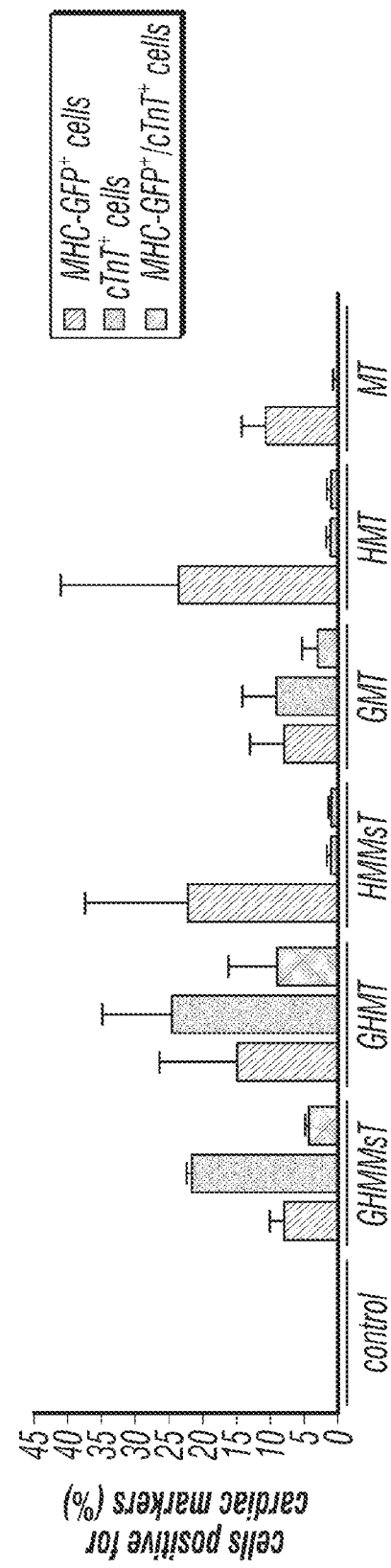
FIG. 8. Analysis of two cardiac markers in cardiac TTFs transduced with cardiac transcription factors. TTFs were infected with retroviruses expressing the indicated combination of transcription factors and analyzed by flow cytometry for single (αMHC-GFP+ or cTnT+) and double (αMHC-GFP+ and cTnT+) cardiac markers. Data are shown as percentage of cells positive for cardiac markers. Three to four independent experiments are presented as mean±std.
Figure 9A:
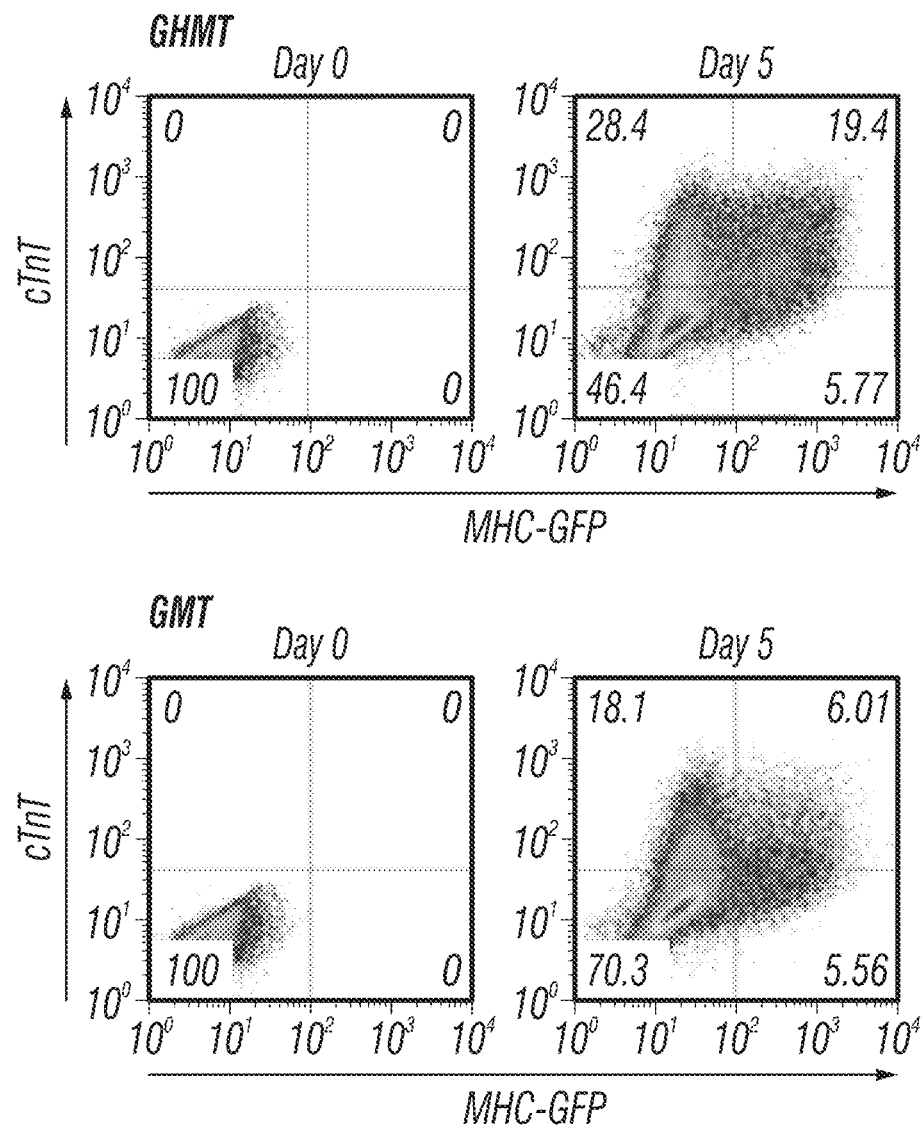
FIG. 9A-B. Time course of cardiac gene activation in response to GHMT.
Figure 9A:
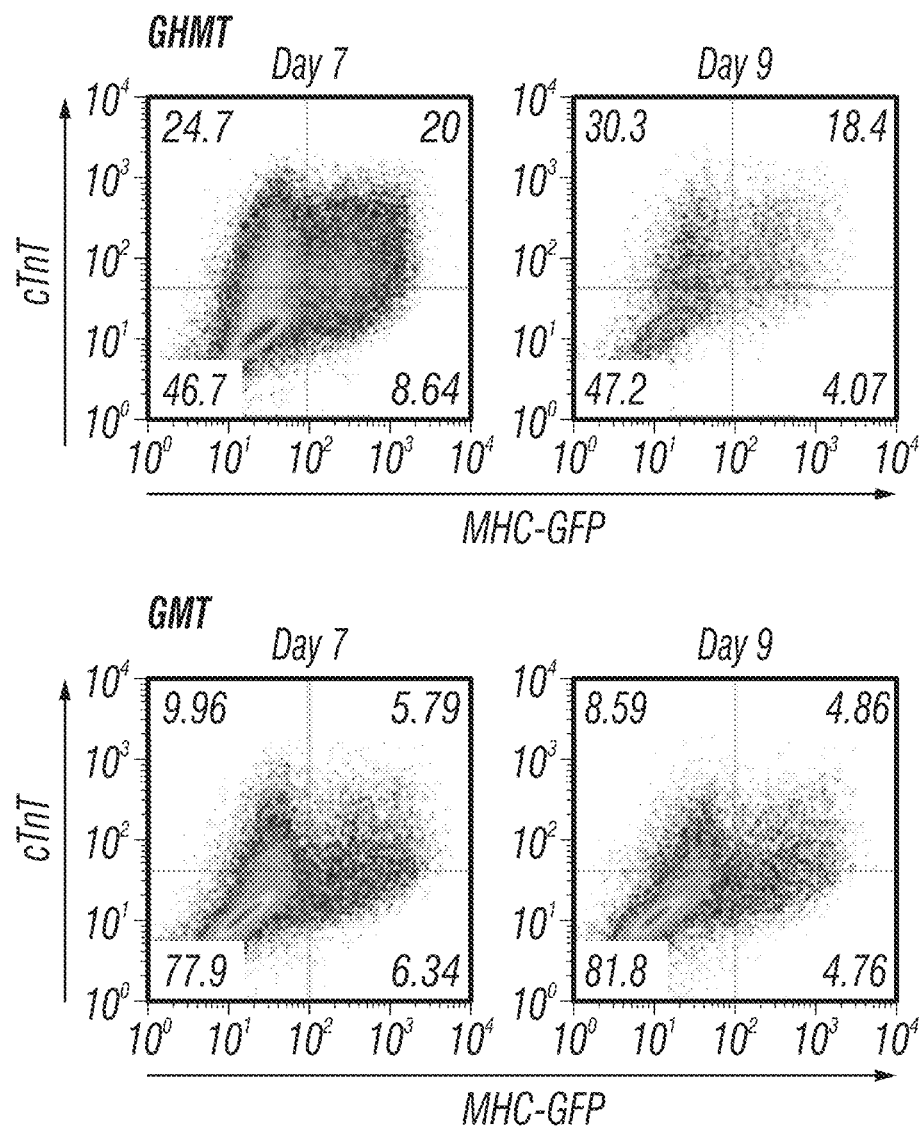
Figure 9A:
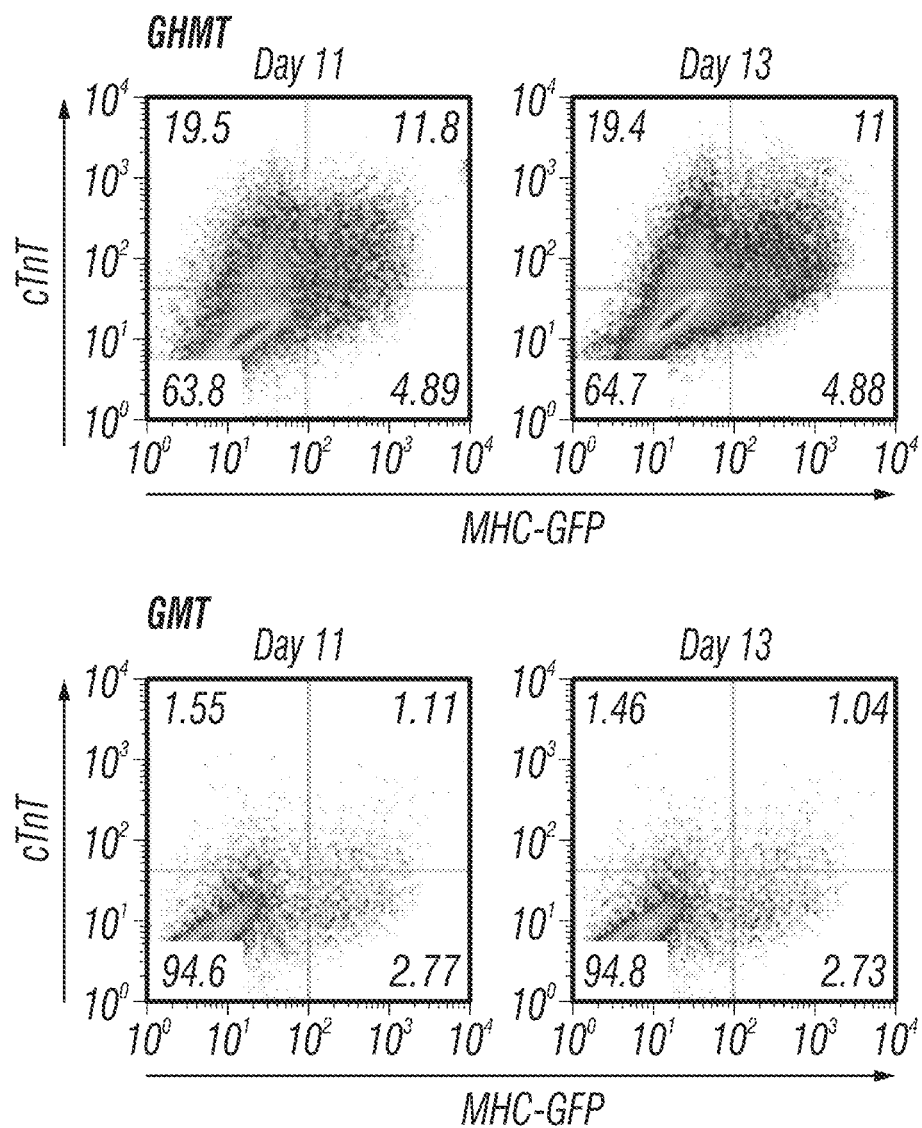
Figure 9B:
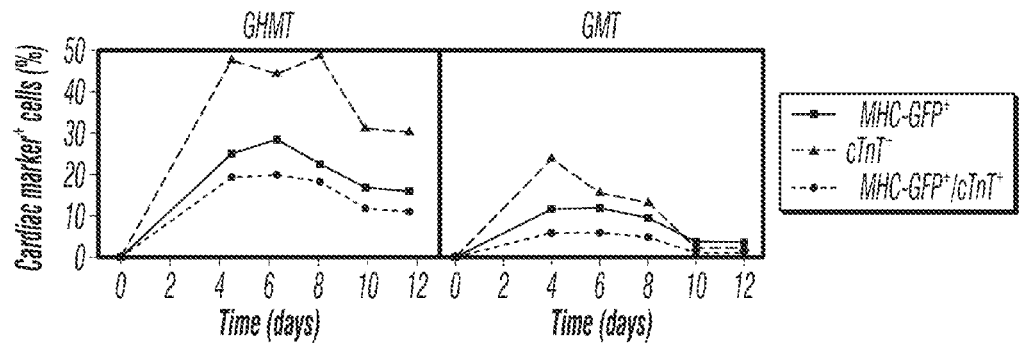

To determine whether the above factor combinations could activate endogenous cardiac-specific genes in adult TTFs, the inventors examined expression of cardiac troponin T (cTnT) and αMHC-GFP by flow cytometry (FIG. 8). GHMT induced ~9.2% of cells to become positive for both αMHC-GFP and cTnT. The inventors refer to cells expressing at least one endogenous cardiomyocyte marker, cTnT or α-actinin, as induced cardiac-like myocytes (iCLMs). By comparison, GMT induced ~2.9% of cells to adopt a cTnT+/αMHC-GFP+ phenotype (FIG. 8). The percentage of cTnT+/αMHC-GFP+ iCLMs generated from adult TTFs by GHMT (9.2%) is ~4-fold higher than previously reported for neonatal TTFs with GMT (2.5%)7. The percentage of cells expressing cTnT and αMHC-GFP reached a peak at day 7 of transduction, and declined with time due to overgrowth of non-reprogrammed fibroblasts (FIGS. 9A-B).

Figure 1B:
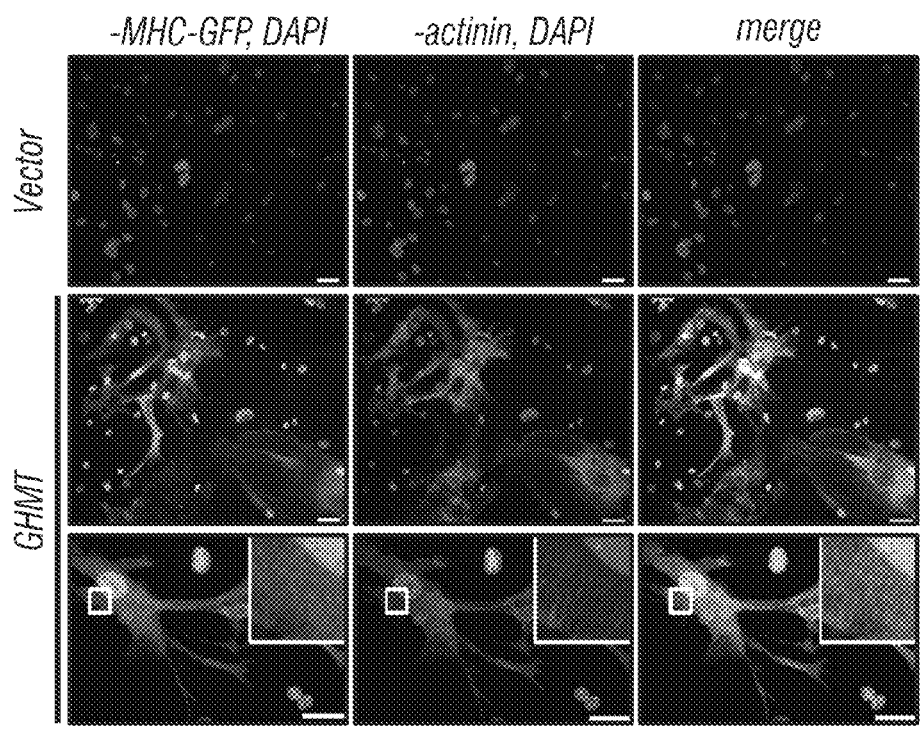
Figure 10A:
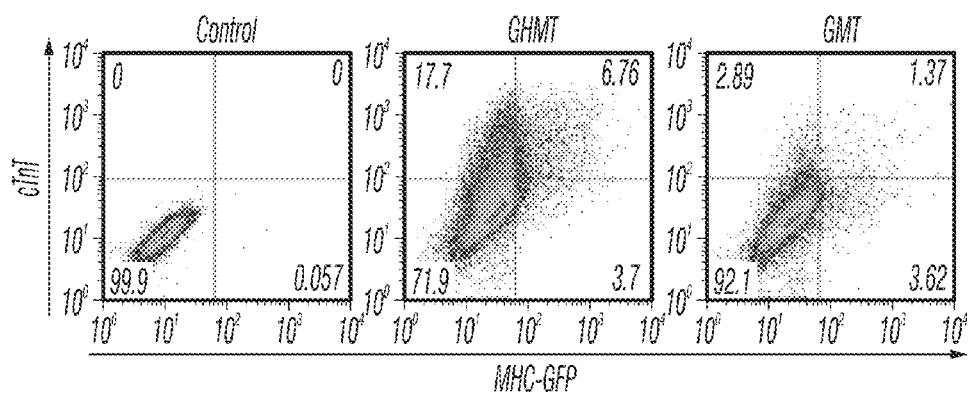
FIGS. 10A-B. Reprogramming adult mouse CFs toward a cardiac phenotype by GHMT.
Figure 10B:
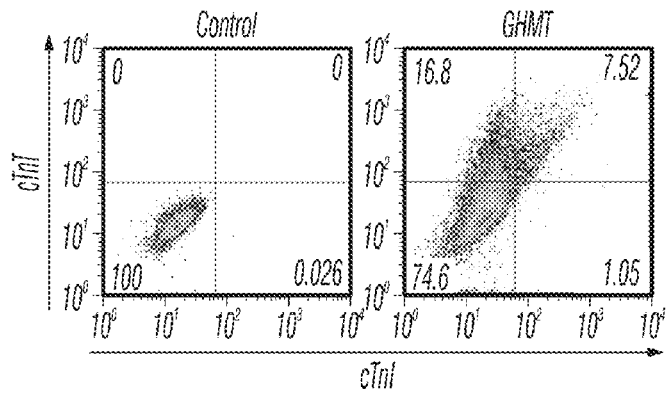
Figure 11:
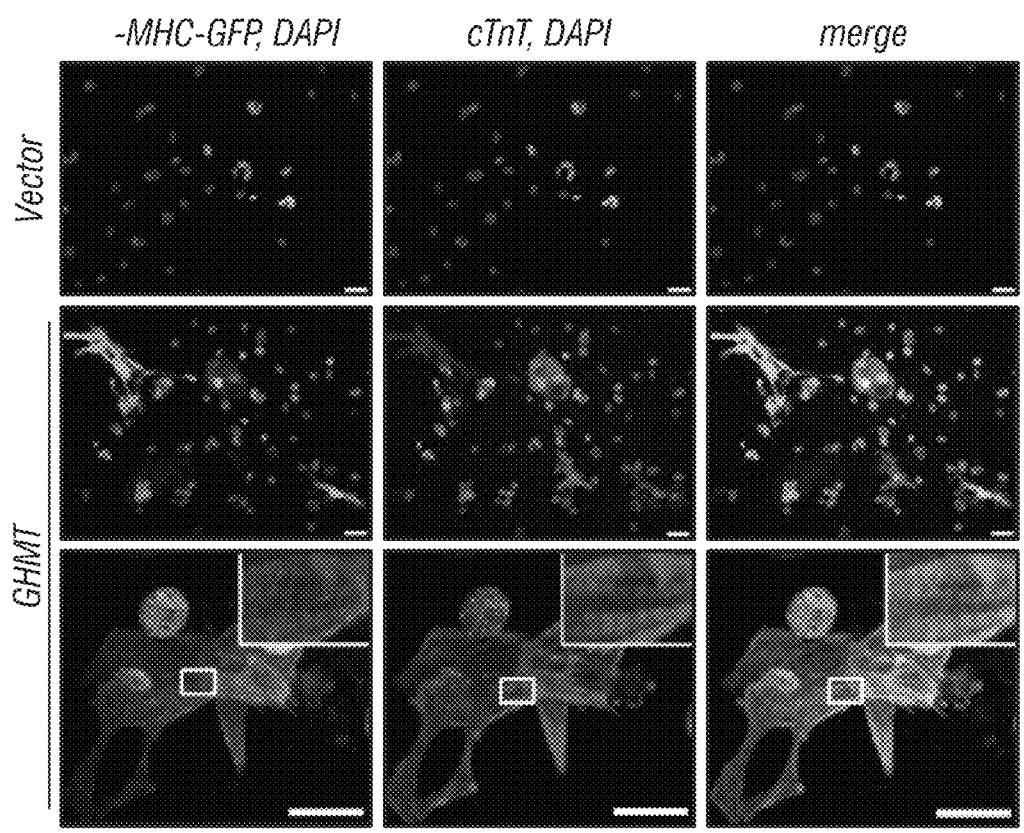
FIG. 11. Induction of cardiomyocyte markers in adult CFs by GHMT. Immunofluorescent staining for αMHC-GFP and cTnT after 14 days of transduction was performed. Adult CFs isolated from αMHC-GFP reporter mice were transduced by retroviruses carrying GHMT or empty vector. Sarcomeric structures were observed (bottom panel). White boxes in lower panels are enlarged in insets. Scale bar, 40 μm.
Figure 12A:
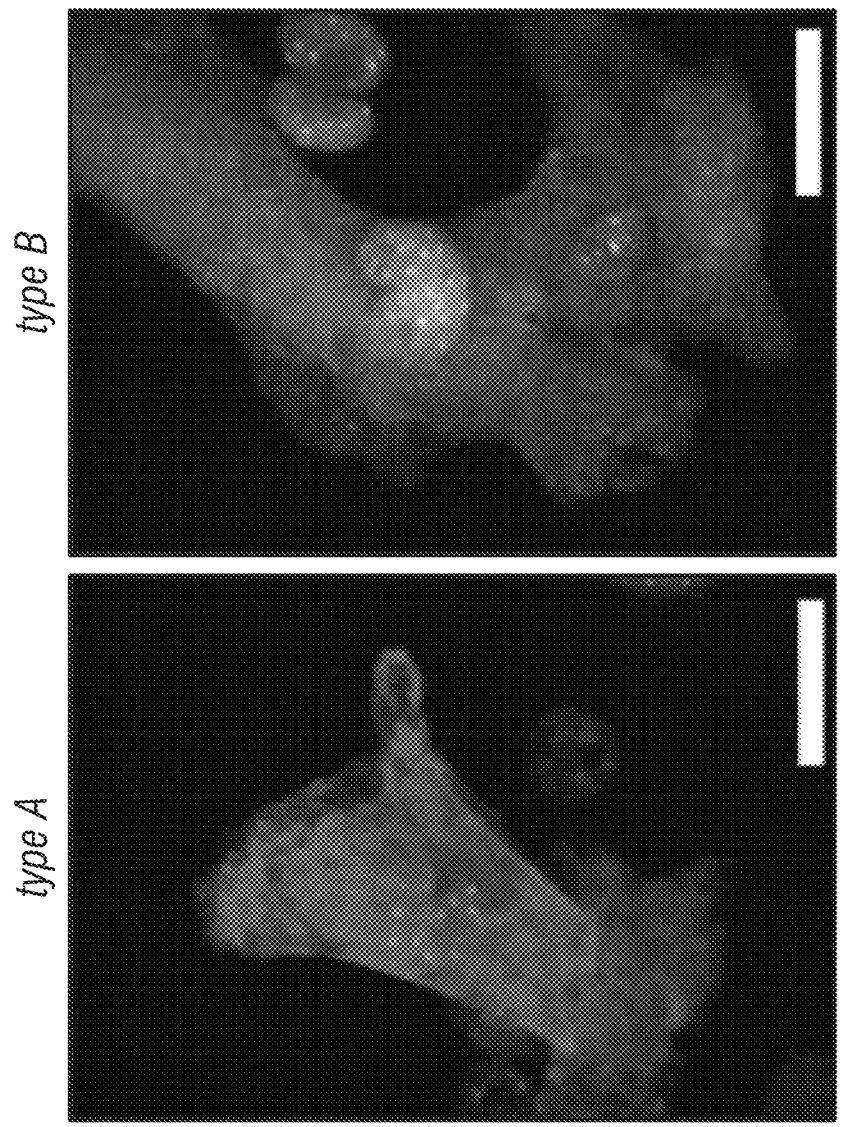
FIGS. 12A-C. Induction of sarcomere-like structures in adult fibroblasts with GHMT.
Figure 12B:
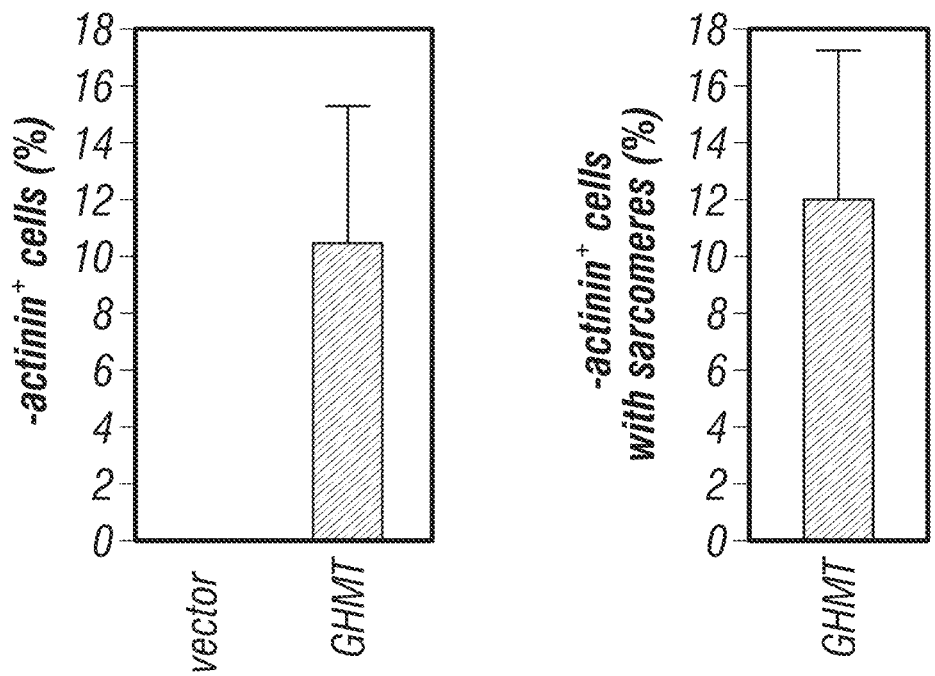
Figure 12C:
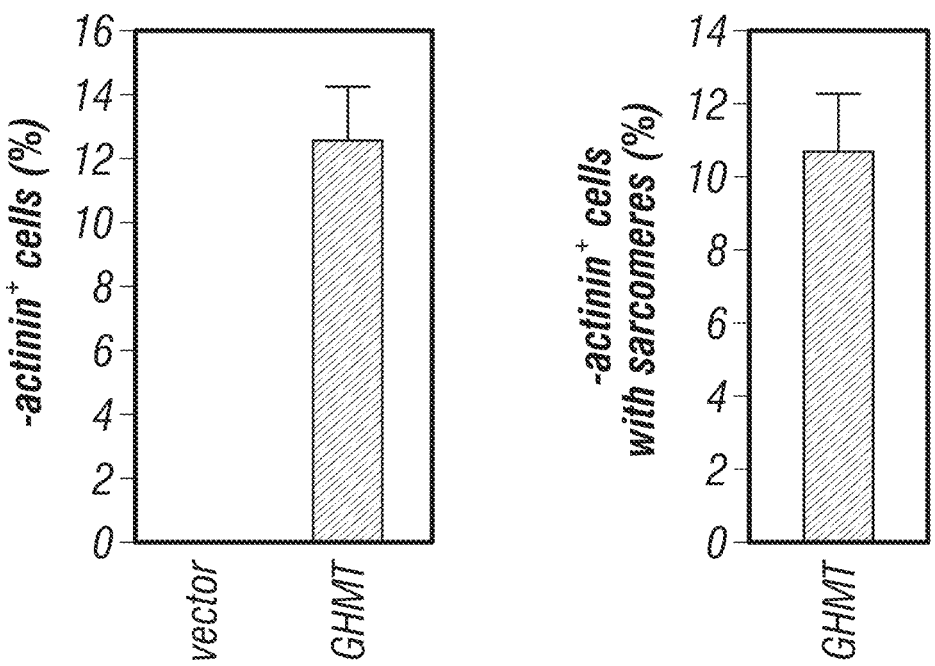
Figure 13A:
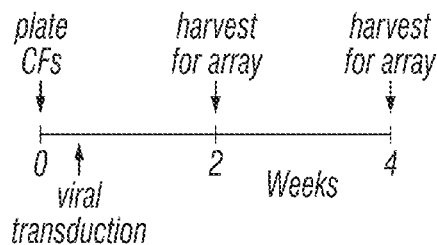
FIGS. 13A-E. Gene expression profile in adult CFs transduced with GHMT.
Figure 13B:
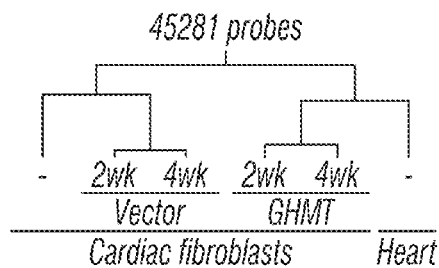
Figure 13D:
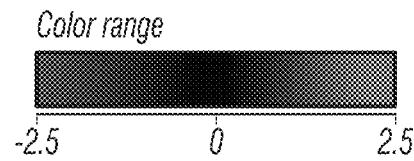
Figure 13C:
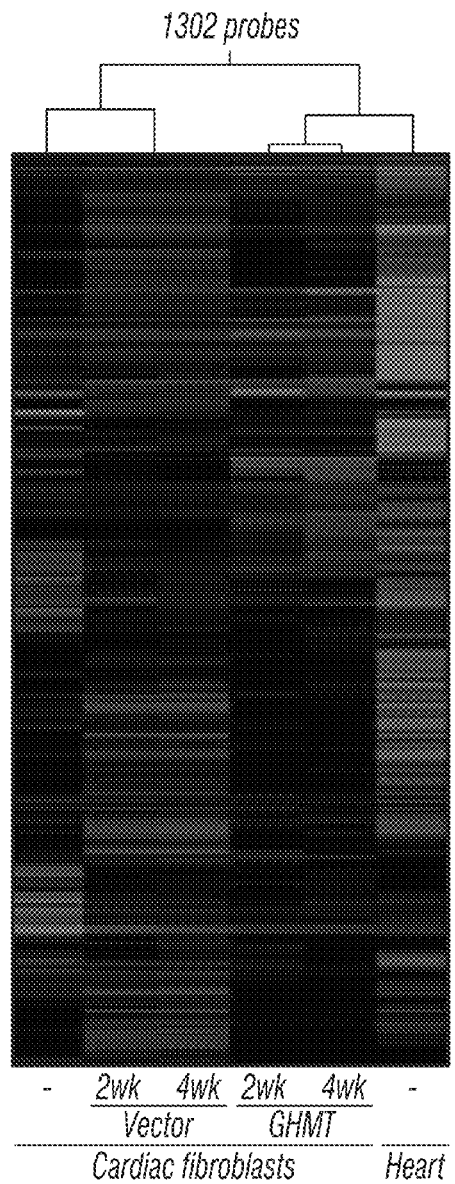
Figure 13E:
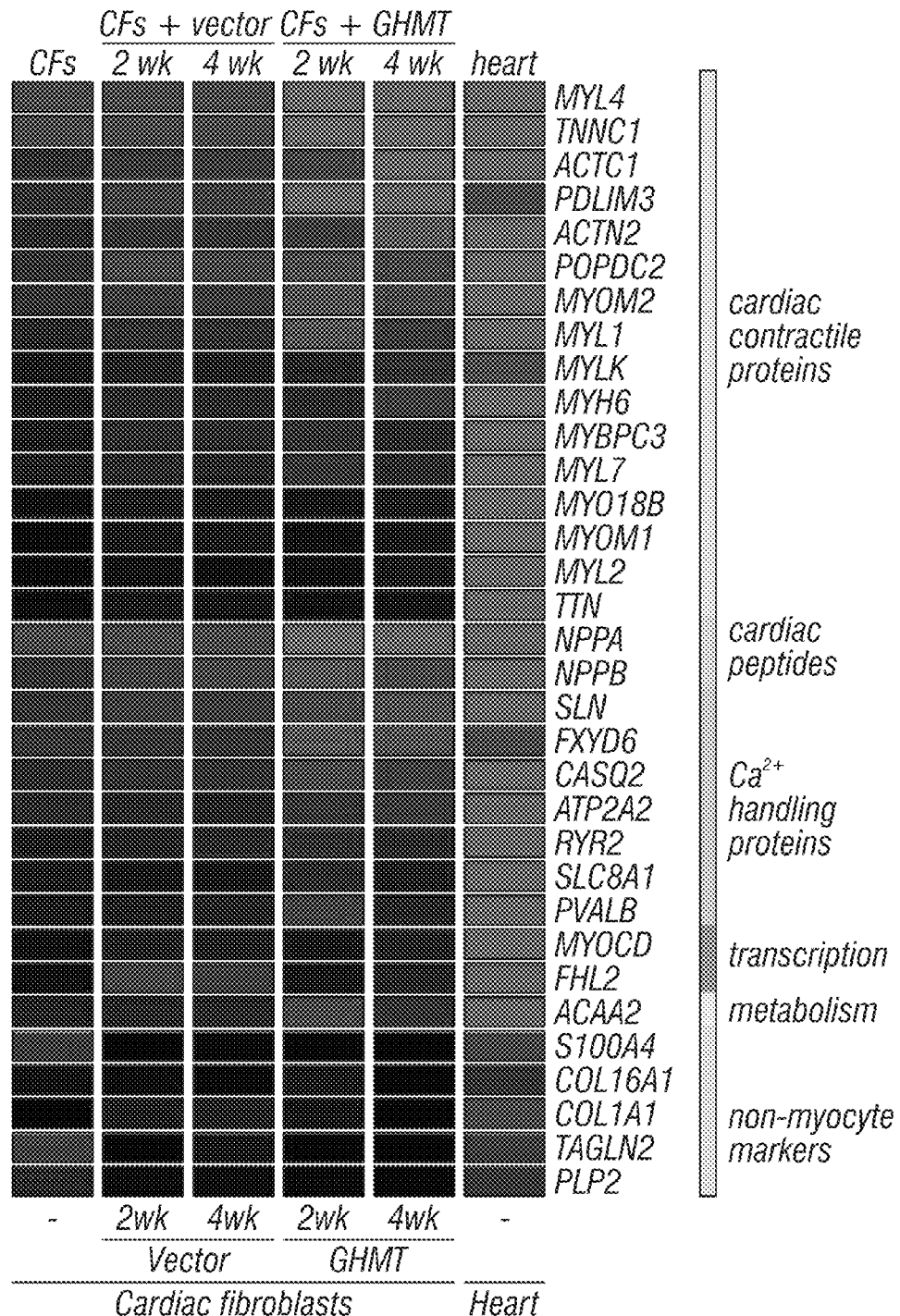
Figure 14A:
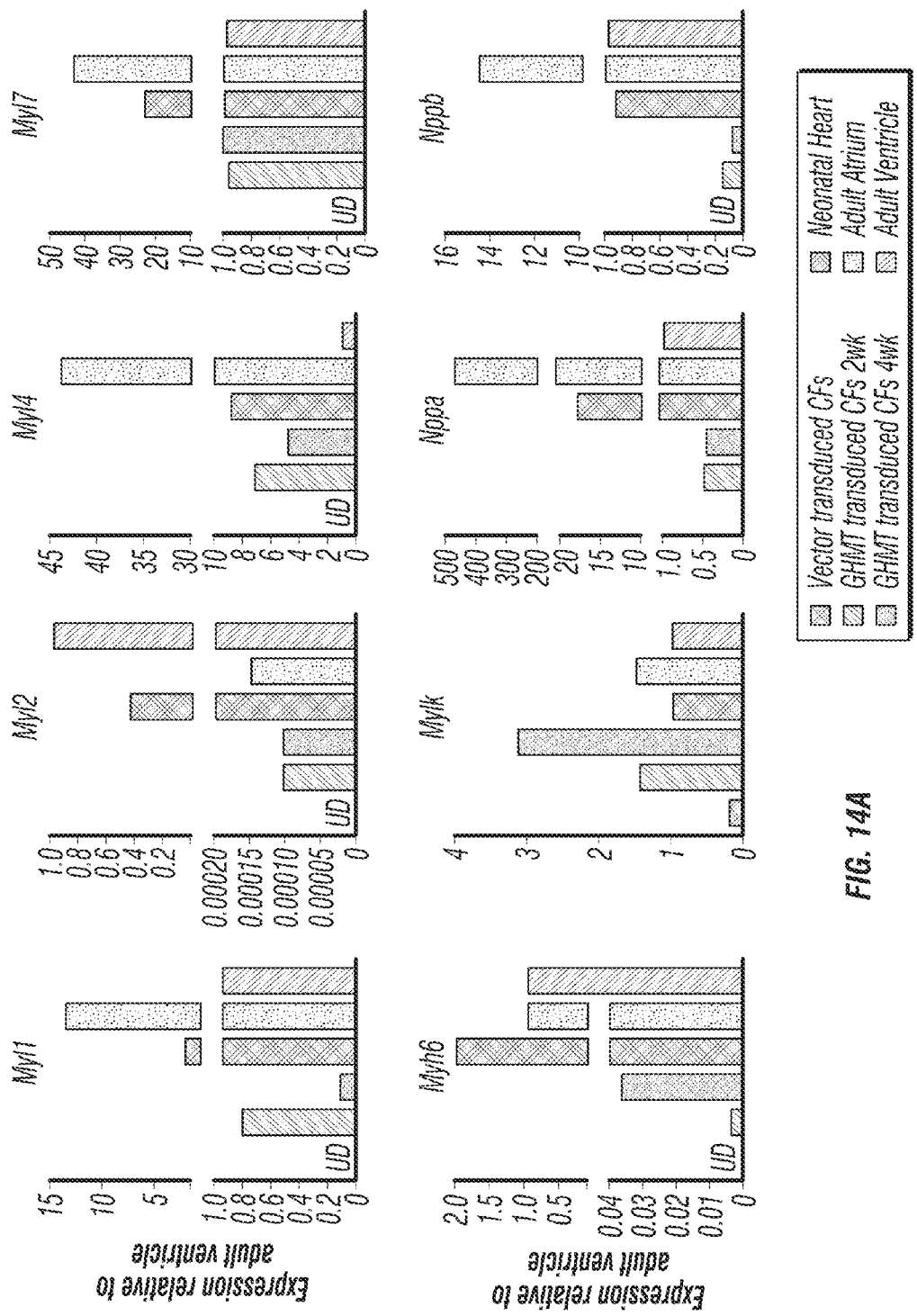
FIGS. 14A-B. Validation of cardiac and fibroblast gene expression by real-time PCR. Expression of (FIG. 14A) cardiac and (FIG. 14B) fibroblast markers was quantified by qPCR. UD undetectable.
Figure 14A:
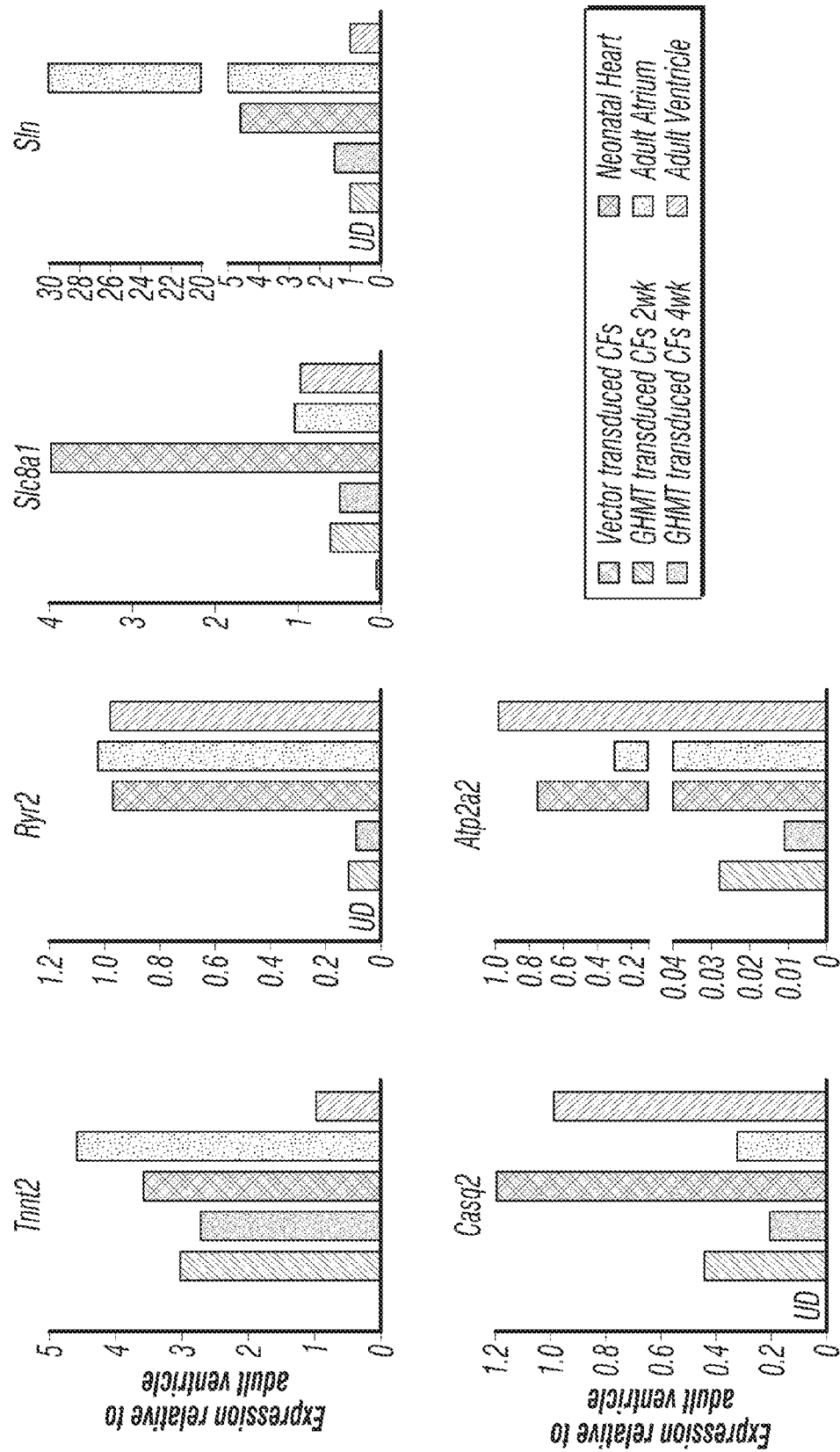
Figure 14B:
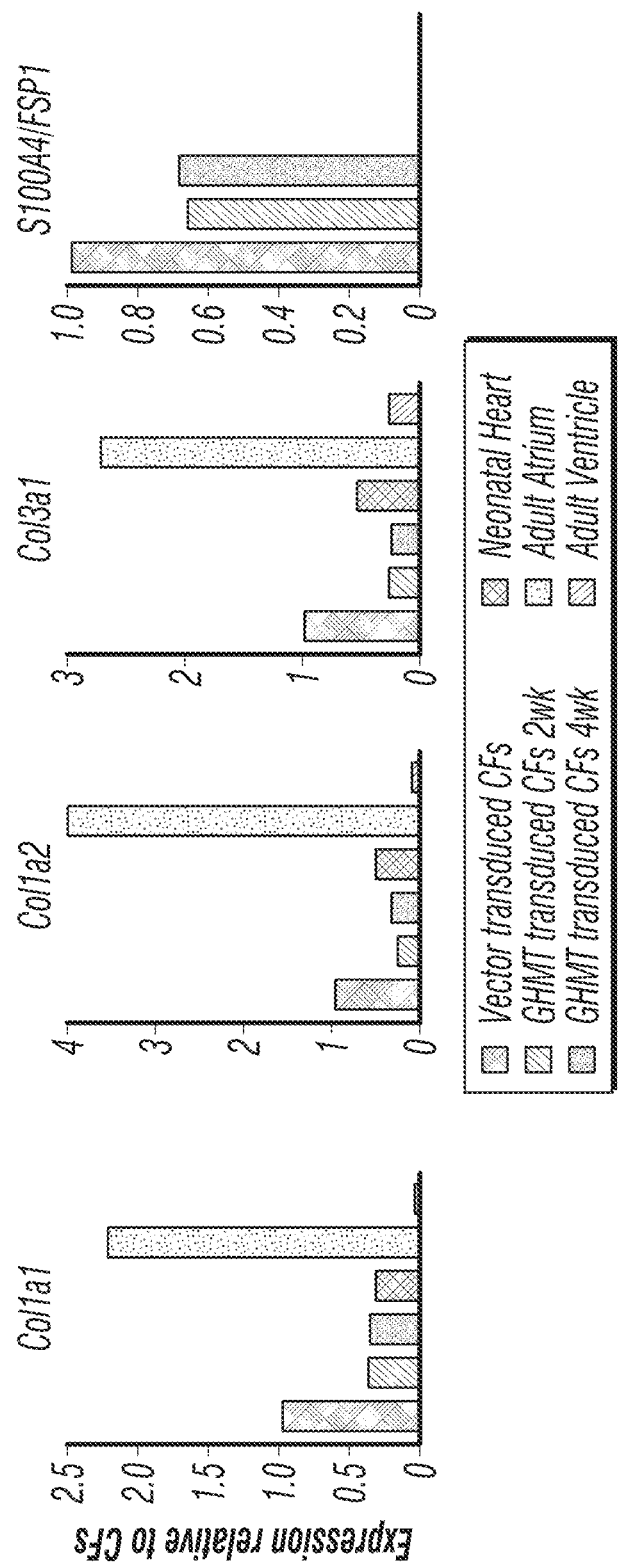
Figure 15A:
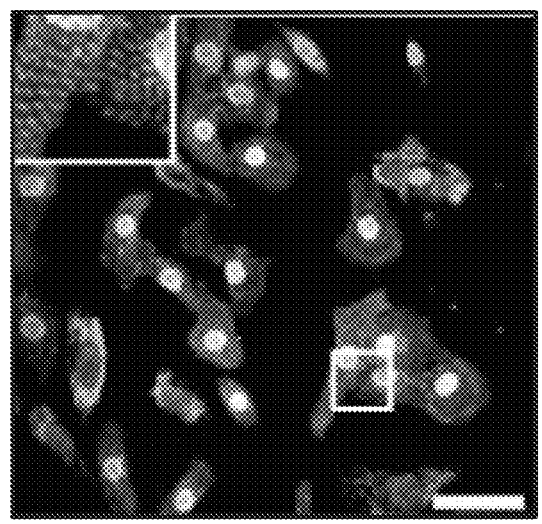
FIGS. 15A-C. Immunostaining for cardiac and fibroblast markers in vitro.
Figure 15B:
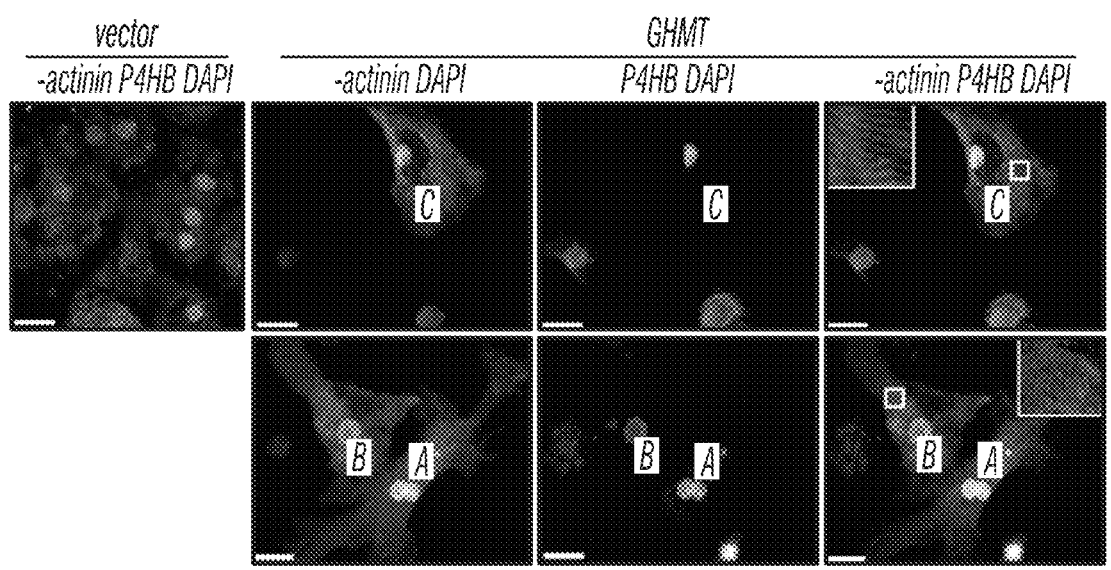
Figure 15C:
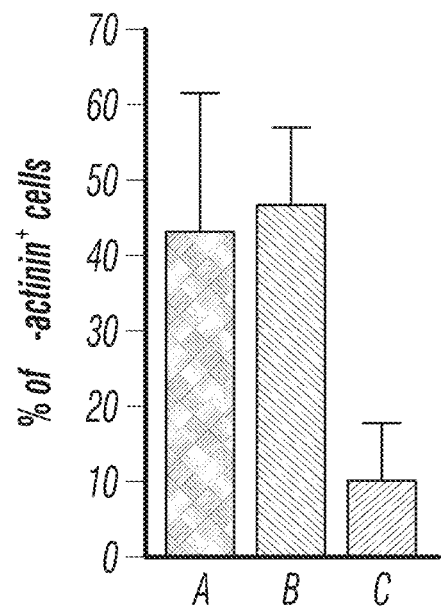

Cardiac fibroblasts (CFs) are the most prevalent interstitial cell type in adult mammalian hearts. To examine whether GHMT could activate cardiac gene expression in CFs, the inventors transduced adult CFs with GHMT, GMT or empty viruses and expression of cardiac markers was analyzed by flow cytometry one week later. GHMT induced 6.8% of CFs to become cTnT+/αMHC-GFP+, compared with 1.4% double-positive cells with GMT (FIG. 10A). GHMT induced cTnT and cTnI (cardiac Troponin I) in 7.5% of cells (FIG. 10B). Thus, GHMT represented the most optimal combination of factors for efficient initiation of cardiac gene expression in adult fibroblasts. αMHC-GFP+ cells derived from adult TTFs and CFs by GHMT transduction showed strong immunostaining of the sarcomeric proteins á-actinin and cTnT (FIGS. 1A-B and 11). In the presence of GHMT, approximately 10% of CFs or 12% of TTFs became α-actinin+ and ~12% or ~10%, respectively, of these displayed organized sarcomere-like structures (FIGS. 12A-C).

Figure 1C:
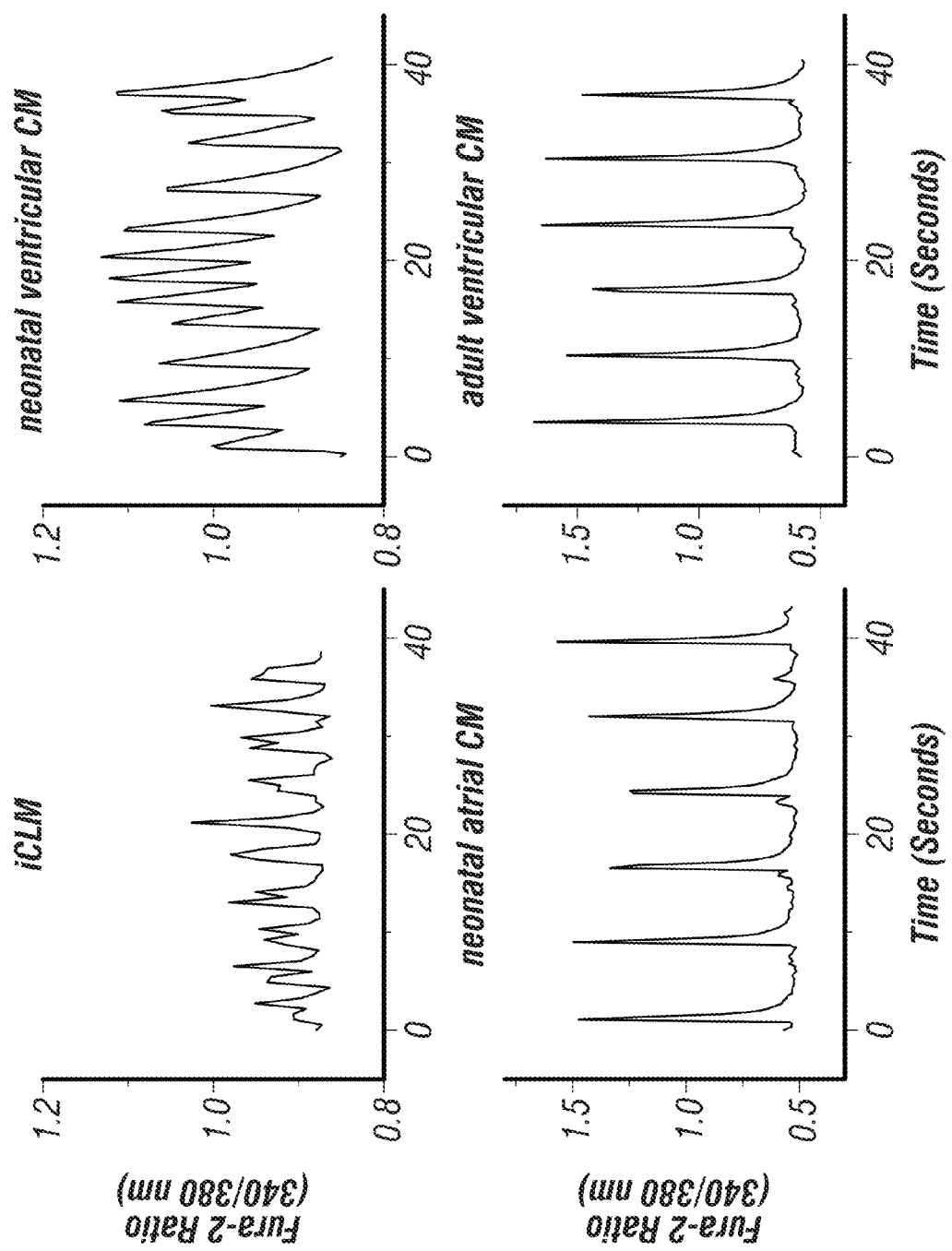
Figure 16:
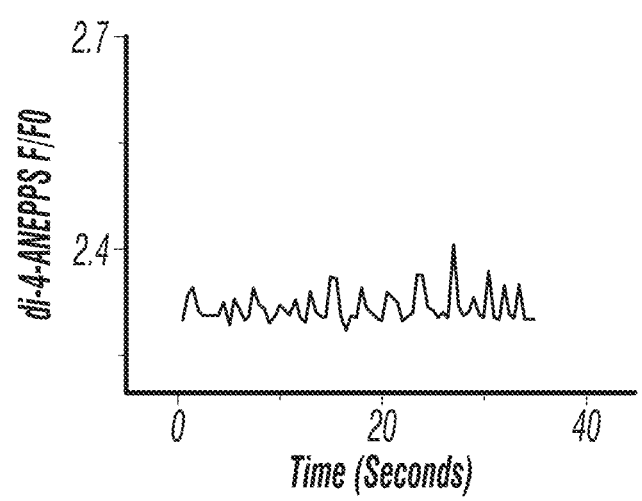
FIG. 16. GHMT reprogrammed adult CFs into functional iCLMs. Representative action potentials recorded spontaneous beating iCLMs using a voltage-sensitive dye di-4-ANEPPS, as described in Methods.
Figure 17A:
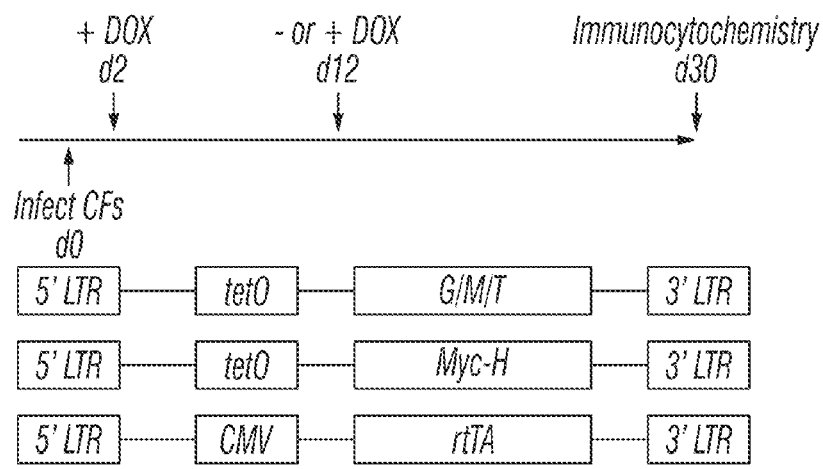
FIGS. 17A-B. Induction of iCLMs from CFs by inducible expression of GHMT.
Figure 17B:
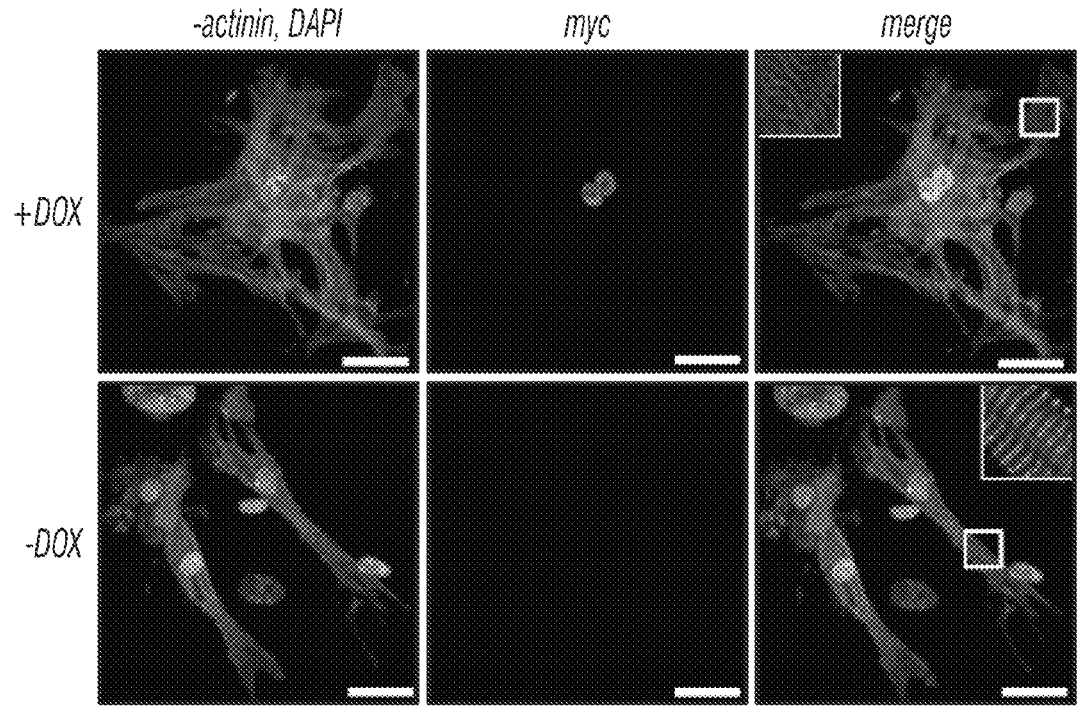

Microarray and qPCR analysis of gene expression patterns showed expression of a broad range of cardiac genes, indicative of a ventricular phenotype, and concomitant suppression of non-myocyte genes including FSP1 (fibroblast-specific protein 1/S100A4) in fibroblasts transduced with GHMT (FIGS. 13A-15C). Following maintenance of GHMT-transduced CFs or TTFs in culture for 5 weeks, the inventors observed spontaneous contractions, calcium transients and action potentials in 0.1%-1% of iCLMS that displayed sarcomeric structures (FIGS. 1C and 16). iCLMs displayed a pattern of calcium transients most similar to neonatal ventricular cardiomyocytes (FIG. 1C). Transduction with inducible expression vectors showed that the cardiomyocyte-like phenotype was stable following termination of exogenous GHMT expression (FIGS. 17A-B).

Figure 1D:
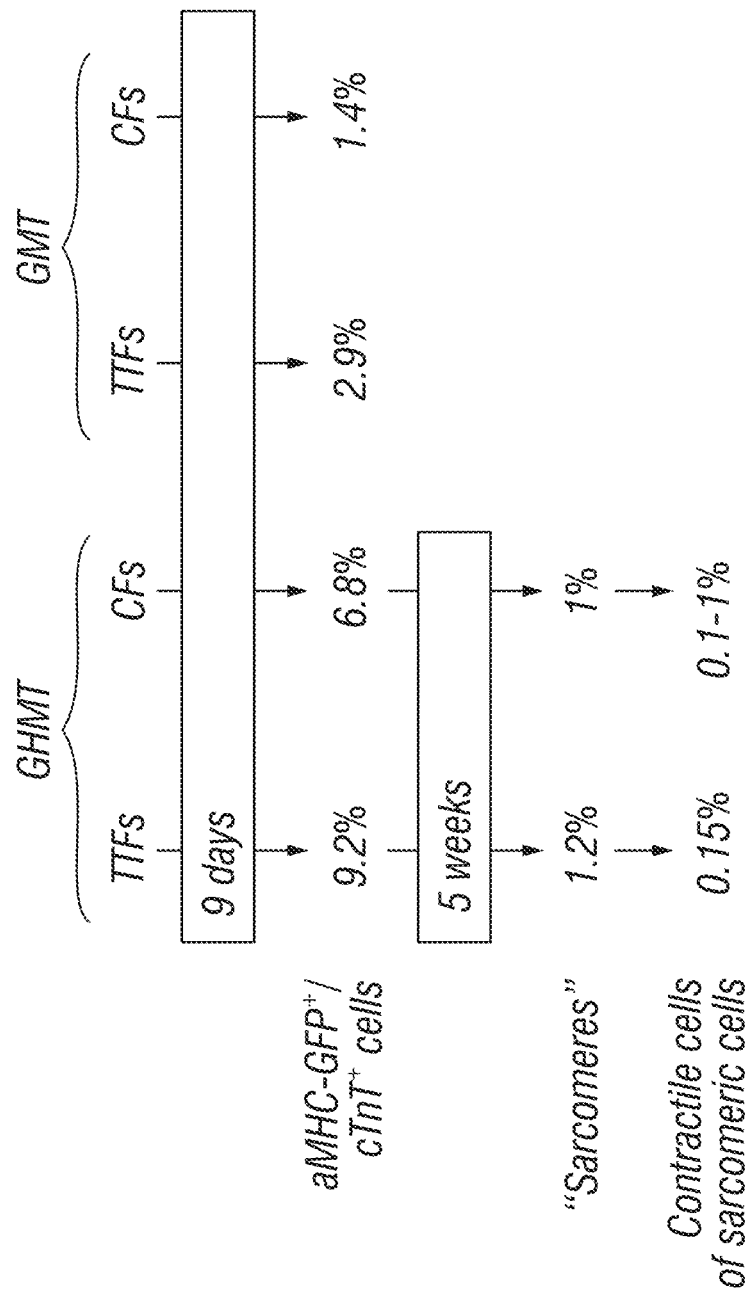

Co-staining for cardiomyocyte markers and Myc-tagged GHMT suggests that induction of the cardiomyocyte-like phenotype by GHMT is cell-autonomous (FIGS. 18A-B). Together, these results indicate that GHMT can activate cardiac gene expression in a sub-population of TTFs and CFs. The relatively small percentage of cells that adopts the cardiac-like phenotype perhaps indicates a precise stoichiometry of the cardiac factors required for phenotypic conversion, which is achieved in only a fraction of cells (FIG. 1D).

Figure 19A:
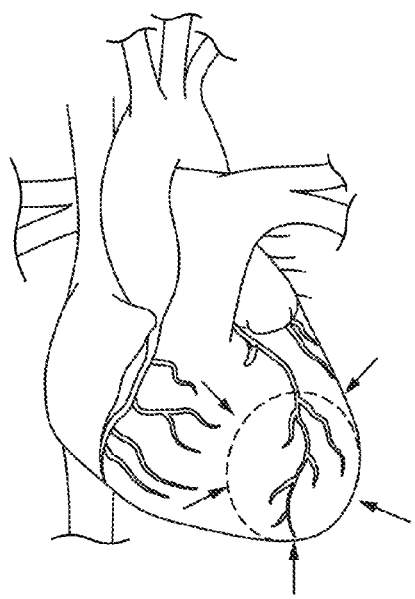
FIGS. 19A-D. Retrovirus infected non-cardiomyocytes in the ischemic area in the injured heart.
Figure 19B:
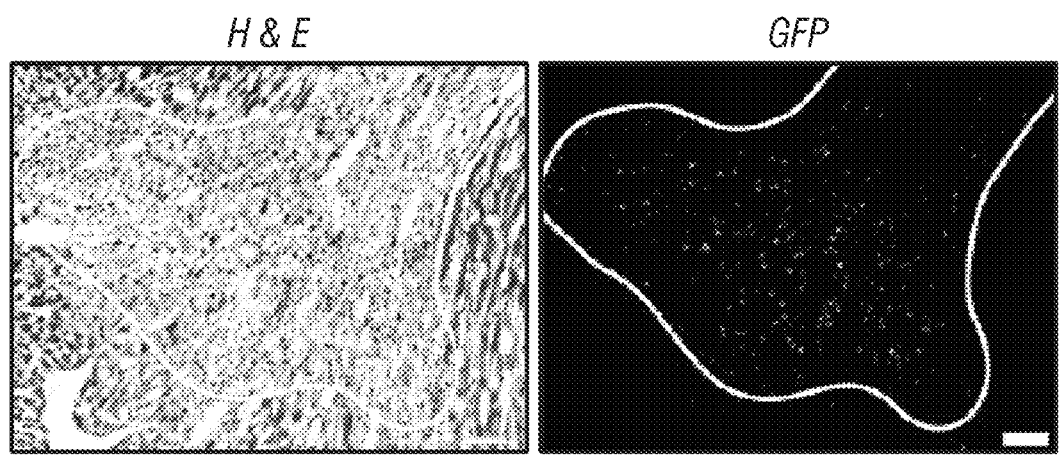

Following MI or other forms of cardiac injury, cardiomyocytes are lost and CFs are activated to produce collagen and other extracellular matrix components, causing fibrosis and impaired cardiac function (Porter and Turner, 2009). To determine whether reprogramming CFs to a cardiomyocyte fate might blunt the decline in cardiac function post-MI, the inventors expressed the transcription factors in CFs and other dividing cells in vivo using a retrovirus expression system, which directs expression only in replicating cells (Miller et al., 1990) (FIG. 19A). Adult mammalian cardiomyocytes do not divide and are therefore resistant to retroviral expression. The inventors confirmed the specificity of retroviral infection for replicating non-cardiomyocytes by injecting concentrated GFP retroviruses into injured hearts after ligation of the left anterior descending coronary artery (LAD), which induces MI. GFP expression was clearly detected in the ischemic area (FIG. 19B).

Figure 19C:
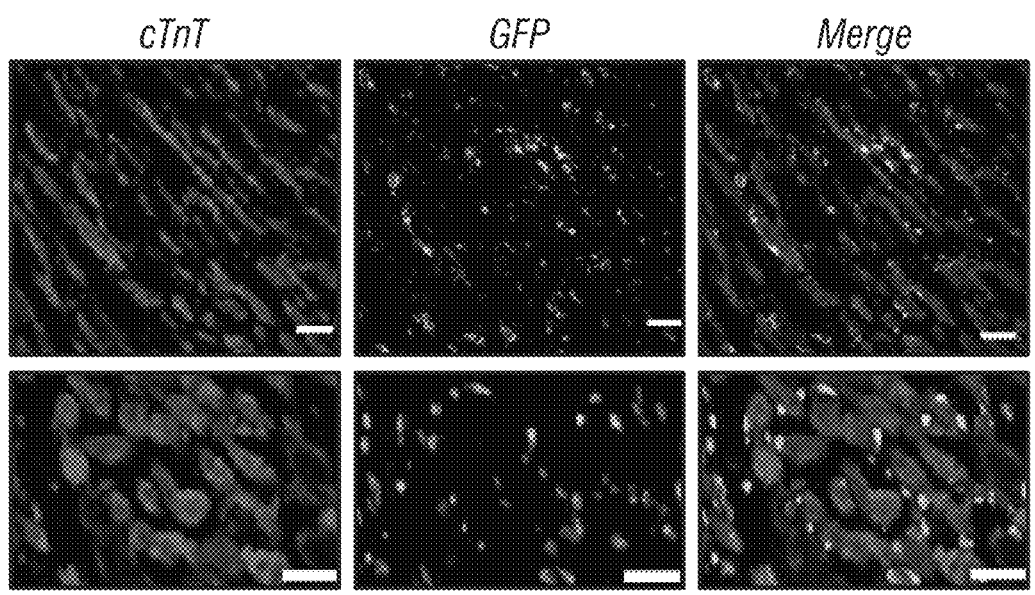

However, none of the GFP+ cells expressed the cardiac marker, cTnT, consistent with the specificity of retroviral infection for proliferating non-cardiomyocytes (FIG. 19C).

Figure 19D:
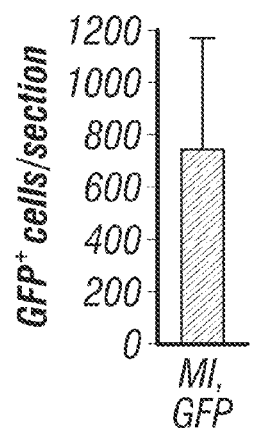

745.6±430.7 GFP+ non-cardiomyocytes were detected per heart sections (FIG. 19D). Co-injection of GHMT viruses with a Tomato virus marker, followed by isolation of cardiomyocytes from hearts 30 days later, showed that Tomato was expressed in bona fide cardiomyocytes (FIG. 2A), indicative of newly formed cardiomyocytes induced by GHMT.

Figures 2A, 2B:
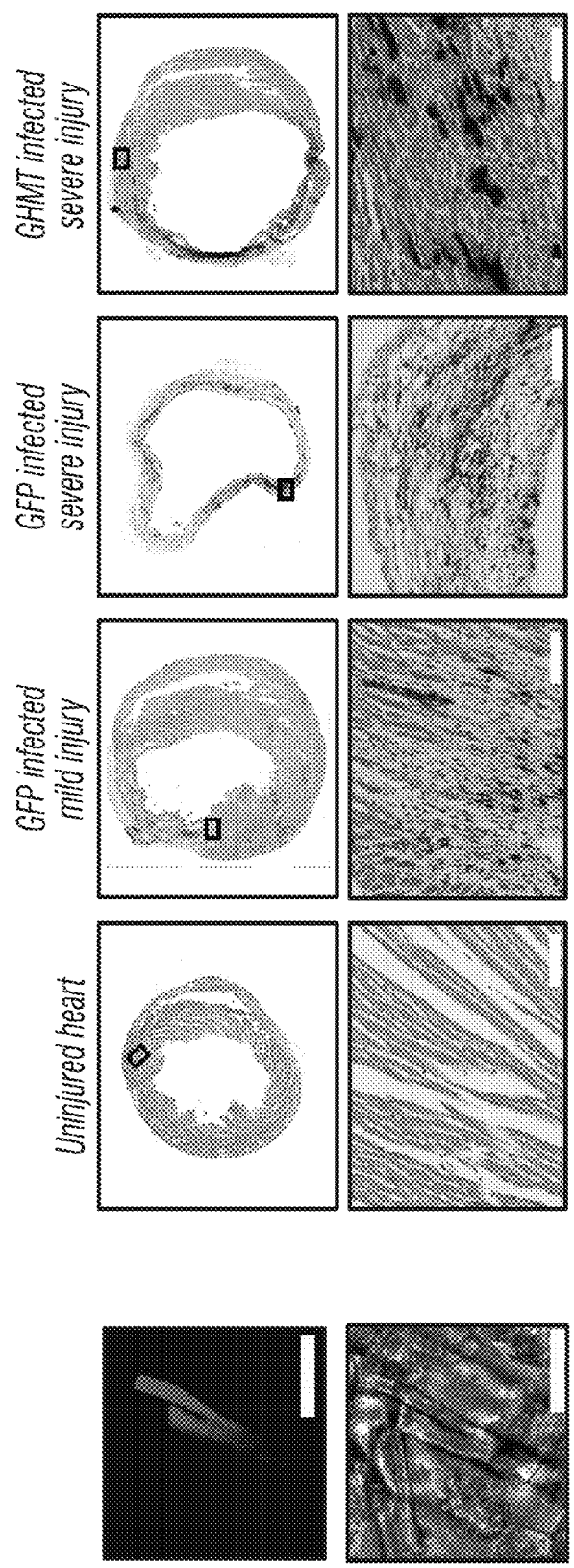
FIGS. 2A-I. Reprogramming CFs toward a cardiac fate in vivo by GHMT.
Figure 2C:
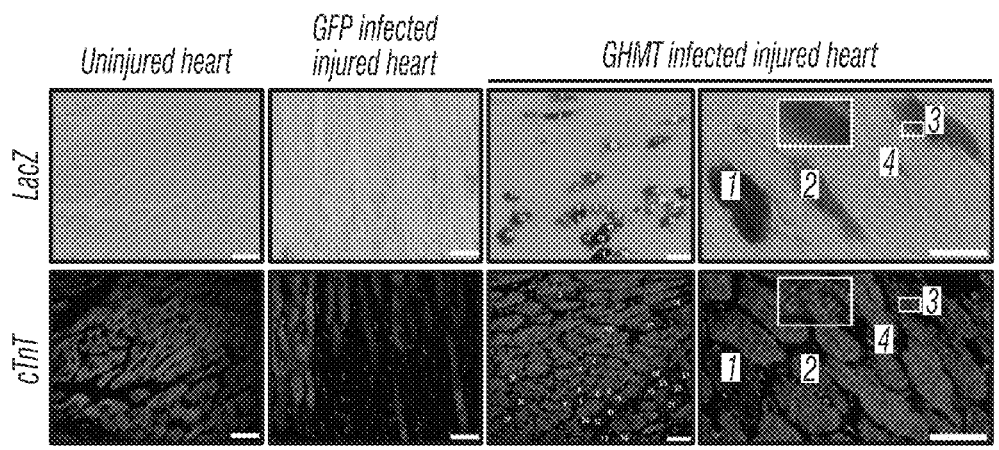
Figure 2D:
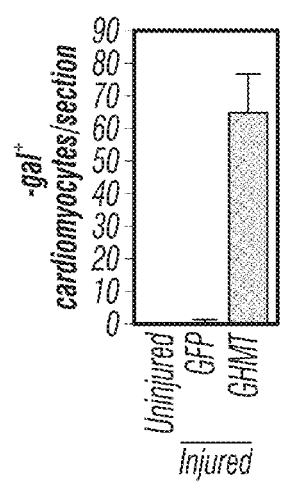

FSP1 is expressed in non-cardiomyocytes such as fibroblasts and transitioning epithelia (Bhowmick et al., 2004; Zeisberg et al., 2007; Schneider et al., 2007). In mouse and human hearts, expression of FSP1 primarily colocalizes with markers of CFs and increases following MI (Schneider et al., 2007). Non-cardiomyocytes in mice carrying alleles of FSP1-Cre and Rosa26-LacZ are specifically labeled with β-galactosidase (β-gal), providing a reliable marker for fibroblast lineage tracing (Bhowmick et al., 2004). To trace the fate of cardiac fibroblasts expressing cardiac transcription factors in vivo, the inventors performed LAD ligation on FSP1-Cre/Rosa26-LacZ mice and injected concentrated retroviruses encoding GHMT or GFP into the border zone immediately following LAD ligation. The inventors analyzed β-galactosidase activity in histological sections of hearts. In uninjured hearts, less than one β-gal+cardiomyocyte per section was observed. After injury, β-gal expression was readily detected in CFs throughout the infarct zone (FIGS. 2B-C).

Figure 20A:
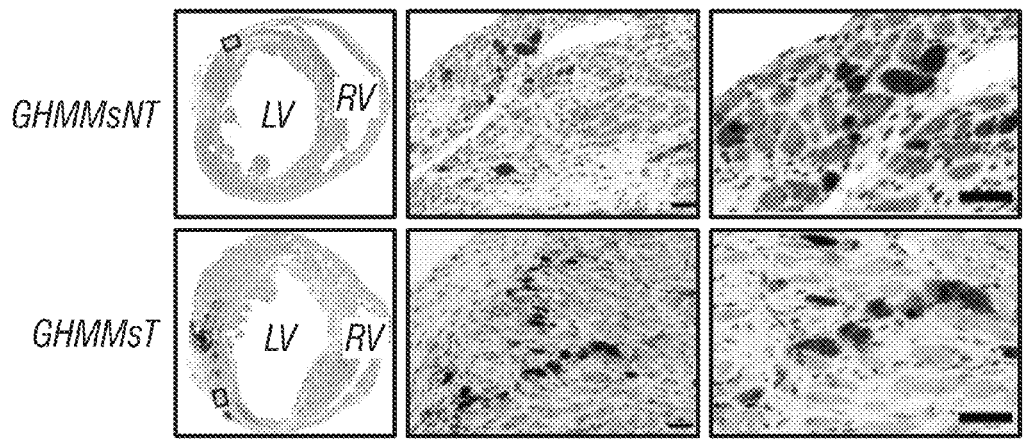
FIGS. 20A-B. Reprogramming CFs to cardiomyocytes in vivo by GHMMsT and GHMMsNT.
Figure 20B:
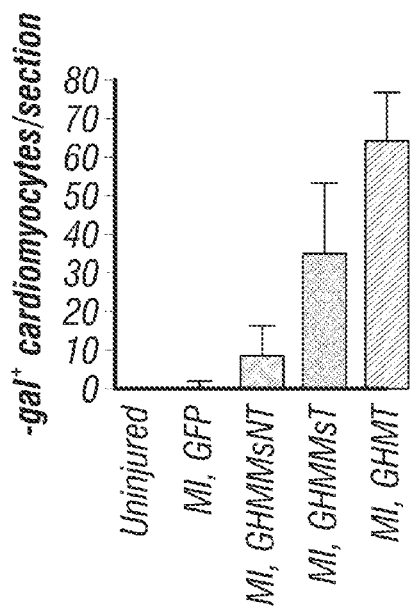

Between 0 and 5 sparsely distributed β-gal+ cardiomyocytes in myocardium of left ventricle (LV) per section were observed in injured hearts infected with GFP viruses (0.4±1.2 β-gal+ cardiomyocytes/section), which may be due to low level ectopic activation. In contrast, abundant clusters of intensely stained β-gal+ cardiomyocytes were observed throughout the infarct and border zone of injured hearts infected with the GHMT retrovirus cocktail (64.8±12.1 β-gal+ cardiomyocytes/section) (FIGS. 2B-C) As mentioned before, retrovirus infected ~745 non-cardiomyocytes per section (Supplementary FIG. 15d), suggesting that GHMT reprogrammed ~8.7% of infected cells into β-gal+ cardiomyocytes in vivo. Generally, more β-gal+ cardiomyocytes were observed in the border zone adjacent to the infarct region, which may be due to intact vascular structures or higher viral infection in this region. Similar results were obtained upon injection with GHMMsT, whereas the inclusion of Nkx2-5 (GHMMsNT) diminished the efficacy of the other five factors (FIGS. 20A-B), as seen in vitro. β-gal+ cardiomyocytes expressed cTnT and showed clear striations (FIG. 2C).

Figure 21C:
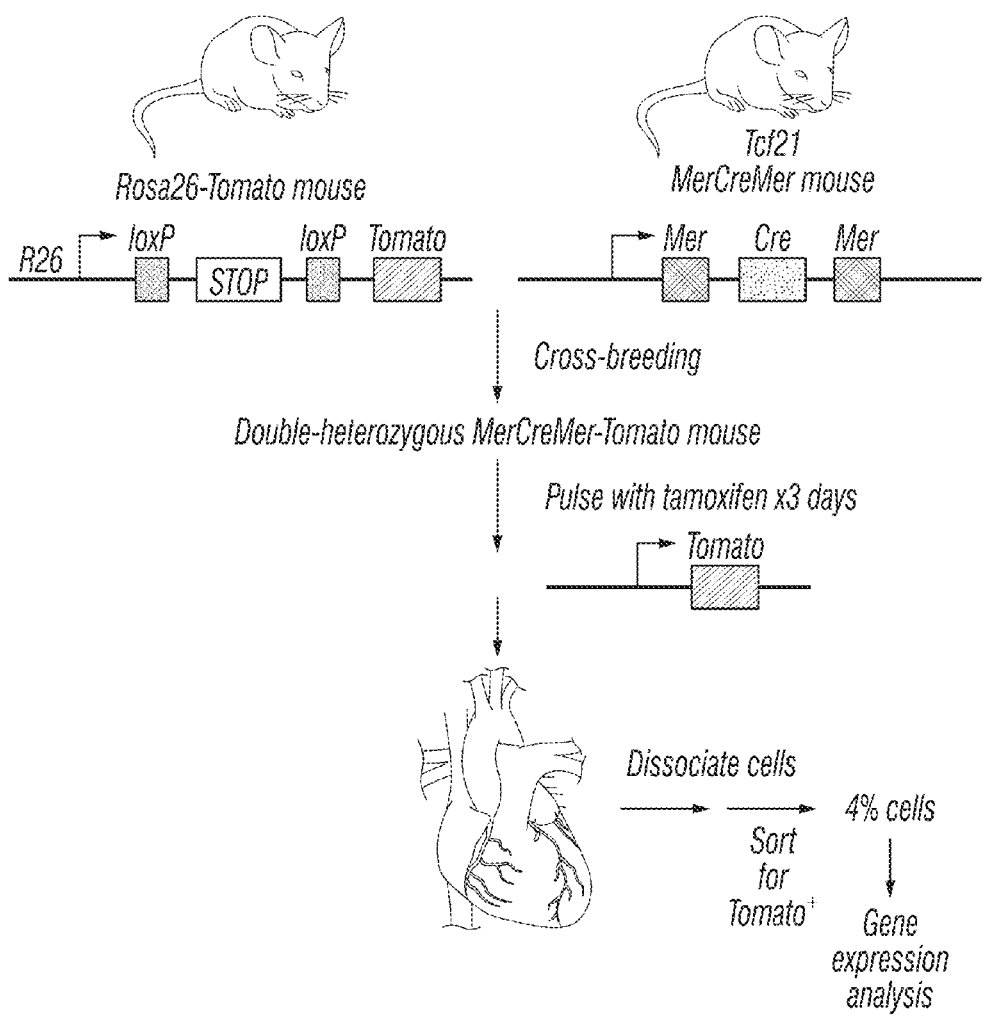
Figure 21D:
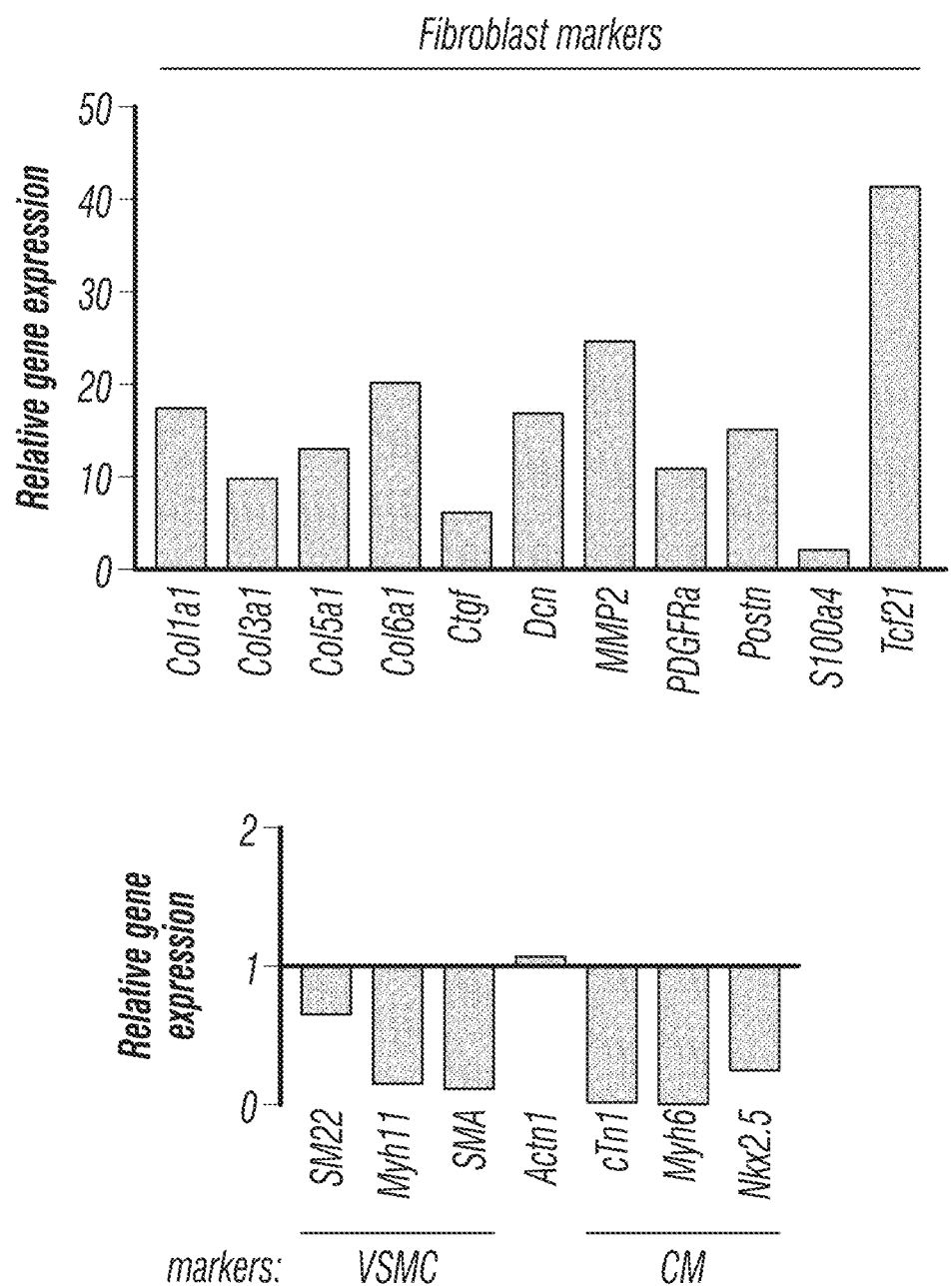
Figure 21E:
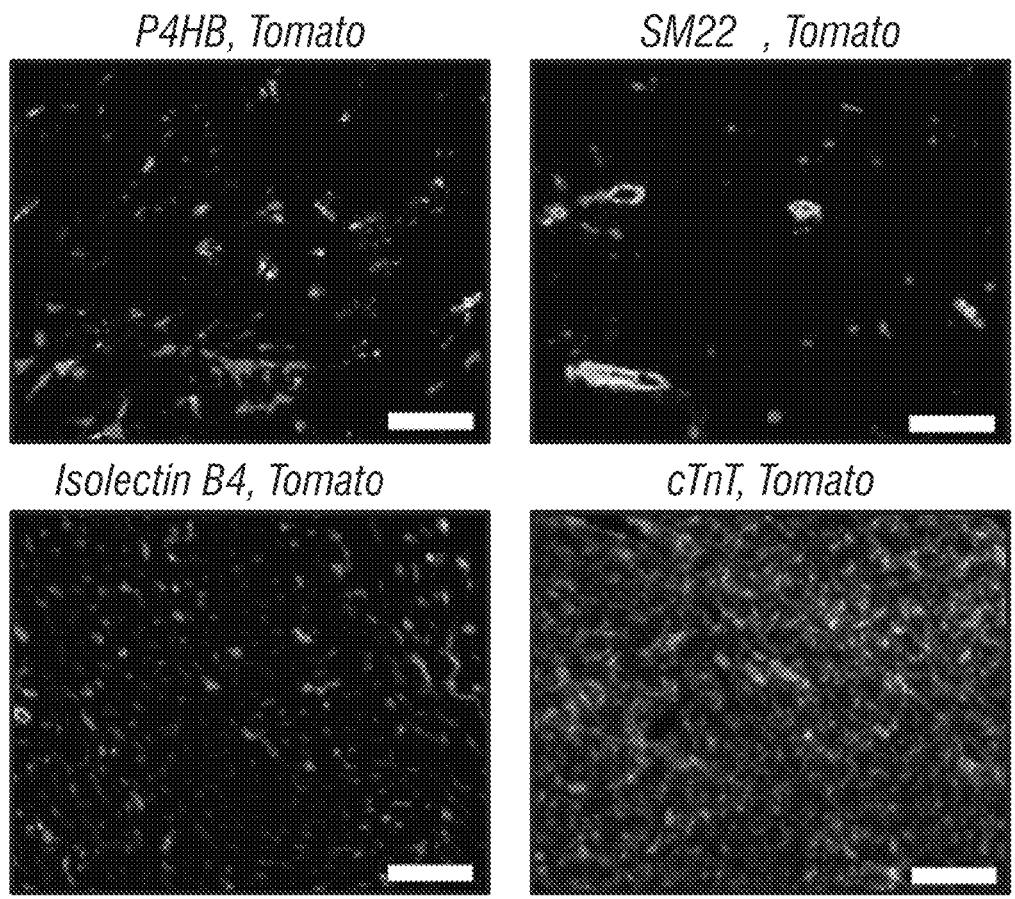
Figure 22:
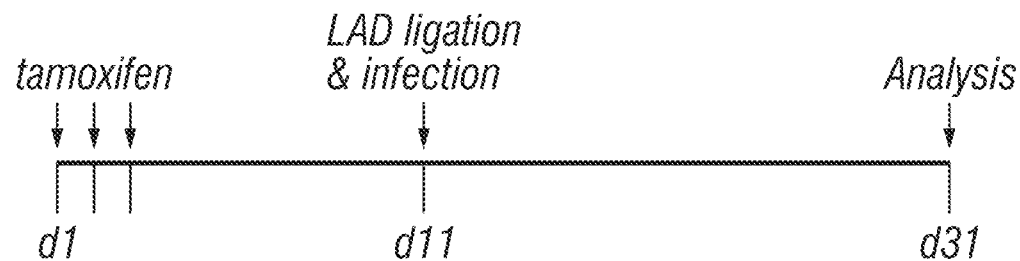
FIG. 22. Experimental design for inducible labeling of CFs in vivo. Mice harboring a Tcf21iCre/+: R26RtdT were treated with tamoxifen for three consecutive days to label CFs. Eight days after tamoxifen treatment (on day 11), LAD ligation was performed and hearts were injected with retrovirus encoding GFP or GHMT. Hearts were analyzed on day 31.

As an independent marker of cardiac fibroblasts, the inventors generated a strain of mice harboring an inducible MerCreMer expression cassette inserted by homologous recombination into the Tcf21 (capsulin/epicardin) locus (Tcf21iCre) (FIGS. 21A-B). Intercrossing of these mice with mice bearing R26RtdTomato showed specific expression of Tomato fluorescence predominantly in cardiac fibroblasts (FIGS. 21C-E), but the inventors rarely observed Tomato expression in cardiomyocytes of normal hearts (0.4±0.8 Tomato+ cardiomyocytes per section, FIG. 2F). Tcf21iCre is a valuable genetic tool for spatiotemporal lineage tracing cardiac fibroblasts (Acharya et al., 2011). Tcf21iCre; R26RtdT mice were treated with tamoxifen for three days to mark Tcf21-expressing cells. Eight days after the last tamoxifen treatment, LAD ligation was performed and animals were injected with GFP or GHMT viruses and analyzed 20 days later (FIG. 22).

Figure 2E:
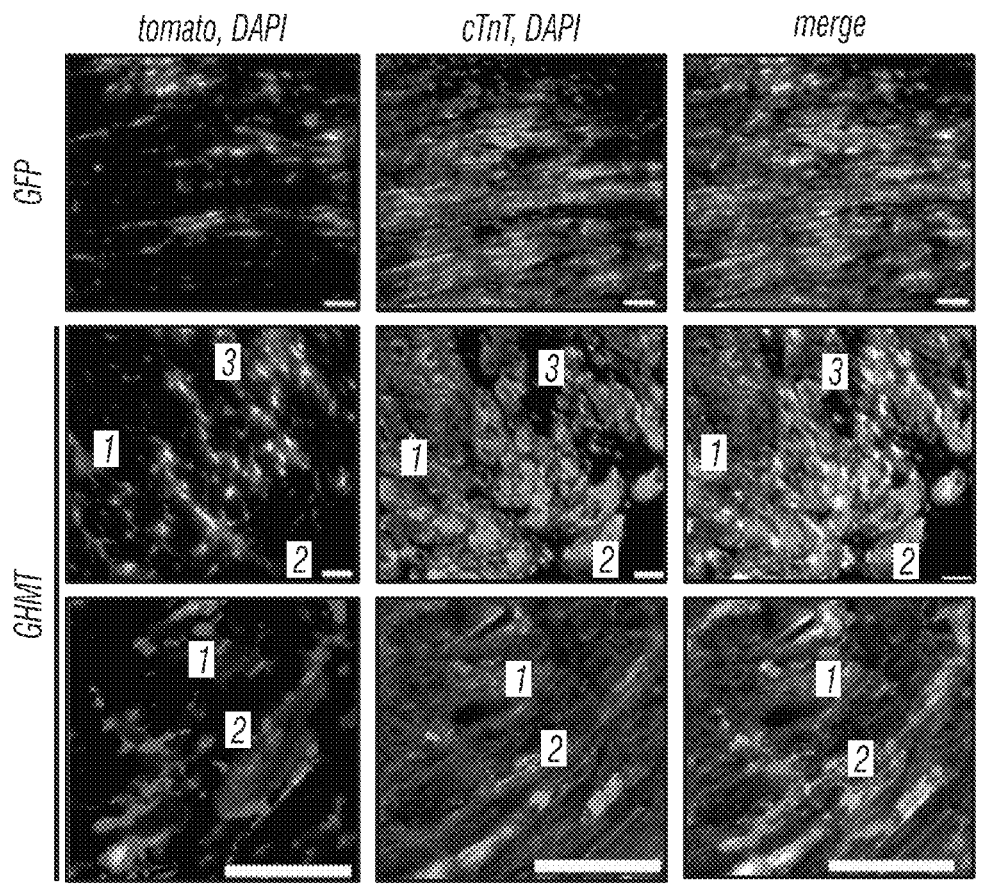
Figure 2F:
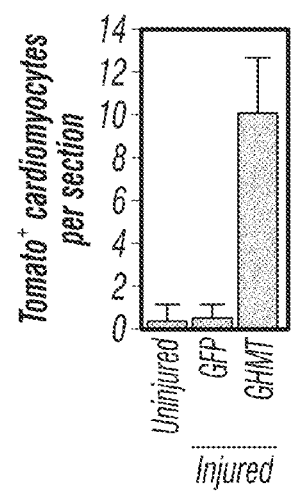
Figure 2G:
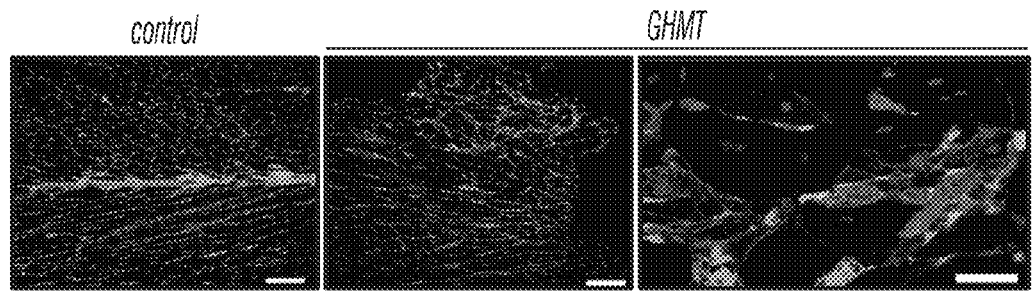
Figure 2H:
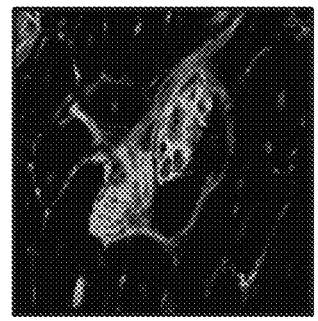
Figure 2H:
Figure 2H:
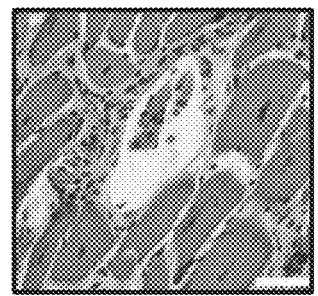
Figure 2H:
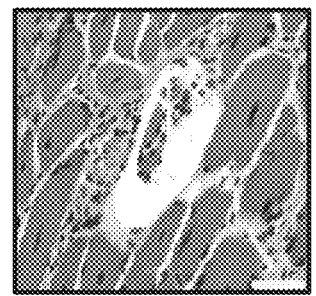
Figure 2I:
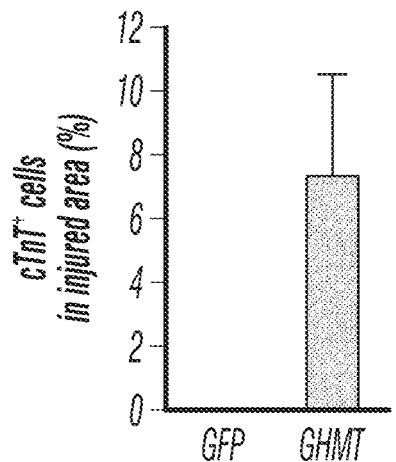
Figure 23A:
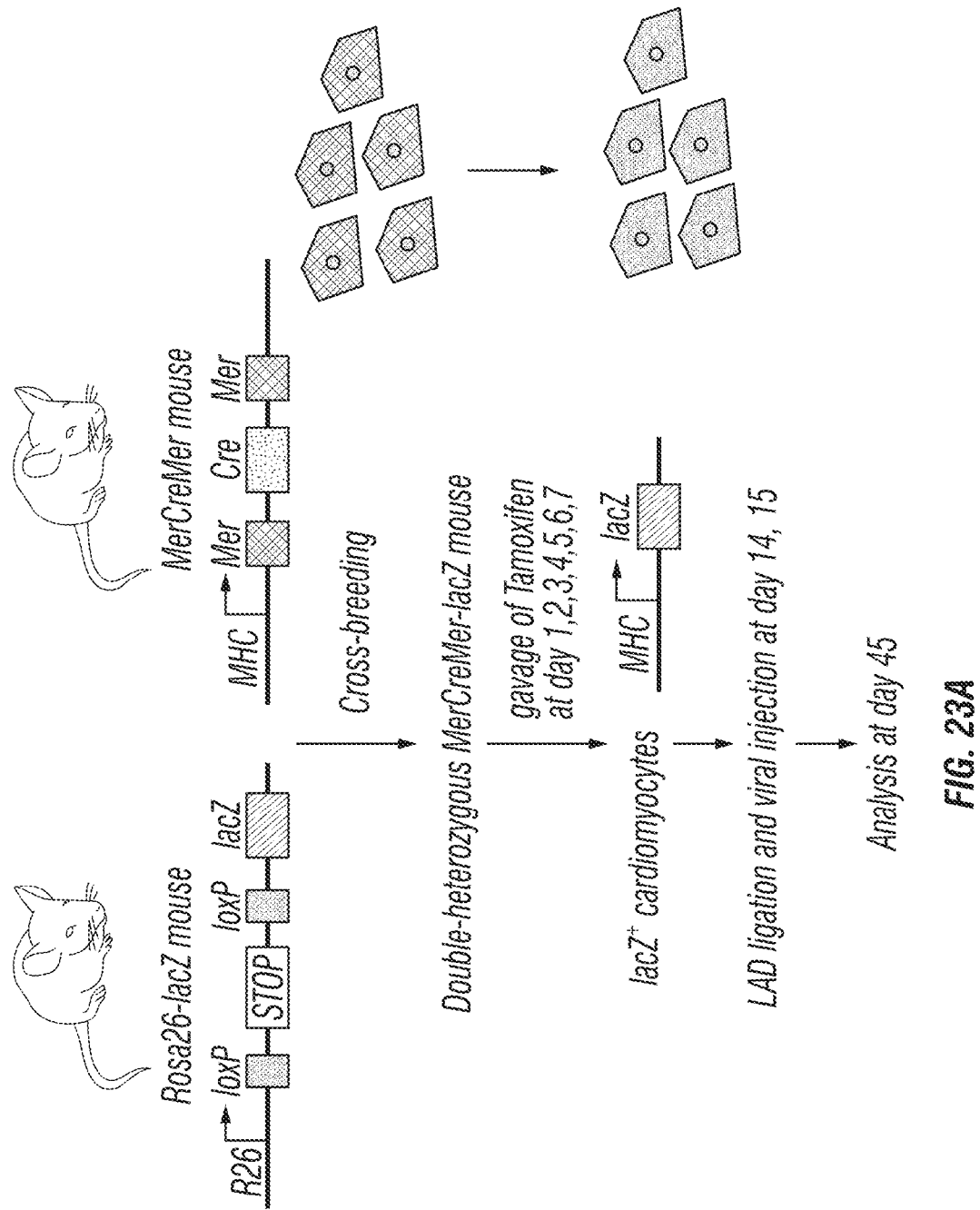
FIGS. 23A-C. Using the inducible αMHC-MerCreMer, Rosa26-LacZ mouse line to show that GHMT promotes the formation of new cardiomyocytes following MI.
Figure 23B:
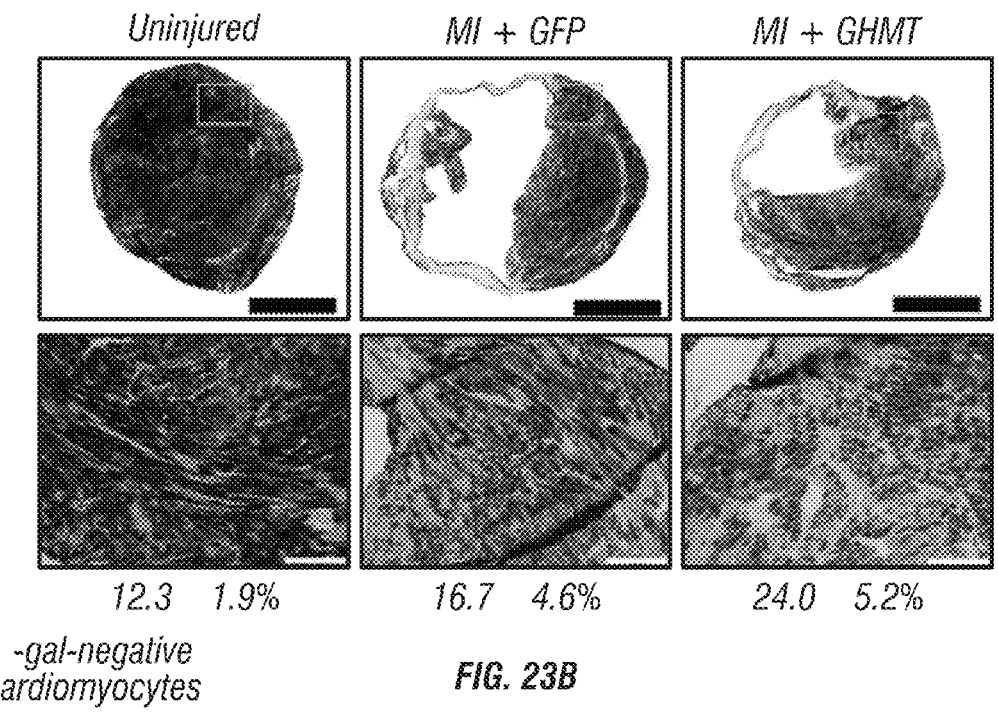
Figure 23C:
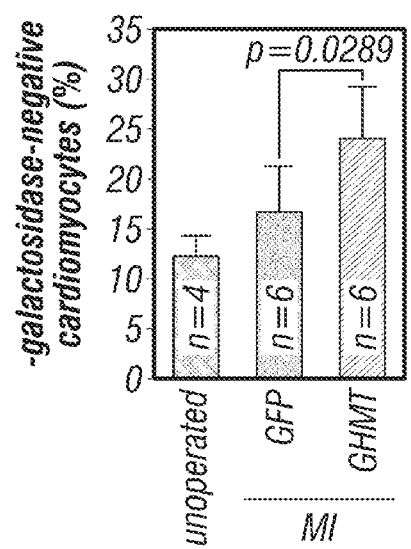
Figure 24:
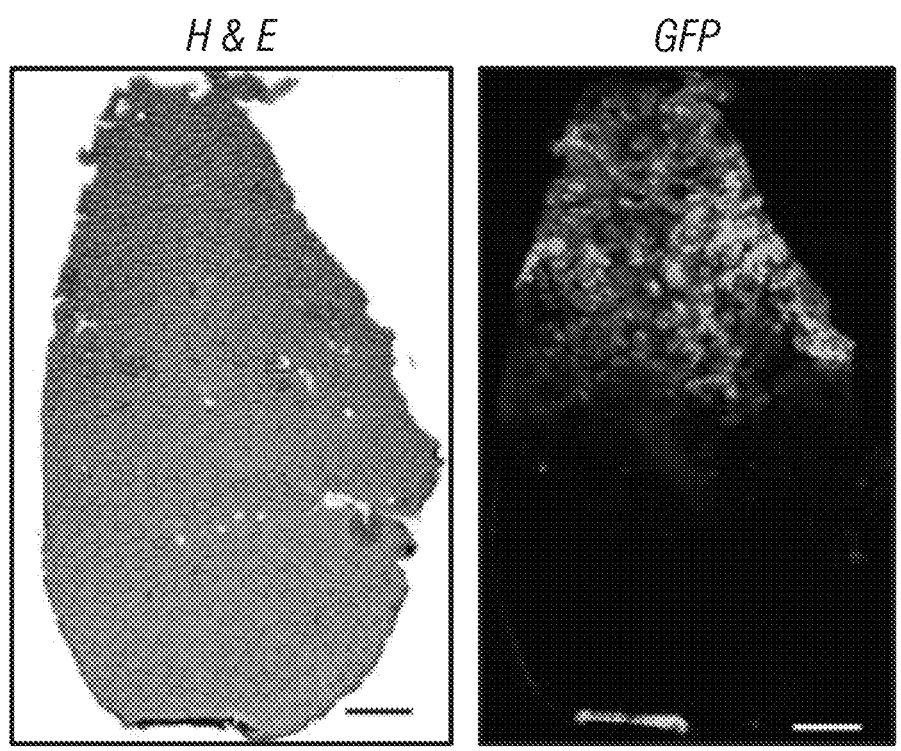
FIG. 24. Retroviral delivery of GFP into mouse hindlimb. Mouse hindlimbs were injected with cardiotoxin (50 μl of 10 μM) to induce myofiber injury. Twenty-four and 48 hours later, hindlimbs were injected with 50 μl of retrovirus encoding GFP or GHMT. Three weeks later, tibialis anterior muscles were dissected, sectioned and stained for H&E (left panel) or visualized for GFP (right panel). Scale bar, 0.1 mm.

Numerous Tomato+ cardiomyocytes were observed in GHMT-injected hearts (10.1±2.5 Tomato+ cardiomyocytes per section) compared to GFP-injected ones (0.5±0.7 Tomato+ cardiomyocytes per section) (FIGS. 2E-F). These findings suggest that forced expression of GHMT in cardiac fibroblasts of the heart is sufficient to induce the expression of cardiac markers. To further test whether GHMT indeed promoted the formation of new cardiomyocytes following MI, the inventors utilized mice with an inducible αMHC-MerCreMer transgene and floxed Rosa26-LacZ reporter. Gavage of these mice with tamoxifen for seven consecutive days resulted in labeling of 87.7±1.9% of cardiomyocytes in LV myocardium. Following LAD ligation and injection of GFP retroviruses, the inventors observed a reduction in β-gal-labeled cardiomyocytes (83.2±4.6%) in the border zone adjacent to the infarct, suggesting replenishment of cardiomyocytes following injury, as described previously (Hsieh et al., 2007; Loffredo et al., 2011). Injection of GHMT retroviruses further reduced the percentage of β-gal-positive cardiomyocytes in the border zone (76.0±5.2%) (FIG. 23).

These findings suggest that GHMT promotes the formation of new cardiomyocytes from a non-αMHC lineage in vivo following injury. These findings also argue against cell fusion as a possible artifact in interpreting the reprogramming results. The inventors also tested whether other non-myocyte populations were susceptible to reprogramming by GHMT in vivo. Injection of cardiotoxin into skeletal muscle results in myofiber degeneration and activation of local fibroblasts, satellite cells and recruitment of inflammatory cells. Injection of GHMT retroviruses into cardiotoxin-injured hindlimb of mice led to efficient formation of iCLMs (FIG. 24 and FIGS. 3G-I).

Figure 3A:
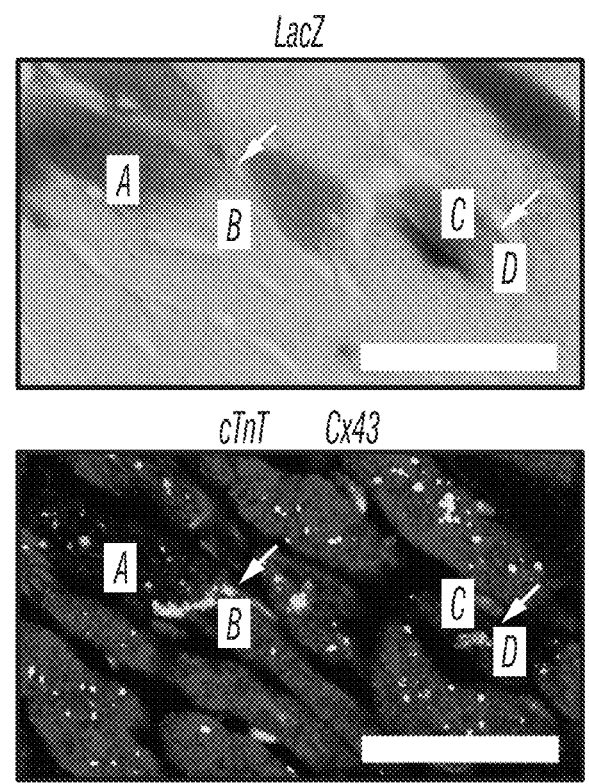
FIGS. 3A-B. Functionality of induced cardiomyocytes in vivo.
Figure 3B:
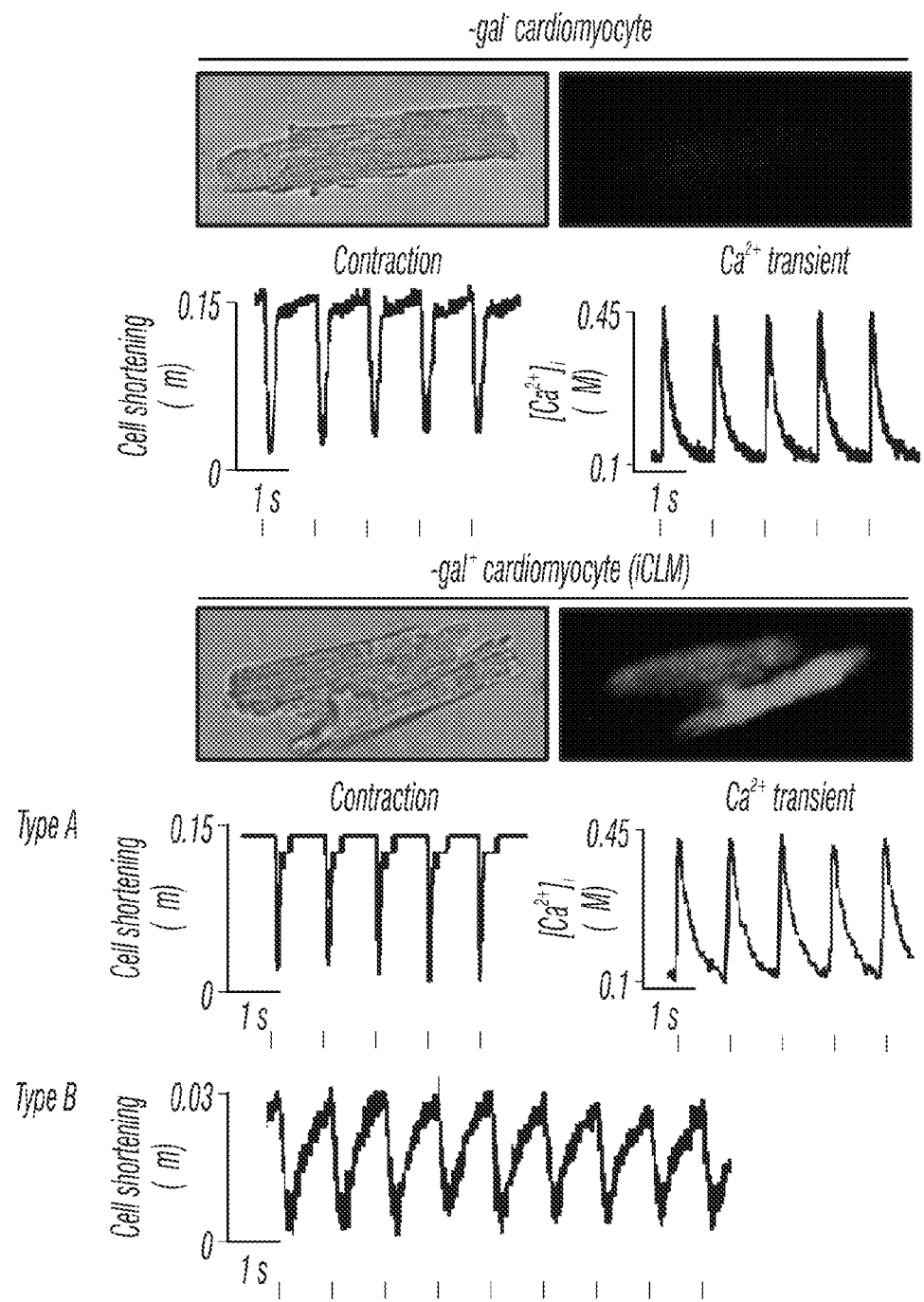

In the heart, gap junctions composed of connexins ensure electrical and metabolic coupling between cardiomyocytes and coordinate their contractility. To determine whether reprogrammed cardiomyocytes could couple with surrounding endogenous myocytes through gap junctions, the inventors performed immunostaining for Connexin 43 (Cx43), the major connexin in functional cardiomyocytes (Saffitz et al., 2000). Gap junctions were observed between β-gal+ and β-gal− cardiomyocytes and between β-gal+ cardiomyocytes (FIG. 3A), indicative of coupling of reprogrammed cardiomyocytes with surrounding myocytes. Reprogrammed β-gal+ cardiomyocytes were isolated from LV myocardium and identified by labeling with a fluorogenic, lipophilic β-gal substrate (C12FDG). These cells displayed a rod-like appearance characteristic of mature cardiomyocytes and 71.4% of reprogrammed β-gal+ cardiomyocytes (type A iCLMs) displayed a pattern of contractility and calcium transients similar to normal ventricular cardiomyocytes in response to electrical pacing at 1 Hz (FIG. 3B), indicating their functionality. However, 28.6% of reprogrammed β-gal+ cardiomyocytes (type B iCLMs) display immature functionality in response to electrical pacing at 1 Hz (FIG. 3B).

Figure 4A:
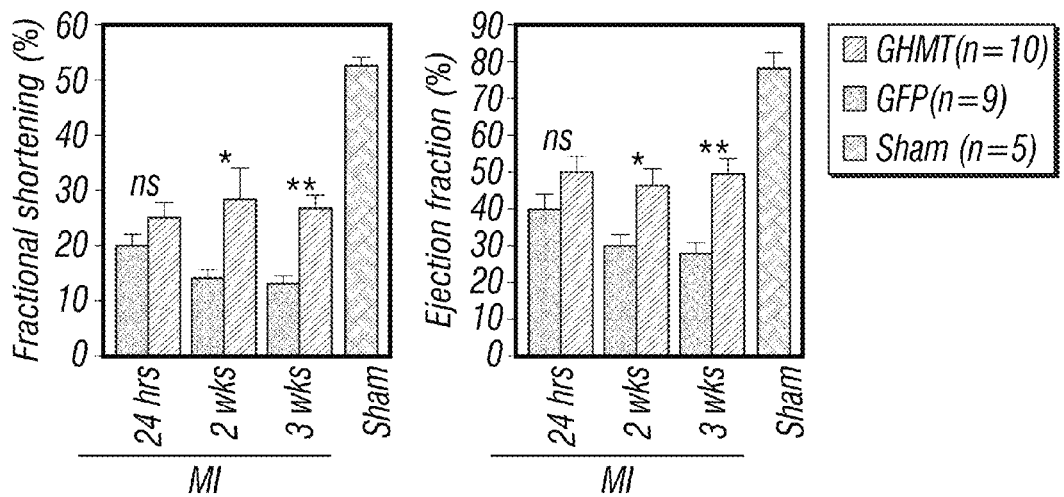
FIGS. 4A-D. Attenuation of cardiac injury by delivery of GHMT into noncardiomyocytes following MI.

In a blinded analysis, the inventors examined whether forced expression of GHMT in noncardiomyocytes could lead to measurable improvement in function of ischemic hearts. Cardiac function following MI was assessed by fractional shortening (FS), ejection fraction (EF), and stroke volume using echocardiography and magnetic resonance imaging (MRI). Twenty-four hours after LAD ligation, FS and EF assessed by echocardiography of all mice decreased by 40-50% relative to sham-operated mice. Thereafter, cardiac function of GFP-injected mice continued to decline, reaching a stable value 2 weeks post-MI; FS~13% and EF~30%. In contrast, infection of injured myocardium with GHMT retroviruses blunted further worsening of cardiac function 3 weeks post-MI; FS~26% and EF~51% (FIG. 4A).

Figure 4B:
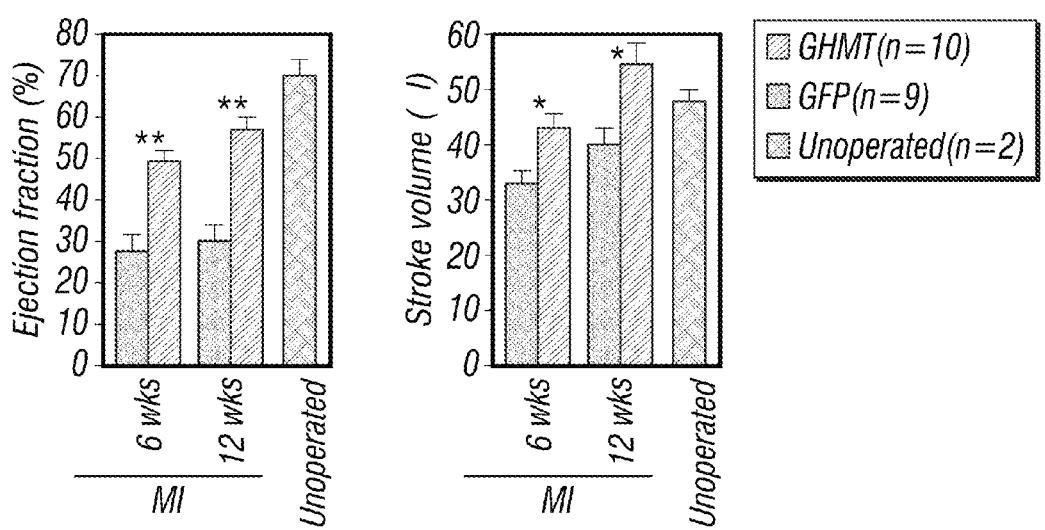
Figure 4C:
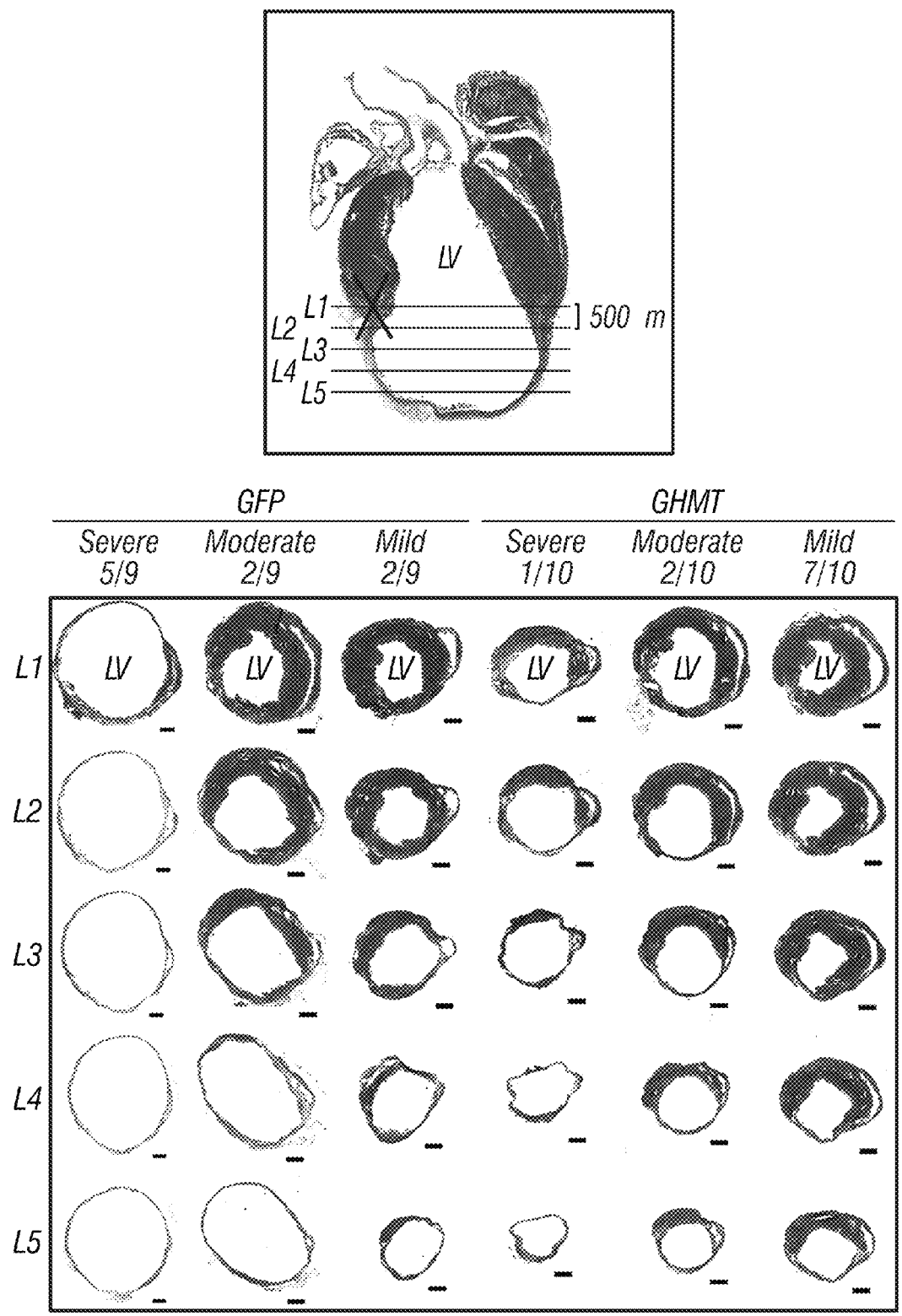
Figure 4D:
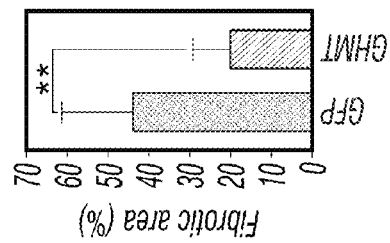
Figure 5A:
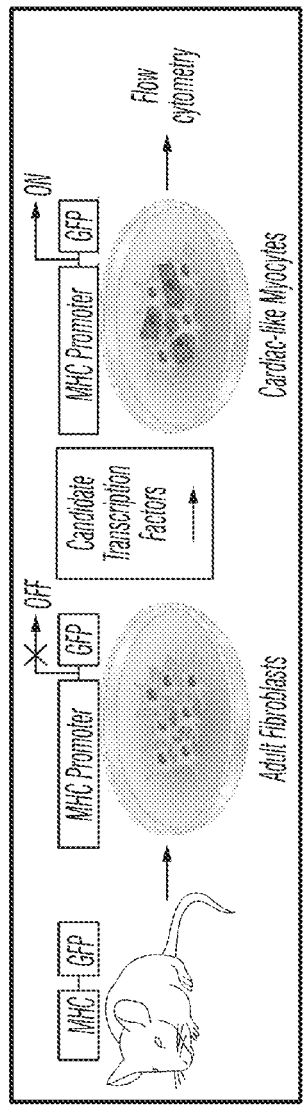
FIGS. 5A-D. Generation of a cardiomyocyte-specific reporter mouse line.
Figure 5B:
Figure 5C:
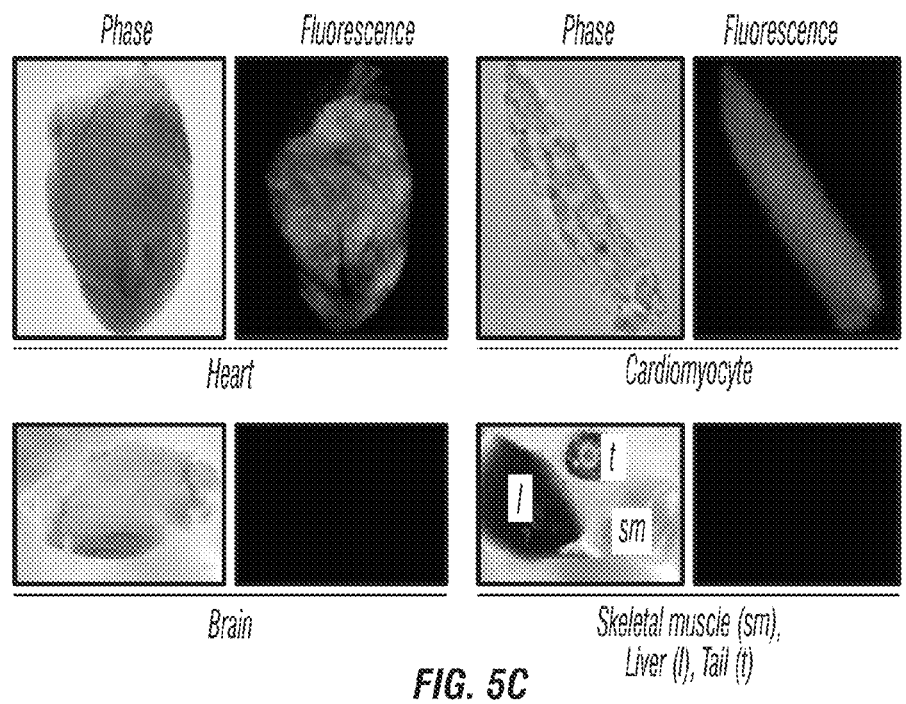
Figure 5D:
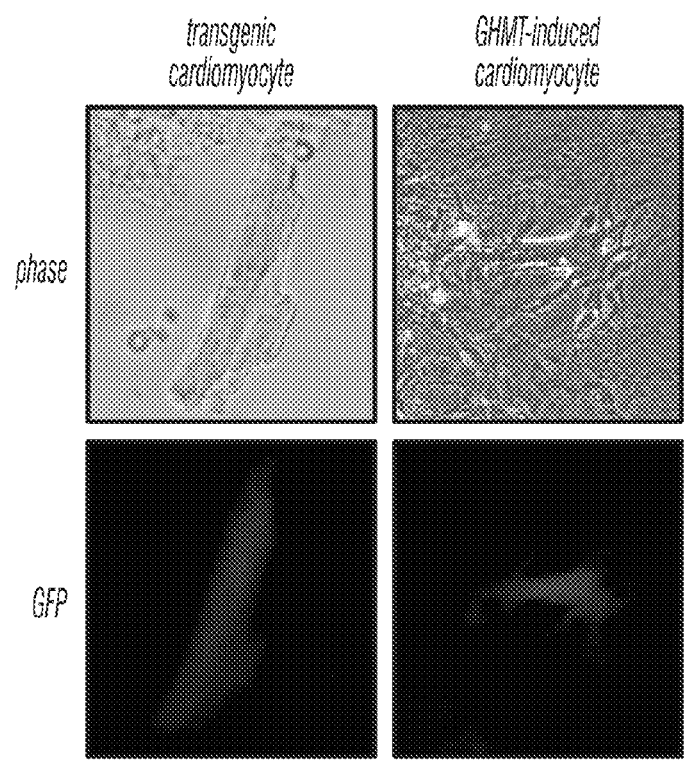
Figure 6:
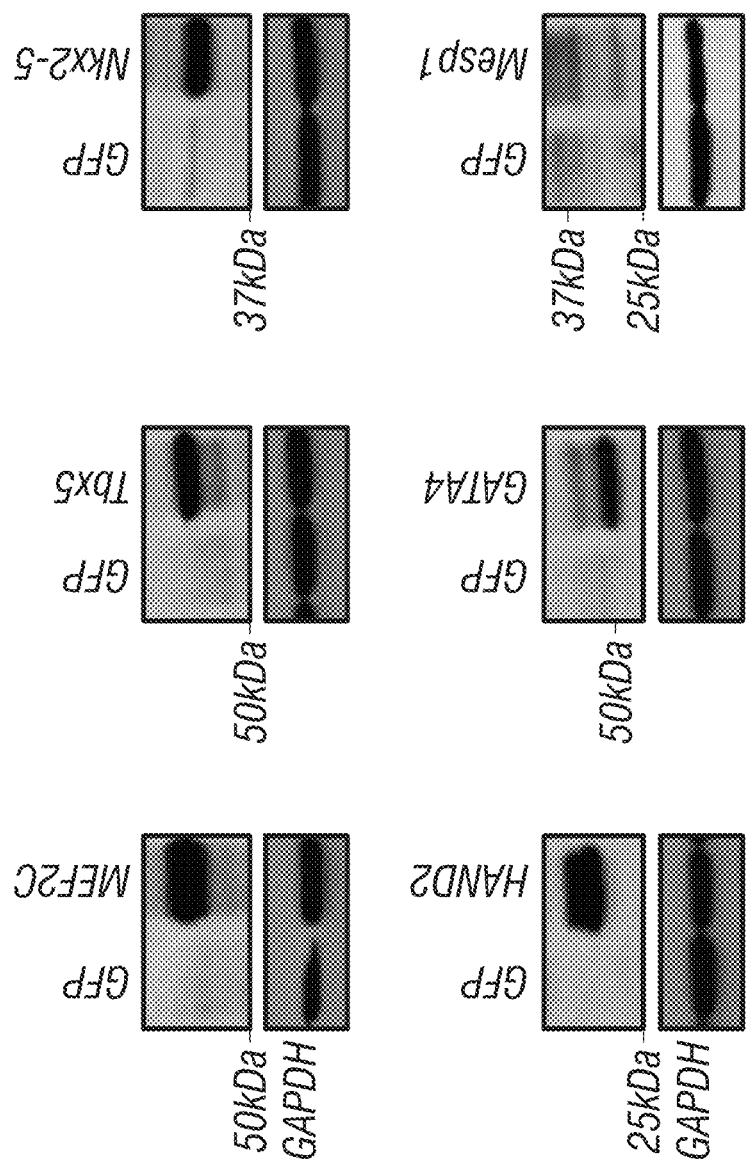
FIG. 6. Generation of retroviruses encoding individual cardiac transcription factors. Mouse 10T1/2 fibroblasts were infected with retroviruses encoding the indicated transcription factors tagged with a Myc-epitope (MEF2C, Tbx5, Nkx2-5, HAND2, and GATA4) or FLAG-epitope (Mesp1) and protein expression was detected by Western blot analysis using anti-Myc or anti-FLAG antibodies with extracts from cells infected with each virus. A GFP-expressing retrovirus was used as a negative control and GAPDH was a loading control.
Figure 25A:
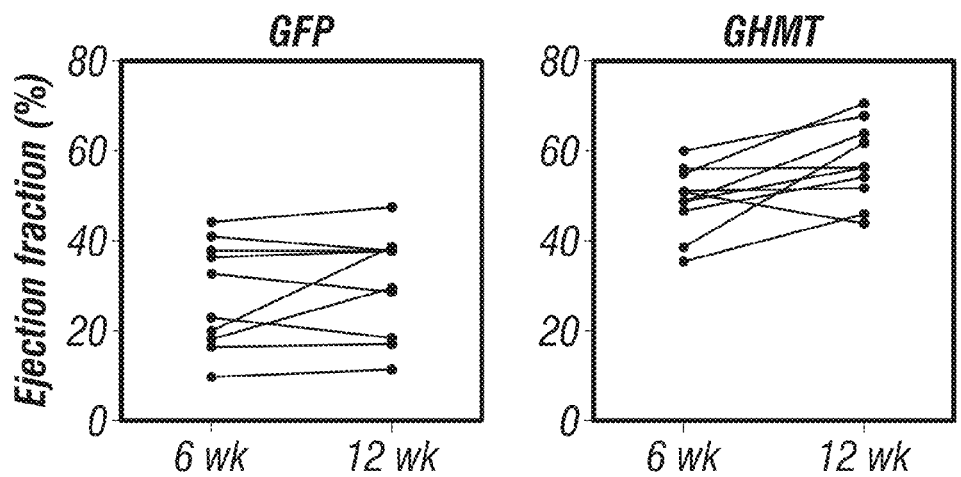
FIGS. 25A-B. Analysis of cardiac function in individual mice. Mice were subjected to LAD ligation followed by intramyocardial injection with retroviruses encoding GFP or GHMT. Cardiac function was evaluated by (FIG. 25A) EF (FIG. 25B) stroke volume using cardiac MRI imaging 6 and 12 weeks later. Each pair of data points, connected by a line, represents data from the same mouse. GHMMsT-infected myocardium following MI. Cardiac fibrosis was evaluated by trichrome staining 4 weeks after MI and GHMMsT retrovirus injection. The severity of cardiac fibrosis was classified as mild, moderate or severe as defined in FIGS. 4A-D. The number indicates the number of hearts showing the indicated severity out of total number of hearts subjected to MI. Five sections from each heart are shown. The ligation site is marked as X. Scale bar, 1 mm.
Figure 25B:
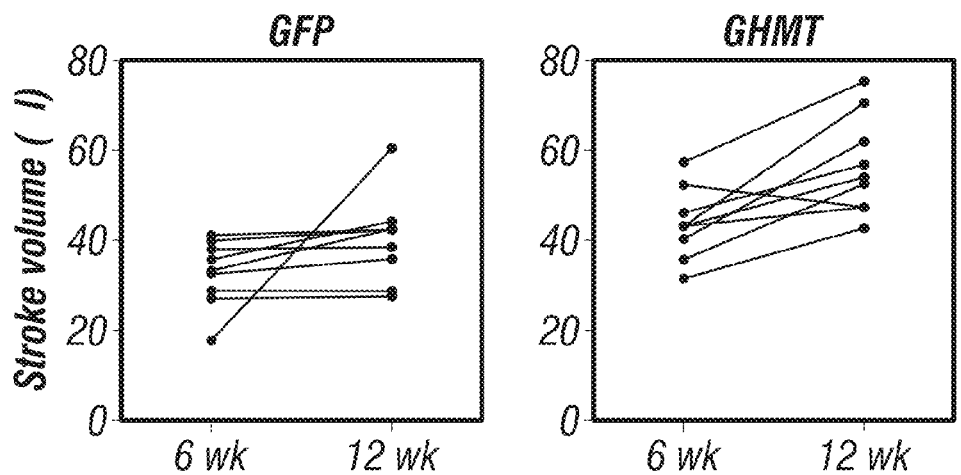
Figure 26:
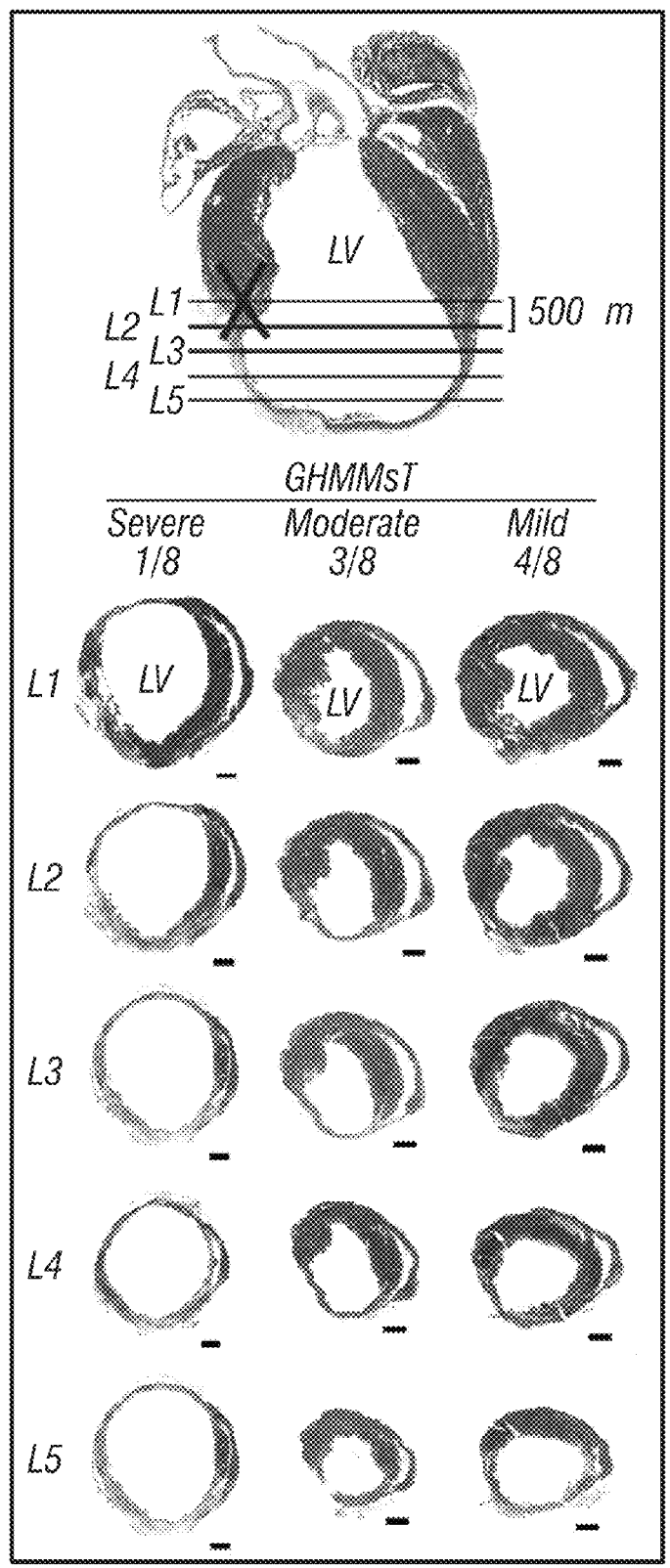
FIG. 26. Evaluation of cardiac fibrosis and scar formation in GHMMsT-infected myocardium following MI. Cardiac fibrosis was evaluated by trichrome staining 4 weeks after MI and GHMMsT retrovirus injection. The severity of cardiac fibrosis was classified as mild, moderate or severe as defined in FIGS. 4A-D. The number indicates the number of hearts showing the indicated severity out of total number of hearts subjected to MI. Five sections from each heart are shown. The ligation site is marked as X. Scale bar, 1 mm.

To determine whether this effect persists long-term, assessed cardiac function at 6 weeks and 12 weeks by EF and stroke volume using cardiac MRI. EF of GFP-injected mice decreased to reach a stable value of ~28% 6 weeks post-MI (FIG. 4B). In contrast, infection of injured myocardium with GHMT blunted worsening of EF 6 weeks post-MI (~49%) with further significant improvement at 12 weeks post-MI (~57%) (FIG. 4B). This long-term effect on EF by GHMT was accompanied by significant increases in stroke volume at 12 weeks compared to those values at 6 weeks (FIG. 4B). Individual mice in each group demonstrated similar functional changes in cardiac parameters, indicating the reliability of cardiac MRI to assess cardiac function (FIGS. 25A-B). These data suggest that expression of GHMT in non-cardiomyocytes in injured hearts can sustain cardiac function. Injection of GHMT into injured hearts continues to improve cardiac function after 6 weeks, which may be due to progressive maturation of iCLMs over time. Moreover, GHMT- and GHMMsT-infected hearts showed a pronounced reduction in fibrosis, compared with GFP-infected hearts after MI (FIGS. 4C-D and 26).

Figure 27:
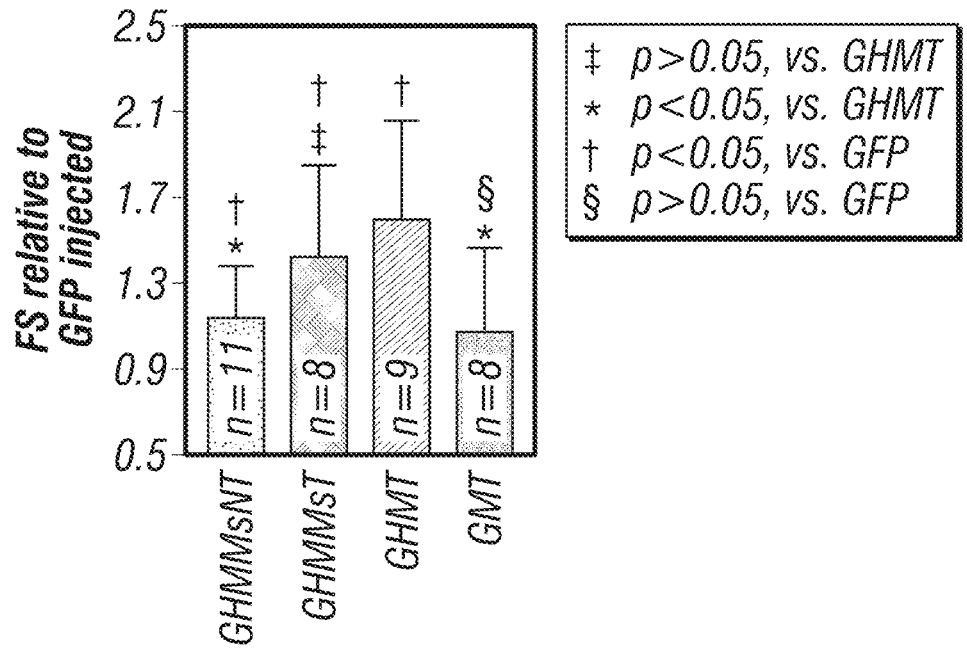
FIG. 27. Comparison of the effects of different combinations of cardiac transcription factors on cardiac function at 3 weeks post-MI. Mice at the age of 8 weeks were subjected to LAD ligation and injection of retroviruses carrying GFP, GHMMsNT, GHMMsT, GHMT or GMT. Cardiac function of each mouse was assessed by FS at 3 weeks post-MI by echocardiography. FS of each mouse injected with a combination of cardiac transcription factors was normalized by average FS of GFP group. Data are presented as mean±std. The p-values are calculated with two-tail t-test.
Figure 28:
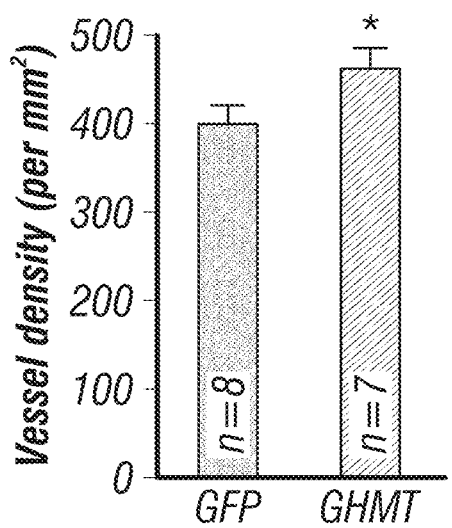
FIG. 28. Analysis of vessel density by isolectin staining. LAD ligation was performed on adult mice followed by injection with GFP or GHMT-expressing retroviruses. Three weeks later, hearts were harvested and sectioned. Vessel density was determined by isolectin staining of the border zone. Values represent the number of isolectin-positive vessel per $mm^2$. Data are presented as mean±std. The p-values are calculated with two-tail t-test. ★: $p<0.05$.
Figure 29:
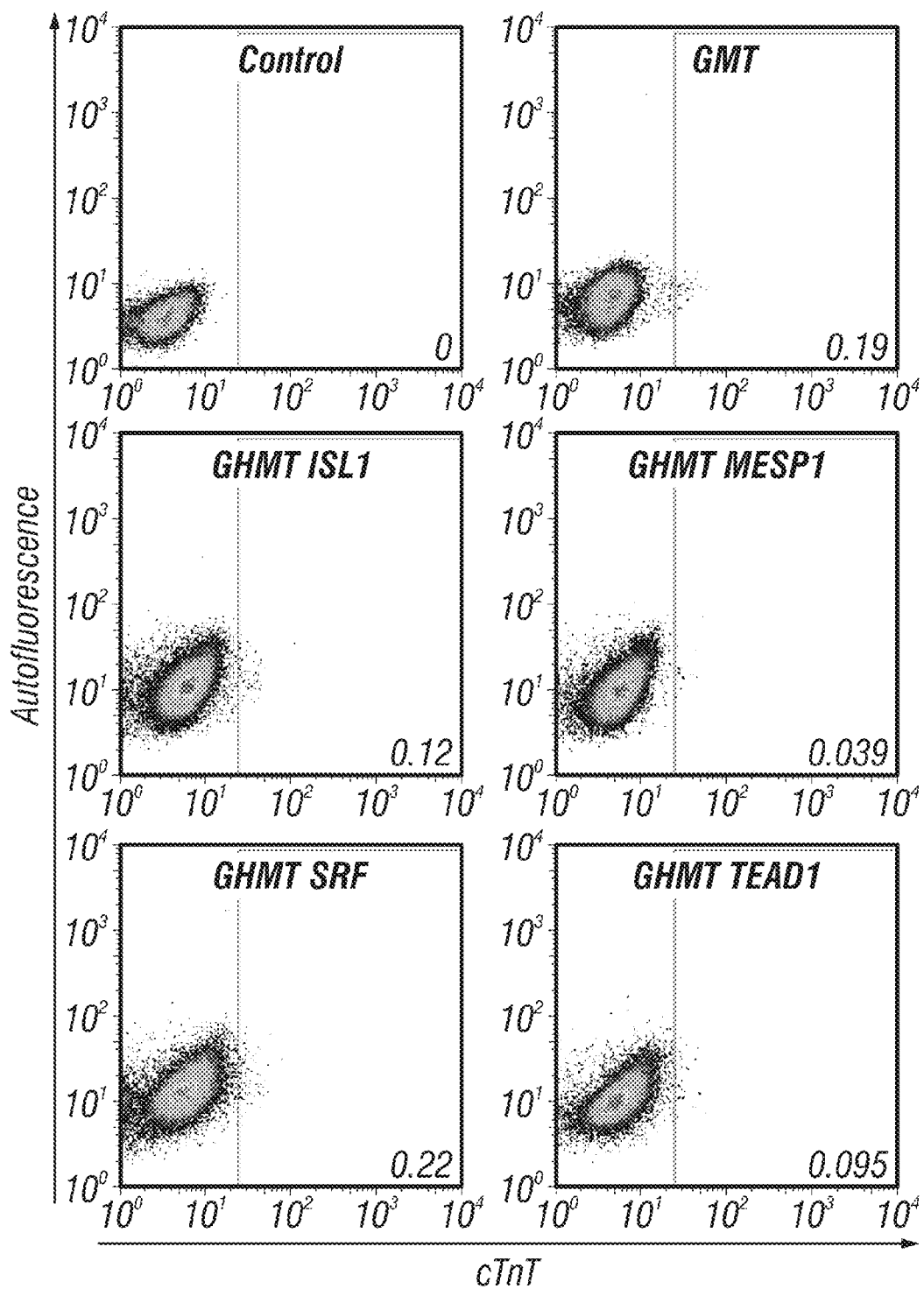
FIG. 29. Flow cytometry analyses to search for additional factors to enhance the expression of cardiac marker, cardiac Troponin T (cTnT) with GHMT in human neonatal foreskin fibroblasts. G: GATA4, H: HAND2, M: MEF2C, T: TBX5 (Top). Summary of flow cytometry analyses (Bottom).
Figure 29:
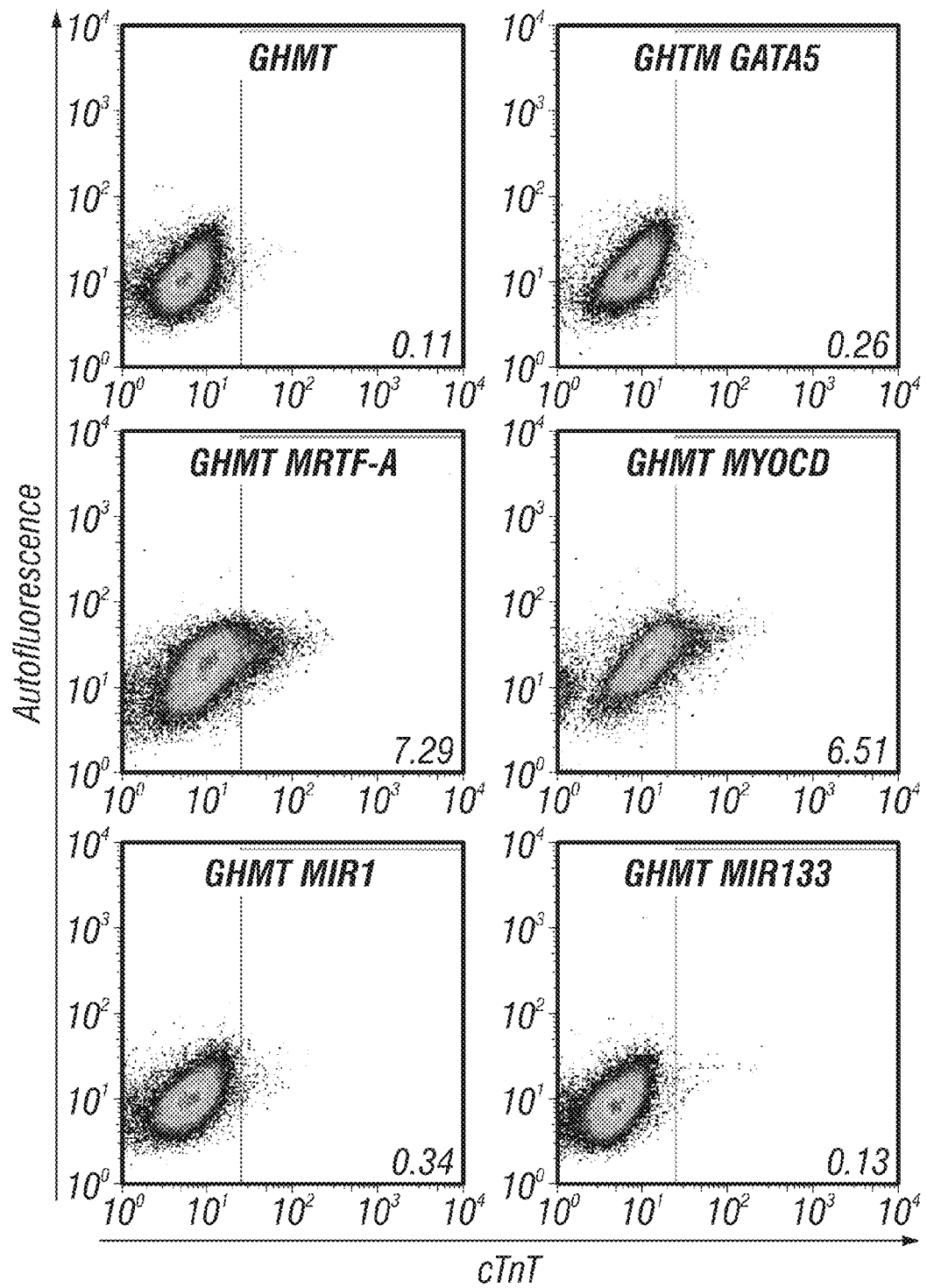
Figure 29:
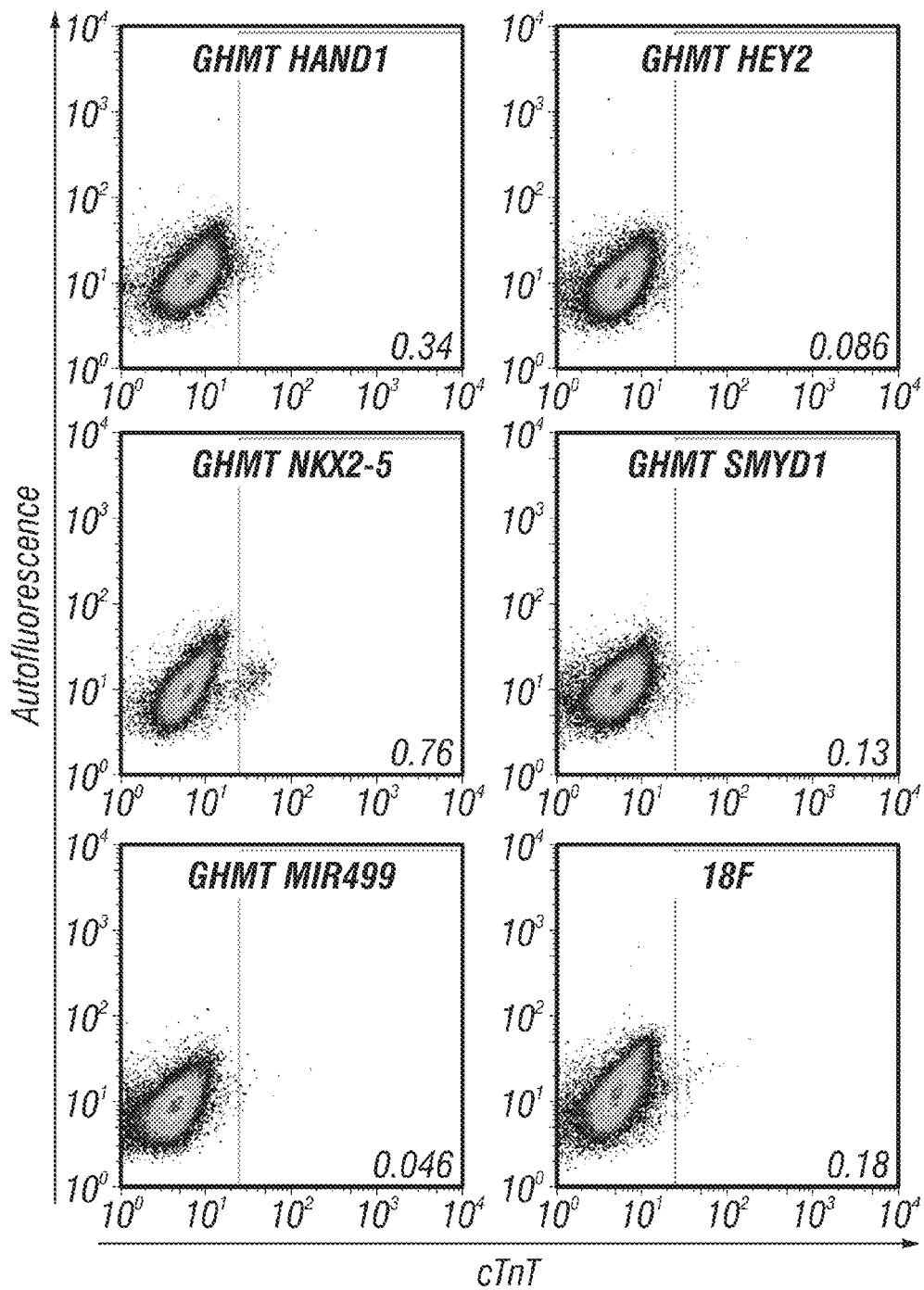
Figure 29:
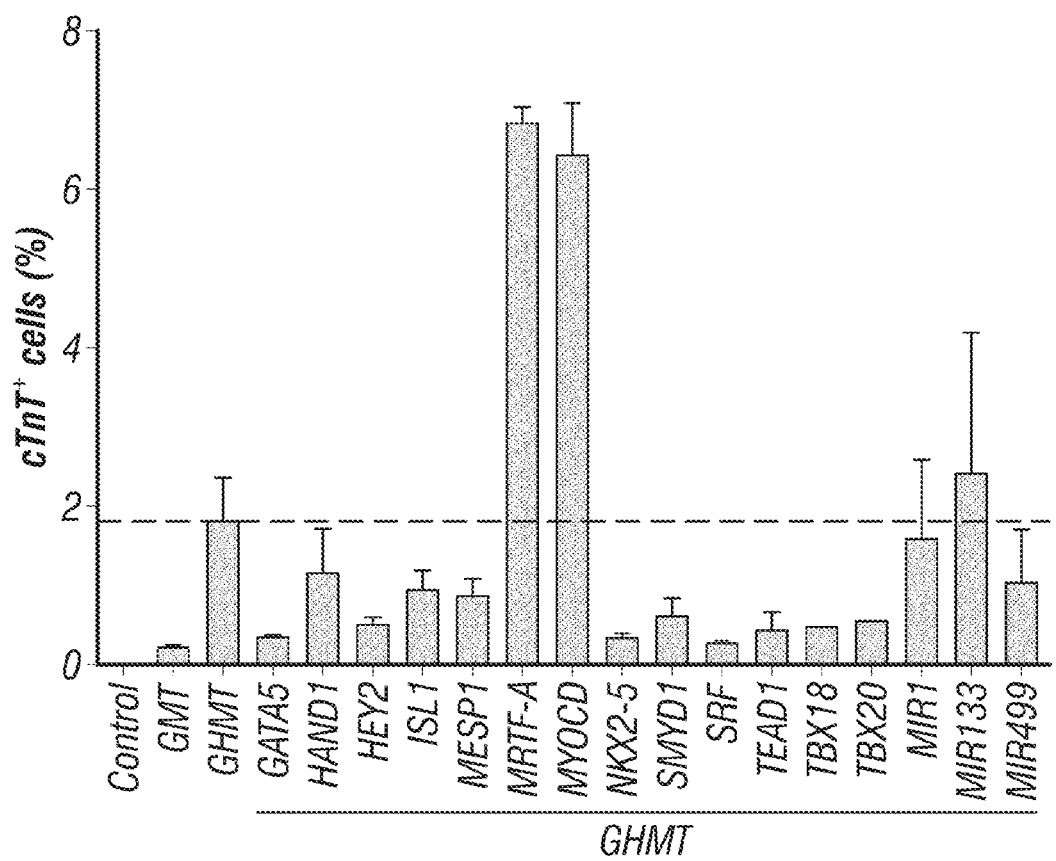
Figure 30:
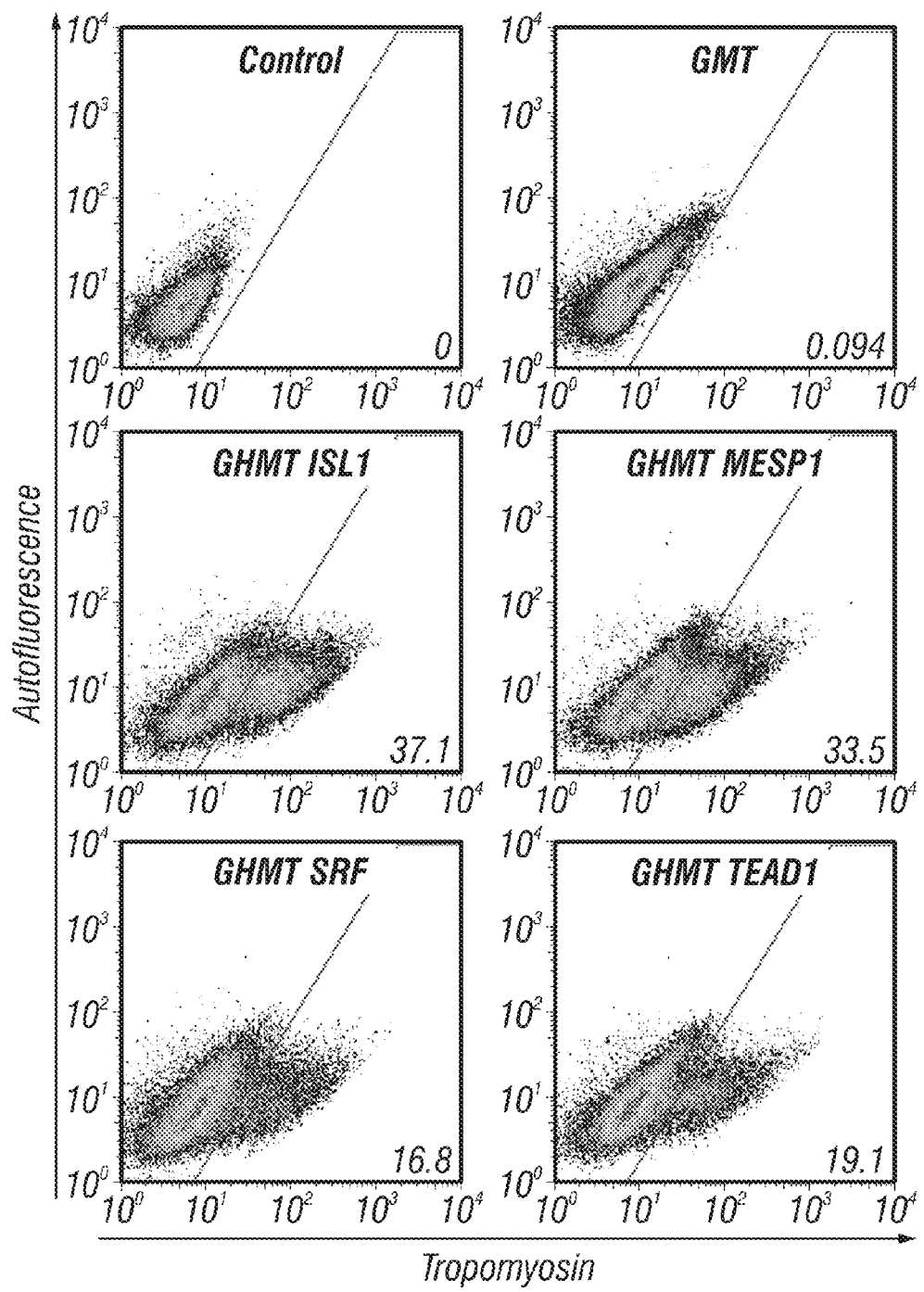
FIG. 30. Flow cytometry analyses to search for additional factors to enhance the expression of cardiac marker, Tropomyosin with GHMT in human neonatal foreskin fibroblasts. G: GATA4, H: HAND2, M: MEF2C, T: TBX5 (Top). Summary of flow cytometry analyses (Bottom).
Figure 30:
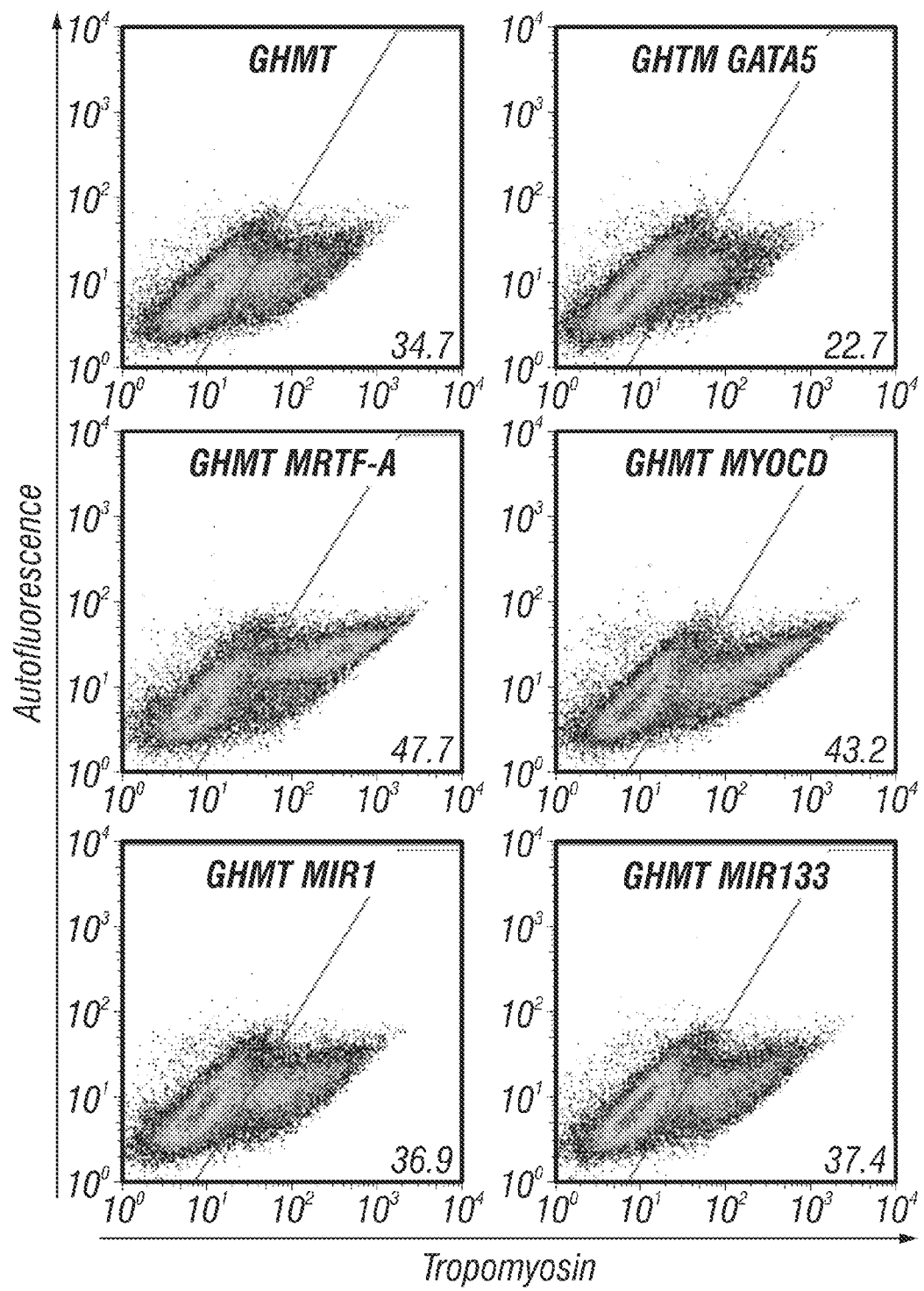
Figure 30:
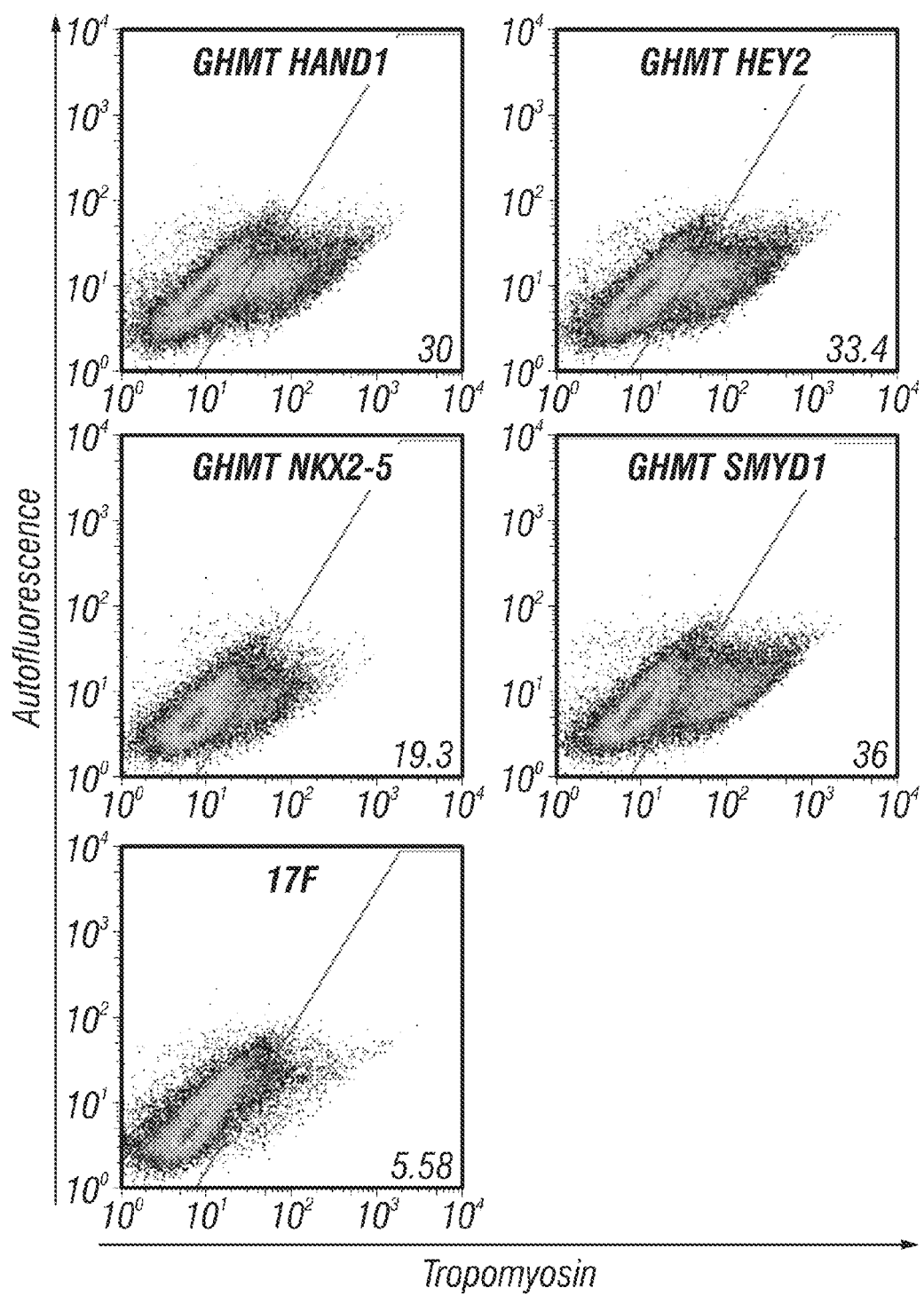
Figure 30:
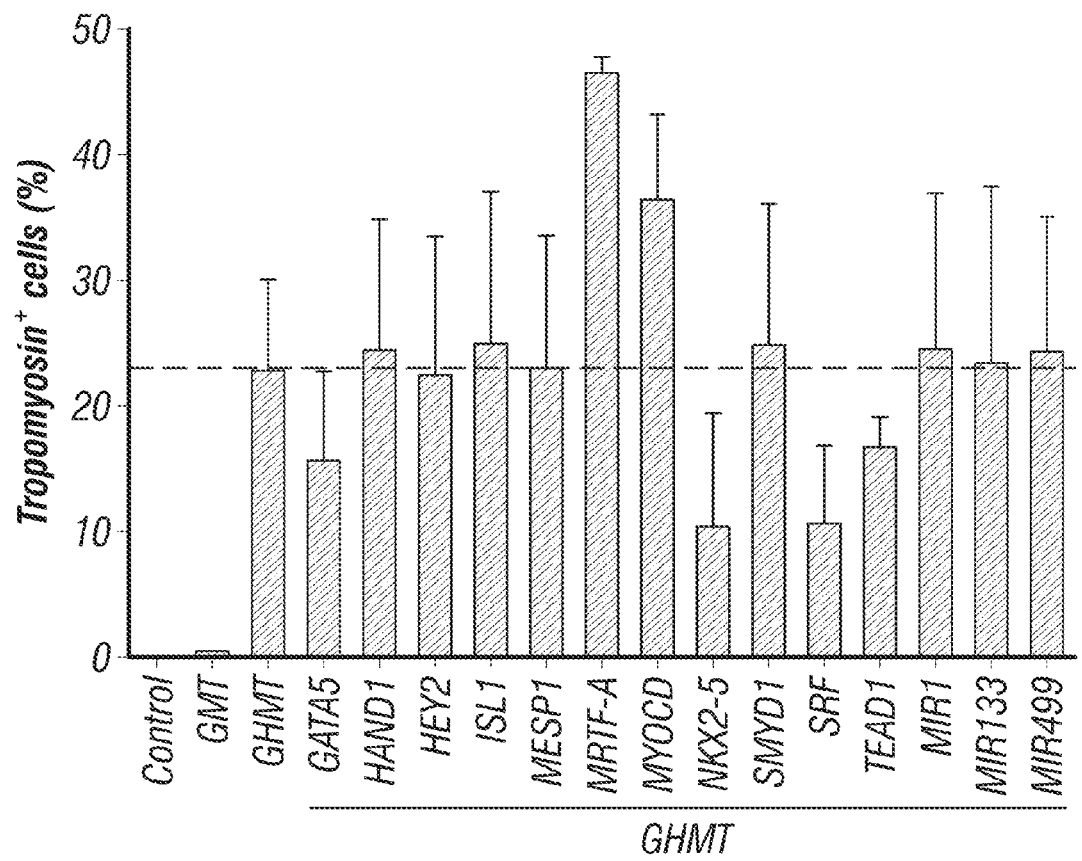

These results demonstrate that GATA4, HAND2, MEF2C, and Tbx5 (GHMT) can reprogram CFs into functional cardiomyocytes in vitro and in vivo. Exogenous GHMT expression in the heart post-MI reduces fibrosis and improves cardiac function. Improvement of cardiac function post-MI by different factor combinations correlated with their ability to convert fibroblasts into iCLMs in vitro (FIG. 27), suggesting that cardiac repair results, at least in part, from reprogramming of non-cardiomyocytes toward a cardiomyocyte fate. However, it is also conceivable that other mechanisms, such as a blockade to the activation of CFs, enhanced survival of cardiomyocytes, facilitated differentiation of activated cardiac progenitors into cardiomyocytes, as described previously (Hsieh et al., 2007; Loffredo et al., 2011), or improved angiogenesis (FIG. 28) contribute to the benefits observed upon expression of these factors in the heart post-MI. The reprogramming strategy presented here provides a potential means of improving cardiac function in vivo, bypassing some of the limitations of cellular transplantation.

Figure 31:
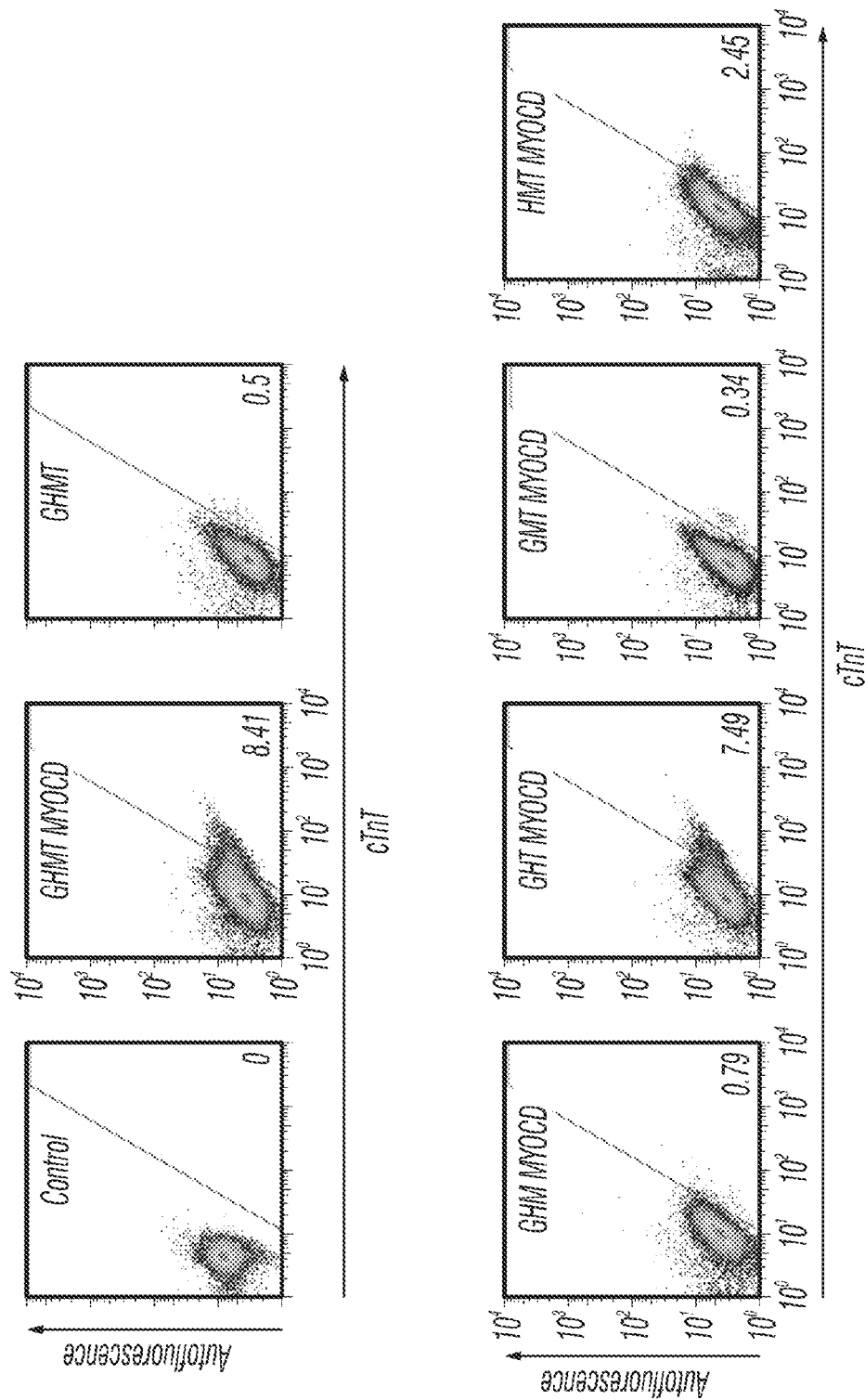
FIG. 31. Flow cytometry analyses to demonstrate the use of five factors (GHMT and MYOCD) to obtain optimal cardiac gene activation in human neonatal foreskin fibroblasts. MYOCD: Myocardin FIG. 32. Flow cytometry analyses to demonstrate the use of five factors (GHMT and MRTF-A) to obtain optimal cardiac gene activation in human neonatal foreskin fibroblasts. MRTF-A: Myocardin related transcription factor A.
Figure 31:
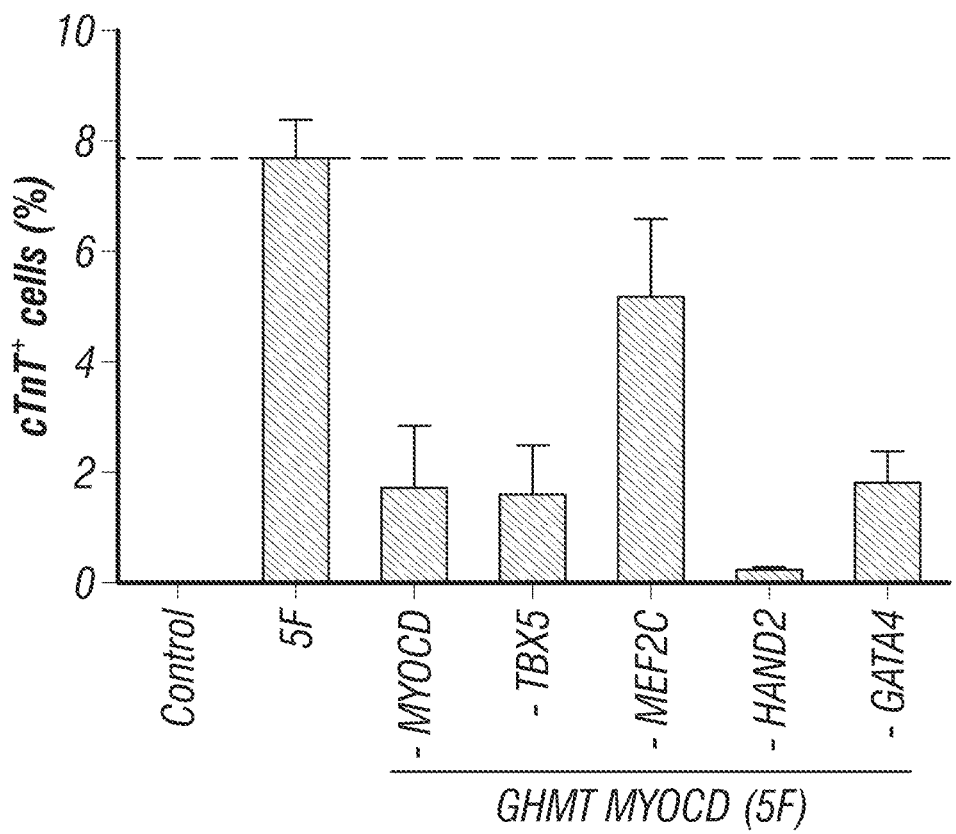
Figure 32:
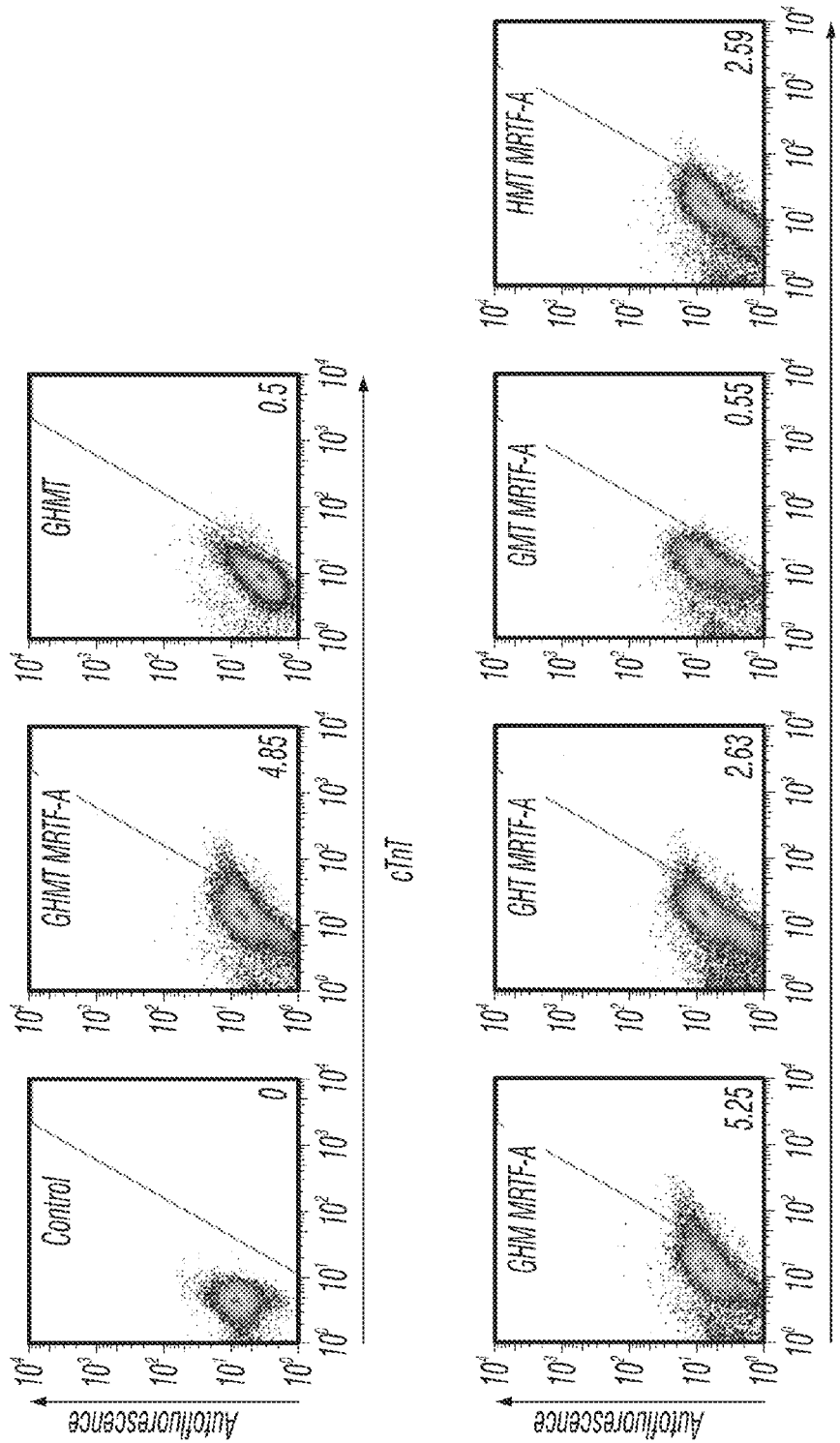
Figure 32:
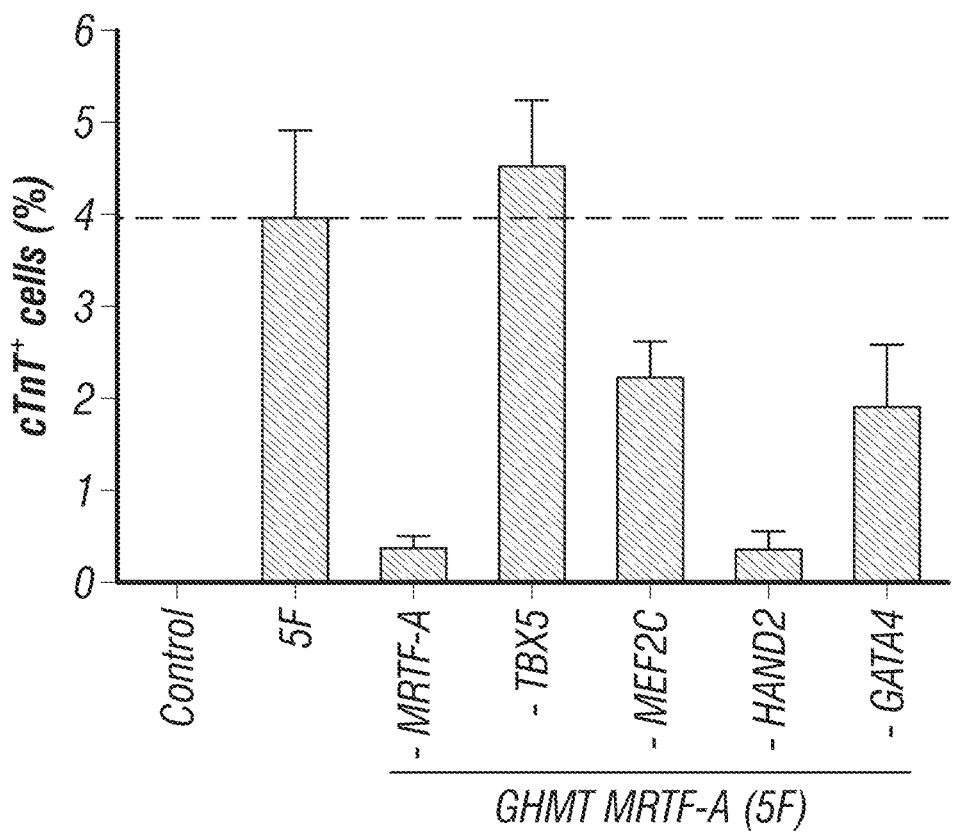
Figure 33:
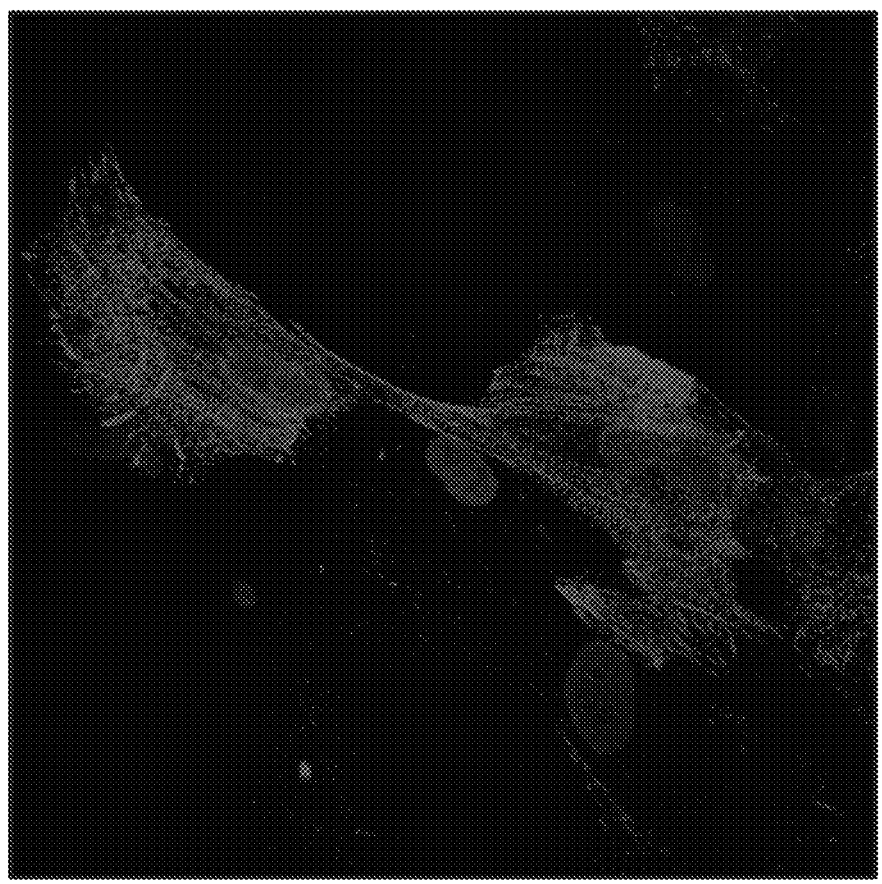
FIG. 33. Immunostaining of cells reprogrammed with GHMT and MYOCD. Cardiac marker, α-actinin, demonstrates sarcomere like structure on human foreskin derived reprogrammed cells with GHMT and MYOCD.
Figure 34:
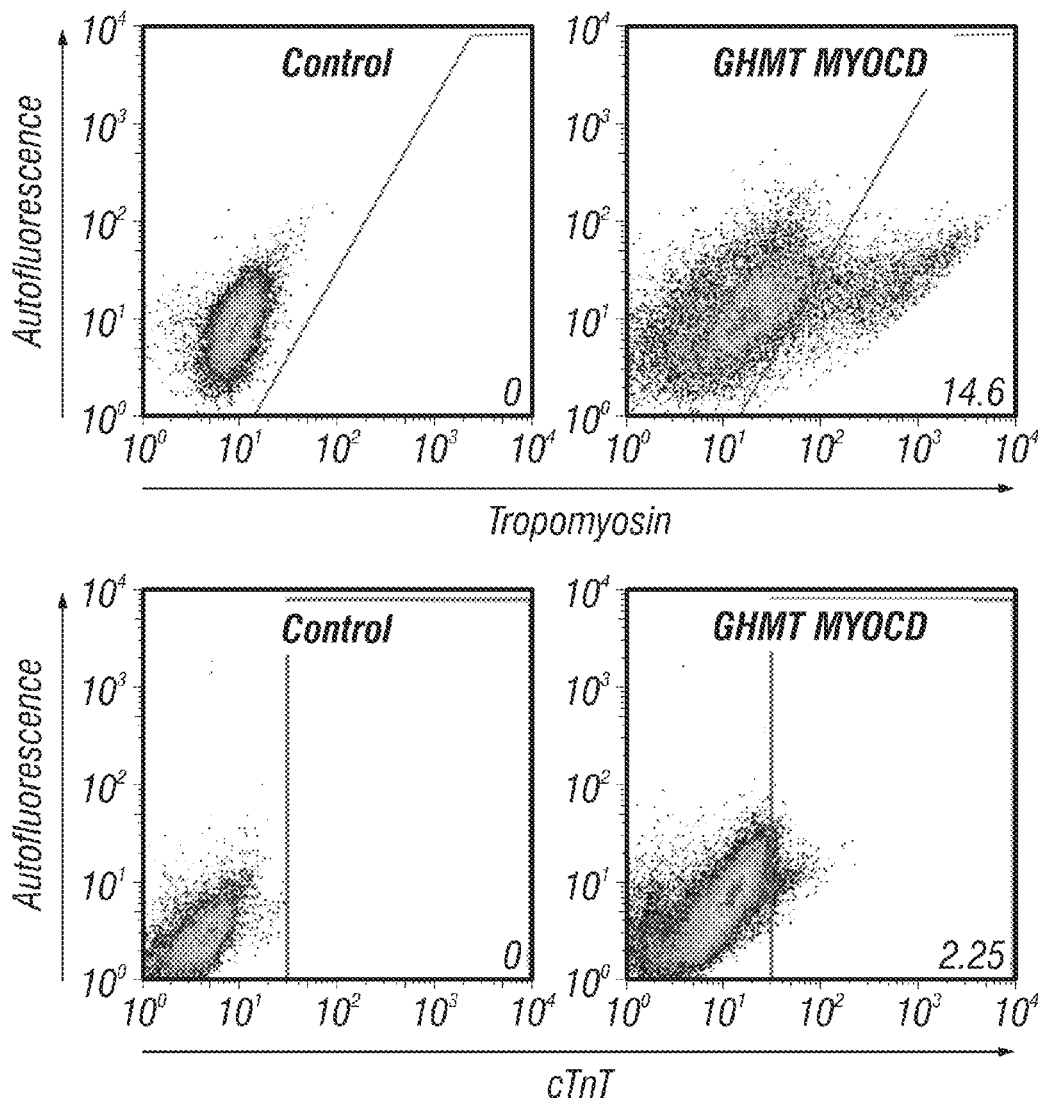
FIG. 34. Flow cytometry showing activatin of cardiac gene expression. Analyses to show the activation of Tropomyoson (Top) and cTnT (Bottom) in adult human cardiac fibroblasts with GHMT and MYOCD.
Figure 35:
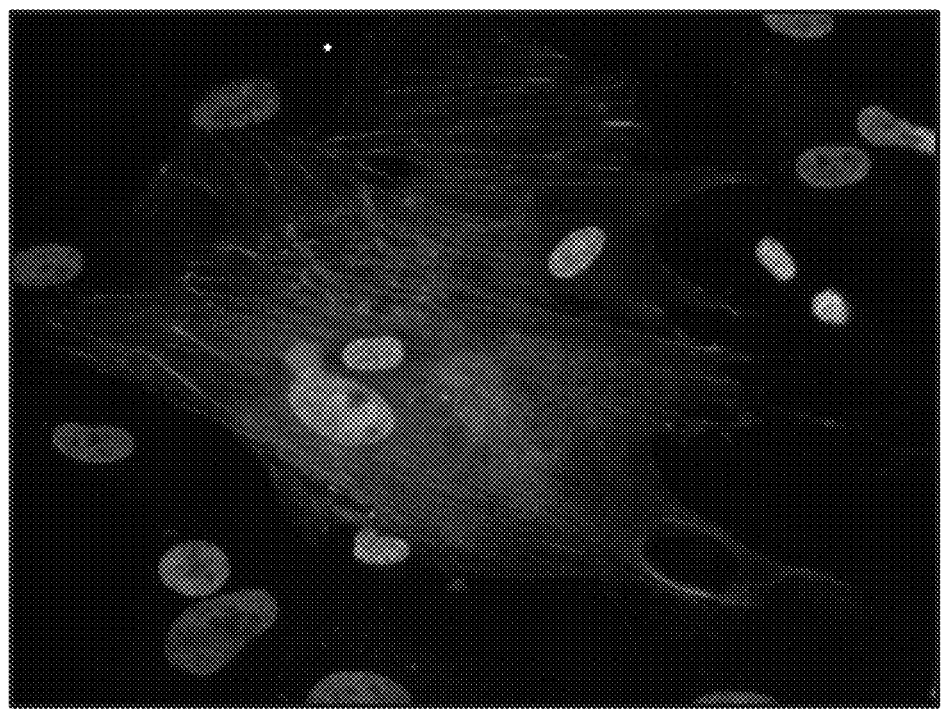
FIG. 35. Immunostaining of cells reprogrammed with GHMT and MYOCD. Cardiac marker, α-actinin, demonstrates sarcomere like structure on adult human cardiac fibroblast derived reprogrammed cells with GHMT and MYOCD.

FIG. 31 shows flow cytometry analyses that demonstrate the use of five factors (GHMT and MYOCD) to obtain optimal cardiac gene activation in human neonatal foreskin fibroblasts. FIG. 32 shows flow cytometry analyses that demonstrate the use of five factors (GHMT and MRTF-A) to obtain optimal cardiac gene activation in human neonatal foreskin fibroblasts. FIG. 33 shows immunostaining of cells reprogrammed with GHMT and MYOCD. The cardiac marker, α-actinin, demonstrates sarcomere like structure on human foreskin derived reprogrammed cells with GHMT and MYOCD. FIG. 34 shows flow cytometry showing activatin of cardiac gene expression. Analyses show the activation of Tropomyoson (Top) and cTnT (Bottom) in adult human cardiac fibroblasts with GHMT and MYOCD. FIG. 35 showsn immunostaining of cells reprogrammed with GHMT and MYOCD. Cardiac marker, α-actinin, demonstrates sarcomere-like structure on adult human cardiac fibroblast derived reprogrammed cells with GHMT and MYOCD.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference.

Acharya et al., *Genesis*, 49:870-877, 2011.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Baichwal and Sugden, In: *Gene Transfer*, Kucherlapati (Ed), NY, Plenum Press, 117-148, 1986.
Banerji et al., *Cell*, 27(2 Pt 1):299-308, 1981.
Banerji et al., *Cell*, 33(3):729-740, 1983.
Barnes et al., *J. Biol. Chem.*, 272(17):11510-7, 1997.
Basson et al., *Nat. Genet.*, 15(1):30-35, 1997.
Benvenisty and Neshif, *Proc. Natl. Acad. Sci. USA*, 83:9551-9555, 1986.
Berkhout et al., *Cell*, 59:273-282, 1989.
Bhaysar et al., *Genomics*, 35(1):11-23, 1996.
Bhowmick et al. *Science*, 303:848-851, 2004.
Blanar et al., *EMBO J.*, 8:1139, 1989.
Bodine and Ley, *EMBO J.*, 6:2997, 1987.
Boshart et al., *Cell*, 41:521, 1985.
Bosher and Labouesse, *Nat. Cell. Biol.*, 2:E31-E36, 2000.
Bosze et al., *EMBO J.*, 5(7):1615-1623, 1986.
Braddock et al., *Cell*, 58:269, 1989.
Brinster et al., *Proc. Natl. Acad Sci. USA*, 82(13):4438-4442, 1985.
Bristow, *Cardiology*, 92:3-6, 1999.
Bulla and Siddiqui, *J. Virol.*, 62:1437, 1986.
Campbell and Villarreal, *Mol. Cell. Biol.*, 8:1993, 1988.
Campbell et al., *J. Mol. Biol.*, 180:1-19, 1984.
Campere and Tilghman, *Genes and Dev.*, 3:537, 1989.
Campo et al., *Nature*, 303:77, 1983.
Capaldi et al., *Biochem. Biophys. Res. Comm.*, 76:425-433, 1977.
Caplen et al., *Gene*, 252(1-2):95-105, 2000.
Celander and Haseltine, *J. Virology*, 61:269, 1987.
Celander et al., *J. Virology*, 62:1314, 1988.
Chandler et al., *Cell*, 33:489, 1983.
Chang et al., *Hepatology*, 14:124A, 1991.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7:2745-2752, 1987.
Choi et al., *Cell*, 53:519, 1988.
Coffey et al., *Cancer Res.*, 61:3591-3594, 2001.
Coffin, In: *Virology*, Fields et al. (Eds.), Raven Press, NY, 1437-1500, 1990.
Cohen et al., *J. Cell. Physiol.*, 5:75, 1987.
Cook et al., *Cell*, 27:487-496, 1981.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.

Dai et al., *J. Biol. Chem.*, 277:24390-24398, 2002.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Durand et al., *Ann. Med.*, 27:311-317, 1995.
Edbrooke et al., *Mol. Cell. Biol.*, 9:1908, 1989.
Edlund et al., *Science*, 230:912-916, 1985.
EP 0273085
Fechheimer et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Fire et al., *Nature*, 391:806-811, 1998.
Fischer, *Med. Res. Rev.*, 27(6):755-796, 2007.
Foecking and Hofstetter, *Gene*, 45(1):101-105, 1986.
Forster and Symons, *Cell*, 49:211-220, 1987.
Fraley et al., *Proc Natl. Acad. Sci. USA*, 76:3348-3352, 1979
Franz et al., *Cardoscience*, 5(4):235-43, 1994.
Friedmann, *Science*, 244:1275-1281, 1989.
Fujita et al., *Cell*, 49:357, 1987.
Furumai et al., *Cancer Res.*, 62:4916-21, 2002.
Gefter, et al., *Somatic Cell Genet.*, 3:231-236, 1977.
Gerlach et al., *Nature (London)*, 328:802-805, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh et al., *Mol. Cell Biol.*, 29:2205-2218, 2009.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Goding, In: *Monoclonal Antibodies: Principles and Practice*, 2d ed., Orlando, Fla., Academic Press, 60-61, 65-66, 71-74, 1986.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Gopal-Srivastava et al., *J. Mol. Cell. Biol.*, 15(12):7081-90, 1995.
Graham and Prevec, In: *Methods in Molecular Biology: Gene Transfer and Expression Protocol*, Murray (Ed.), Humana Press, Clifton, N.J., 7:109-128, 1991.
Graham and van der Eb, *Virology*, 52:456-467, 1973.
Graham et al., *J. Gen. Virol.*, 36:59-72, 1977.
Greene et al., *Immunology Today*, 10:272, 1989
Grishok et al., *Science*, 287:2494-2497, 2000.
Grosschedl and Baltimore, *Cell*, 41:885, 1985.
Grunhaus and Horwitz, *Seminar in Virology*, 3:237-252, 1992.
Grynkiewicz et al., *J. Biol. Chem.*, 260:3440-3450, 1985.
Han et al., *Cancer Research*, 60:6068-6074, 2000.
Harland and Weintraub, *J. Cell Biol.*, 101:1094-1099, 1985.
Harlow and Lane, Antibodies: A Laboratory manual, Cold Spring Harbor Laboratory, 1988.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Nat'l Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Nat'l. Acad. Sci. USA* 90:2812-2816, 1993.
Hirochika et al., *J. Virol.*, 61:2599, 1987.
Hirsch et al., *Mol. Cell. Biol.*, 10:1959, 1990.
Hoffmann et al., *Bioconjugate Chem.*, 12:51-55, 2001.
Holbrook et al., *Virology*, 157:211, 1987.
Horlick and Benfield, *Mol. Cell. Biol.*, 9:2396, 1989.
Horwich et al., *J. Virol.*, 64:642-650, 1990.
Hsieh et al., *Nat. Med.*, 13:970-974, 2007.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Joyce, *Nature*, 338:217-244, 1989.
Kadesch and Berg, *Mol. Cell. Biol.*, 6:2593, 1986.
Kaneda et al., *Science*, 243:375-378, 1989.
Kao et al., *Genes Dev.*, 14:55-66, 2000.
Karin et al., *Mol. Cell. Biol.*, 7:606, 1987.
Karin et al., *Mol. Cell. Biol.*, 7:606, 1987.
Karlsson et al., *EMBO J.*, 5:2377-2385, 1986.
Katinka et al., *Cell*, 20:393, 1980.
Kato et al., *J Biol Chem.*, 266(6):3361-3364, 1991.
Kawamoto et al., *Mol. Cell. Biol.*, 8:267, 1988.
Kelly et al., *J. Cell Biol.*, 129(2):383-96, 1995.
Ketting et al., *Cell*, 99:133-141, 1999.
Kiledjian et al., *Mol. Cell. Biol.*, 8:145, 1988.
Kim and Cook, *Proc. Natl. Acad. Sci. USA*, 84:8788-8792, 1987.
Kim et al., *J. Am. Chem. Soc.*, 121:2056, 1999.
Kimura et al., *Dev. Growth Differ.*, 39(3):257-65, 1997.
Kitamura et al., *Proc. Natl. Acad. Sci. USA*, 92:9146-150, 1995.
Klaassen, In: *The Pharmacological Basis of Therapeutics*, Goodman and Gilman, Eds., Pergamon Press, 8th Ed., 49-61, 1990.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kohler and Milstein, *Eur. J. Immunol.*, 6:511-519, 1976.
Kohler and Milstein, *Nature*, 256:495-497, 1975.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
LaPointe et al., *J. Biol. Chem.*, 263(19):9075-8, 1988.
Larsen et al., *Proc. Natl. Acad. Sci. USA.*, 83:8283, 1986.
Laspia et al., *Cell*, 59:283, 1989.
Latimer et al., *Mol. Cell. Biol.*, 10:760, 1990.
Laugwitz et al., *Nature*, 433:647-653, 2005.
Le Gal La Salle et al., *Science*, 259:988-990, 1993.
Lee et al., *Nature*, 294:228, 1981.
Lee et al., *Nucleic Acids Res.*, 12:4191-206, 1984.
Levinson et al., *Nature*, 295:79, 1982.
Levrero et al., *Gene*, 101:195-202, 1991.

Li et al., *J. Biol. Chem.*, 271:19402-8, 1996.
Lin and Avery, *Nature*, 402:128-129, 1999.
Lin et al., *Mol. Cell. Biol.*, 10:850, 1990.
Loffredo et al., *Cell Stem Cell*, 8:389-98, 2011.
Lu et al., *Proc. Natl. Acad. Sci. USA*, 97:4070-4075, 2000.
Luo et al., *J. Biol. Chem.*, 280:12668-12675, 2005.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Maitra et al., *Dev. Biol.*, 326:368-377, 2009.
Majors and Varmus, *Proc. Natl. Acad. Sci. USA*, 80:5866, 1983.
Mann et al., *Cell*, 33:153-159, 1983.
Markowitz et al., *J. Virol.*, 62:1120-1124, 1988.
McDermott et al., *Mol. Cell. Biol.*, 13(4):2564-2577, 1993.
McNeall et al., *Gene*, 76:81, 1989.
Michel and Westhof, *J. Mol. Biol.*, 216:585-610, 1990.
Miksicek et al., *Cell*, 46:203, 1986.
Miller et al., *Mol. Cell Biol.*, 10:4239-4242, 1990.
Molkentin et al., *Mol. Cell. Biol.*, 16(6):2627-2636, 1996.
Montgomery et al., *Proc. Natl. Acad. Sci. USA*, 95:155-215507, 1998.
Mordacq and Linzer, *Genes and Dev.*, 3:760, 1989.
Moreau et al., *NucL Acids Res.*, 9:6047, 1981.
Moss et al., *J. Gen. Physiol.*, 108(6):473-84, 1996.
Muesing et al., *Cell*, 48:691, 1987.
Ng et al., *Nuc. Acids Res.*, 17:601, 1989.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Olson, *Science*, 313:1922-1927, 2006.
Ondek et al., *EMBO J.*, 6:1017, 1987.
Ornitz et al., *Mol. Cell. Biol.*, 7:3466, 1987.
Palmiter et al., *Cell*, 29:701, 1982.
Palmiter et al., *Nature*, 300:611, 1982.
Paskind et al., *Virology*, 67:242-248, 1975.
Pech et al., *Mol. Cell. Biol.*, 9:396, 1989.
Pelletier and Sonenberg, *Nature*, 334:320-325, 1988.
Perales et al., *Proc. Natl. Acad. Sci. USA*, 91(9):4086-4090, 1994.
Perez-Stable and Constantini, *Mol. Cell. Biol.*, 10:1116, 1990.
Physicians Desk Reference.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porter and Turner, *Pharmacol. Ther.*, 123:255-278, 2009.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotech. Techniques*, 9:169-174, 1995.
Ragot et al., *Nature*, 361:647-650, 1993.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Remington's Pharmaceutical Sciences, 15$^{th}$ ed., 1035-1038 and 1570-1580, Mack Publishing Company, PA, 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A survey of molecular cloning vectors and their uses*, Stoneham: Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rosen et al., *Cell*, 41:813, 1988.
Rosenfeld et al., *Cell*, 68:143-155, 1992.
Rosenfeld et al., *Science*, 252:431-434, 1991.
Roux et al., *Proc. Natl. Acad. Sci. USA*, 86:9079-9083, 1989.
Russell et al., *Biochim. Biophys. Acta*, 1443(3):393-399, 1999.
Russell et al., *Circ Res.*, 108:51-59, 2011.
Saffitz et al., *Am. J. Physiol. Heart Circ. Physiol.*, 278: H1662-H1670, 2000.
Sakai et al., *Genes and Dev.*, 2:1144, 1988.
Sambrook et al., *Molecular Cloning: A Laboratory Manual*, 2nd Ed., Cold Spring Harbor Press, Cold Spring Harbor, N.Y., 2001.
Sarver et al., *Science*, 247:1222-1225, 1990.
Satake et al., *J. Virology*, 62:970, 1988.
Scanlon et al., *Proc. Natl. Acad. Sci. USA*, 88:10591-10595, 1991.
Schaffner et al., *J. Mol. Biol.*, 201:81, 1988.
Schneider et al., *Cardiovasc. Res.*, 75:40-50, 2007.
Searle et al., *Mol. Cell. Biol.*, 5:1480, 1985.
Sharp and Marciniak, *Cell*, 59:229, 1989.
Sharp and Zamore, *Science*, 287:2431-2433, 2000.
Sharp, *Genes Dev.*, 13:139-141, 1999.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Sohal et al., *Circ Res.*, 89:20-25, 2001.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Cohen-Haguenauer and Boiron (Eds.), John Libbey Eurotext, France, 51-61, 1991.
Stratford-Perricaudet et al., *Hum. Gene. Ther.*, 1:241-256, 1990.
Stuart et al., *Nature*, 317:828, 1985.
Subramaniam et al., *J. Biol. Chem.*, 266:24613-24620, 1991.
Sullivan and Peterlin, *Mol. Cell. Biol.*, 7:3315, 1987.
Swartzendruber and Lehman, *J. Cell. Physiology*, 85:179, 1975.
Tabara et al., *Cell*, 99:123-132, 1999.
Takahashi et al., *Antibiotics*, 49:453, 1996.
Takebe et al., *Mol. Cell. Biol.*, 8:466, 1988.
Tandan et al., *Cir. Res.*, 105:51-60, 2009.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Terrett et al., *Nat. Genet.*, 6(4):401-404, 1994.
The Merck Index, 11th Edition.
Thiesen et al., *J. Virology*, 62:614, 1988.
Top et al., *J. Infect. Dis.*, 124:155-160, 1971.
Treisman, *Cell*, 42:889, 1985.
Tronche et al., *Mol. Biol. Med.*, 7:173, 1990.
Trudel and Constantini, *Genes and Dev.* 6:954, 1987.
Tur-Kaspa et al., *Mol. Cell Biol.*, 6:716-718, 1986.
Tyndell et al., *Nuc. Acids. Res.*, 9:6231, 1981.
Vannice and Levinson, *J. Virology*, 62:1305, 1988.

Varmus et al., *Cell*, 25:23-36, 1981.
Vasseur et al., *Proc Natl. Acad. Sci. U.S.A.*, 77:1068, 1980.
Wagner et al., *Proc. Natl. Acad. Sci. USA*, 87(9):3410-3414, 1990.
Wang and Calame, *Cell*, 47:241, 1986.
Weber et al., *Cell*, 36:983, 1984.
Weinberger et al. *Mol. Cell. Biol.*, 8:988, 1984.
White et al., *Genomics*, 27(1):20-26, 1995.
Wincott et al., *Nucleic Acids Res.*, 23(14):2677-2684, 1995.
Winoto and Baltimore, *Cell*, 59:649, 1989.
Wong et al., *Gene*, 10:87-94, 1980.
Workman and Kingston, *Annu. Rev. Biochem.*, 67:545-579, 1998.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu, *Cell Stem Cell*, 3:1-2, 2008.
Yamano et al., *Amer. Soc. Gene Ther.*, 2000.
Yamauchi-Takihara et al., *Proc. Natl. Acad. Sci. USA*, 86(10):3504-3508, 1989.
Yang et al., *Proc. Natl. Acad. Sci. USA*, 87:9568-9572, 1990.
Young et al., In: *Handbook of Applied Therapeutics*, 7.1-7.12 and 9.1-9.10, 1989.
Yutzey et al. *Mol. Cell. Biol.*, 9:1397, 1989.
Zang et al., *J. Biol. Chem.*, 279:54258-54263, 2004.
Zeisberg et al., *Nat. Med.*, 13:952-961, 2007.
Zelenin et al., *FEBS Lett.*, 280:94-96, 1991.
Zhang et al., *Cell*, 110:479-488, 2002.
Zhou et al., *Proc. Natl. Acad. Sci. USA*, 98:10572-10577, 2001.
Ziober and Kramer, *J. Bio. Chem.*, 271(37):22915-22922, 1996.

What is claimed is:

1. A method of reprogramming a cardiac fibroblast comprising contacting said cardiac fibroblast with Tbx5, Mef2C and Hand2.

2. The method of claim 1, wherein contacting comprises delivering Tbx5, Mef2C and Hand2 proteins to said cardiac fibroblast.

3. The method of claim 2, wherein Tbx5, Mef2C and Hand2 comprise a heterologous cell permeability peptide (CPP).

4. The method of claim 2, further comprising contacting said cardiac fibroblast with Gata4.

5. The method of claim 2, further comprising contacting said cardiac fibroblast with myocardin.

6. The method of claim 4, further comprising contacting said cardiac fibroblast with myocardin.

7. The method of claim 1, contacting comprises delivering Tbx5, Mef2C and Hand2 expression cassettes to said cardiac fibroblasts.

8. The method of claim 7, wherein said expression cassettes are comprised in replicable vectors.

9. The method of claim 8, wherein said replicable vectors are viral vectors.

10. The method of claim 9, wherein said viral vectors are adenoviral vectors or retroviral vectors.

11. The method of claim 8, wherein said replicable vectors are non-viral vectors.

12. The method of claim 11, wherein said non-viral vectors are disposed in a lipid delivery vehicle.

13. The method of claim 7, further comprising contacting said cardiac fibroblast with a Gata4 expression cassette.

14. The method of claim 7, further comprising contacting said cardiac fibroblast with a myocardin expression cassette.

15. The method of claim 13, further comprising contacting said cardiac fibroblast with a myocardin expression cassette.

* * * * *

SEQUENCE LISTING

```
<160> NUMBER OF SEQ ID NOS: 52

<210> SEQ ID NO 1
<211> LENGTH: 3921
<212> TYPE: DNA
<213> ORGANISM: Homo sapiens

<400> SEQUENCE: 1
catgccttat gcaagagacc tcagtccccc ggaacaactc gatttccttc caatagaggt      60
ctgaggtgga ctcccacctc ccttcgtgaa gagttccctc ctctcccct  tcctaagaaa     120 gtcgatcttg gctctatttg tgtcttatgt tcatcaccct cattcctccg gagaaagccg     180
ggttggttta tgtctttatt tattcccggg gccaagacgt ccggaacctg tggctgcgca     240
gacccggcac tgataggcga agacggagag aaatttacct cccgccgctg ccccccagcc     300
aaacgtgaca gcgcgcgggc cggttgcgtg actcgtgacg tctccaagtc ctataggtgc     360
agcggctggt gagatagtcg ctatcgcctg gttgcctctt tattttactg gggtatgcct     420
ggtaataaac agtaatattt aatttgtcgg agaccacaaa ccaaccttga gctgggaggt     480
acgtgctctt cttgacagac gttggaagaa gacctggcct aaagaggtct cttttggtgg     540
tccttttcaa agtcttcacc tgagccctgc tctccagcga ggcgcactcc tggcttttgc     600
gctccaaaga agaggtggga tagttggaga gcagaacctt gcgcgggcac agggccctgg     660
gcgcaccatg gccgacgcag acgagggctt tggcctggcg cacacgcctc tggagcctga     720
cgcaaaagac ctgccctgcg attcgaaacc cgagagcgcg ctcggggccc ccagcaagtc     780
cccgtcgtcc ccgcaggccg ccttcaccca gcagggcatg gagggaatca aagtgtttct     840
ccatgaaaga gaactgtggc taaaattcca cgaagtgggc acgaaaatga tcataaccaa     900
ggctggaagg cggatgtttc ccagttacaa agtgaaggtg acgggcctta atcccaaaac     960
gaagtacatt cttctcatgg acattgtacc tgccgacgat cacagataca aattcgcaga    1020
taataaatgg tctgtgacgg gcaaagctga gcccgccatg cctggccgcc tgtacgtgca    1080
cccagactcc cccgccaccg gggcgcattg gatgaggcag ctcgtctcct tccagaaact    1140
caagctcacc aacaaccacc tggacccatt tgggcatatt attctaaatt ccatgcacaa    1200
ataccagcct agattacaca tcgtgaaagc ggatgaaaat aatggatttg gctcaaaaaa    1260
tacagcgttc tgcactcacg tctttcctga gactgcgttt atagcagtga cttcctacca    1320
gaaccacaag atcacgcaat taaagattga gaataatccc tttgccaaag gatttcgggg    1380
cagtgatgac atggagctgc acagaatgtc aagaatgcaa agtaaagaat atcccgtggt    1440
```

-continued

```
ccccaggagc accgtgaggc aaaaagtggc ctccaaccac agtcctttca gcagcgagtc    1500
tcgagctctc tccacctcat ccaatttggg gtcccaatac cagtgtgaga atggtgtttc    1560
cggcccctcc caggacctcc tgcctccacc caacccatac ccactgcccc aggagcatag    1620
ccaaatttac cattgtacca agaggaaaga ggaagaatgt tccaccacag accatcccta    1680
taagaagccc tacatggaga catcacccag tgaagaagat tccttctacc gctctagcta    1740
tccacagcag cagggcctgg gtgcctccta caggacagag tcggcacagc ggcaagcttg    1800
catgtatgcc agctctgcgc cccccagcga gcctgtgccc agcctagagg acatcagctg    1860
caacacgtgg ccaagcatgc cttcctacag cagctgcacc gtcaccaccg tgcagcccat    1920
ggacaggcta ccctaccagc acttctccgc tcacttcacc tcggggcccc tggtccctcg    1980
gctggctggc atggccaacc atggctcccc acagctggga gagggaatgt tccagcacca    2040
gacctccgtg gcccaccagc ctgtggtcag gcagtgtggg cctcagactg gcctgcagtc    2100
ccctggcacc cttcagcccc ctgagttcct ctactctcat ggcgtgccaa ggactctatc    2160
ccctcatcag taccactctg tgcacggagt tggcatggtg ccagagtgga gcgacaatag    2220
ctaaagtgag gcctgcttca caacagacat ttcctagaga aagagagaga gaggagaa    2280 agagagagaa ggagagagac agtagccaag agaaccccac ggacaagatt tttcatttca    2340
cccaatgttc acatctgcac tcaaggtcgc tggatgctga tctaatcagt agcttgaaac    2400
cacaatttta aaaatgtgac tttcttgttt tgtctcaaaa cttaaaaaaa caaacacaaa    2460
aagatgagtc ccacccccca ctaccaccac acccatcaac cagccacatt cacgctactc    2520
cccagatctc ttcccccatt ccttcttttg ggctctagaa agtcttgcct cattgagtgt    2580
ttttccctag tgcgtagttg gagtctgtcc ctgtcttggt gttaatgttg acattgttat    2640
ataataaatg ataatatatt tttttctttc aattttctta atgggaccca gtcccttatt    2700 tgggggagg tctgaggcaa gtatatttca aaatatgtac ttgcgggatt cccttcaagt    2760
aaaccatccc tgaaacctaa attcacgttt ccccttgact aagaaaagca cctacctctg    2820
ccatgtgatg tttctgaaaa gcctctgtat gtccccattt gctttggttt tgtcctgcct    2880
tctccaatat cacgtgctca gttttgcctc tacttaccca tggagtcagg ataacactga    2940
cgctccctgg catcctatct tattcagccc taccatcttg ccagctctgt cttcccagct    3000
gtctgtcgct aaaacgtggc ctatagcttc ccttccggaa agcttgcttt gaaaaactta    3060
aaaagccccc gtttacatgt aggcaggact gtgataacag tgcaagctct gtgttgacaa    3120
gagttgtgga caaaaagcca aaataaatat tcttcctgat taaaaaaatt ttttttgaaa    3180
aaaacaaggc cagccccaac cttccaaacc tccatcacca acaacccaaa ctggatgtca    3240
agcaaaatgc acaattccta cagaagaggc aagacacagt caccaatgat atctcgccaa    3300
agaaaccacg cccacaccaa tgccaacaca aaactgtgtt tactgaaagc cgaaaacagt    3360
attaaaaaaa gtgtgtaagt aaagtgttat ggtagggttc ttcagatgta atatttact    3420 ggtactattt atttataaat aggaattcta attaagtaat aacatgaaat gaaacccagc    3480
ataggagctg gccaagagct tttaattta ttgatactca aaaccaagtt tgtgtttttt    3540 tgttttttt tgtttttttc ctctttcgaa tgtgctttgc tttttttgat taaaaagaat    3600 tttttttc cttttttata aacagaccct aataaagaga acagggtaag atgtgaggct    3660
gagtgtgttt aagtacgtga gagagtgtga gtgtgtttgt aagtgagtgt ccctatgcga    3720
ttatgtctct ttacgttgct aagggggagg ggtgaggatt aagtactcgt gccttatatt    3780
tgtgtgccaa ttaatgccta ataaatacca tgtgcttaaa caagtaaaaa aaaaaaaaa    3840
```

-continued

```
aaaaaaaaaa aaaaaaaaaa aaaaaaaaaa aaaaaaaaaa aaaaaaaaaa aaaaaaaaaa    3900
aaaaaaaaaa aaaaaaaaaa a                                               3921

<210> SEQ ID NO 2
<211> LENGTH: 518
<212> TYPE: PRT
<213> ORGANISM: Homo sapiens

<400> SEQUENCE: 2

Met Ala Asp Ala Asp Glu Gly Phe Gly Leu Ala His Thr Pro Leu Glu
1               5                   10                  15

Pro Asp Ala Lys Asp Leu Pro Cys Asp Ser Lys Pro Glu Ser Ala Leu
            20                  25                  30

Gly Ala Pro Ser Lys Ser Pro Ser Pro Gln Ala Ala Phe Thr Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
    130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
    210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
                245                 250                 255

Val Val Pro Arg Ser Thr Val Arg Gln Lys Val Ala Ser Asn His Ser
            260                 265                 270

Pro Phe Ser Ser Glu Ser Arg Ala Leu Ser Thr Ser Ser Asn Leu Gly
        275                 280                 285

Ser Gln Tyr Gln Cys Glu Asn Gly Val Ser Gly Pro Ser Gln Asp Leu
    290                 295                 300

Leu Pro Pro Pro Asn Pro Tyr Pro Leu Pro Gln Glu His Ser Gln Ile
305                 310                 315                 320

Tyr His Cys Thr Lys Arg Lys Glu Glu Glu Cys Ser Thr Thr Asp His
                325                 330                 335

Pro Tyr Lys Lys Pro Tyr Met Glu Thr Ser Pro Ser Glu Glu Asp Ser
            340                 345                 350
```

```
Phe Tyr Arg Ser Ser Tyr Pro Gln Gln Gly Leu Gly Ala Ser Tyr
            355                 360                 365
Arg Thr Glu Ser Ala Gln Arg Gln Ala Cys Met Tyr Ala Ser Ser Ala
    370                 375                 380
Pro Pro Ser Glu Pro Val Pro Ser Leu Glu Asp Ile Ser Cys Asn Thr
385                 390                 395                 400
Trp Pro Ser Met Pro Ser Tyr Ser Ser Cys Thr Val Thr Thr Val Gln
                405                 410                 415
Pro Met Asp Arg Leu Pro Tyr Gln His Phe Ser Ala His Phe Thr Ser
                420                 425                 430
Gly Pro Leu Val Pro Arg Leu Ala Gly Met Ala Asn His Gly Ser Pro
            435                 440                 445
Gln Leu Gly Glu Gly Met Phe Gln His Gln Thr Ser Val Ala His Gln
    450                 455                 460
Pro Val Val Arg Gln Cys Gly Pro Gln Thr Gly Leu Gln Ser Pro Gly
465                 470                 475                 480
Thr Leu Gln Pro Pro Glu Phe Leu Tyr Ser His Gly Val Pro Arg Thr
                485                 490                 495
Leu Ser Pro His Gln Tyr His Ser Val His Gly Val Gly Met Val Pro
                500                 505                 510
Glu Trp Ser Asp Asn Ser
            515

<210> SEQ ID NO 3
<211> LENGTH: 6449
<212> TYPE: DNA
<213> ORGANISM: Homo sapiens

<400> SEQUENCE: 3
gagctgttct cctttccca ttcgtcttct gtcacttcct tcctggacgc agttttctgg        60
acgagtctgg ttactttaa tccgaccggc cgctgagagc cactttctcc tcctcctcct       120
cctcctcctt ctcttcctcc tccttcttcc tcctcctcct cctcttccga gcggcctcgg      180
cgcgcgcgaa tgcgcggccc cgcgcccccc ccctcgcgcg cgctcccctc gcgcgcgcgc      240
acacacgcac acatcgtctc cagctctctg ctcgctctgc tcgcagtcac agacacttga      300
gcacacgcgt acacccagac atcttcgggc tgctattgga ttgactttga aggttctgtg      360
tgggtcgccg tggctgcatg tttgaatcag gtggagaagc acttcaacgc tggacgaagt      420
aaagattatt gttgttattt tttttttctc tctctctctc tcttaagaaa ggaaaatatc      480
ccaaggacta atctgatcgg gtcttccttc atcaggaacg aatgcaggaa tttgggaact      540
gagctgtgca agtgctgaag aaggagattt gtttggagga acaggaaag agaaagaaaa      600
ggaaggaaaa aatacataat ttcagggacg agagagagaa gaaaacggg gactatgggg       660
agaaaaaaga ttcagattac gaggattatg gatgaacgta acagacaggt gacatttaca      720
aagaggaaat ttgggttgat gaagaaggct tatgagctga gcgtgctgtg tgactgtgag      780
attgcgctga tcatcttcaa cagcaccaac aagctgttcc agtatgccag caccgacatg      840
gacaaagtgc ttctcaagta cacggagtac aacgagccgc atgagagccg acaaactca      900
gacatcgtgg agacgttgag aaagaagggc ttaatggct gtgacagccc agaccccgat      960
gcggacgatt ccgtaggtca cagccctgag tctgaggaca gtacaggaa attaacgaa      1020
gatattgatc taatgatcag caggcaaaga ttgtgtgctg ttccacctcc caacttcgag     1080
atgccagtct ccatcccagt gtccagccac aacagtttgg tgtacagcaa ccctgtcagc     1140
```

```
tcactgggaa accccaacct attgccactg gctcacccTt ctctgcagag gaatagtatg    1200
tctcctggtg taacacatcg acctccaagt gcaggtaaca caggtggtct gatgggtgga    1260
gacctcacgt ctggtgcagg caccagtgca gggaacgggt atggcaatcc ccgaaactca    1320
ccaggtctgc tggtctcacc tggtaacttg aacaagaata tgcaagcaaa atctcctccc    1380
ccaatgaatt taggaatgaa taaccgtaaa ccagatctcc gagttcttat tccaccaggc    1440
agcaagaata cgatgccatc agtgtctgag gatgtcgacc tgcttttgaa tcaaaggata    1500
aataactccc agtcggctca gtcattggct accccagtgg tttccgtagc aactcctact    1560
ttaccaggac aaggaatggg aggatatcca tcagccattt caacaacata tggtaccgag    1620
tactctctga gtagtgcaga cctgtcatct ctgtctgggt ttaacaccgc cagcgctctt    1680
caccttggtt cagtaactgg ctggcaacag caacacctac ataacatgcc accatctgcc    1740
ctcagtcagt tgggagcttg cactagcact catttatctc agagttcaaa tctctccctg    1800
ccttctactc aaagcctcaa catcaagtca gaacctgttt ctcctcctag agaccgtacc    1860
accacccctt cgagataccc acaacacacg cgccacgagg cggggagatc tcctgttgac    1920
agcttgagca gctgtagcag ttcgtacgac gggagcgacc gagaggatca ccggaacgaa    1980
ttccactccc ccattggact caccagacct tcgccggacg aaagggaaag tccctcagtc    2040
aagcgcatgc gactttctga aggatgggca acatgatcag attattactt actagttttt    2100 tttttttttct tgcagtgtgt gtgtgtgcta taccttaatg gggaaggggg gtcgatatgc    2160
attatatgtg ccgtgtgtgg aaaaaaaaaa agtcaggtac tctgttttgt aaaagtactt    2220
ttaaattgcc tcagtgatac agtataaaga taaacagaaa tgctgagata agcttagcac    2280
ttgagttgta caacagaaca cttgtacaaa atagatttta aggctaactt cttttcactg    2340
ttgtgctcct ttgcaaaatg tatgttacaa tagatagtgt catgttgcag gttcaacgtt    2400
atttacatgt aaatagacaa aaggaaacat ttgccaaaag cggcagatct ttactgaaag    2460
agagagcagc tgttatgcaa catatagaaa aatgtataga tgcttggaca gacccggtaa    2520
tgggtggcca ttggtaaatg ttaggaacac accaggtcac ctgacatccc aagaatgctc    2580
acaaacctgc aggcatatca ttggcgtatg gcactcatta aaaaggatca gagaccatta    2640
aaagaggacc atacctatta aaaaaaaatg tggagttgga gggctaacat atttaattaa    2700
ataaataaat aaatctgggt ctgcatctct tattaaataa aaatataaaa atatgtacat    2760
tacattttgc ttattttcat ataaaaggta agacagagtt tgcaaagcat ttgtggcttt    2820
ttgtagttta cttaagccaa aatgtgtttt tttcccttg atagcttcgc taatatttta    2880
aacagtcctg taaaaaacca aaaaggactt tttgtataga aagcactacc ctaagccatg    2940
aagaactcca tgctttgcta accaagataa ctgttttctc tttgtagaag ttttgttttt    3000
gaaatgtgta tttctaatta tataaaatat taagaatctt ttaaaaaaat ctgtgaaatt    3060
aacatgcttg tgtatagctt tctaatatat ataatattat ggtaatagca gaagttttgt    3120
tatcttaata gcgggagggg ggtatatttg tgcagttgca catttgagta actatttcct    3180
ttctgttttc ttttactctg cttacatttt ataagtttaa ggtcagctgt caaaaggata    3240
acctgtgggg ttagaacata tcacattgca acaccctaaa ttgttttaa tacattagca    3300 atctattggg tcaactgaca tccattgtat atactagttt ctttcatgct atttttattt    3360
tgttttttgc attttatca aatgcagggc ccctttctga tctcaccatt tcaccatgca    3420
tcttggaatt cagtaagtgc atatcctaac ttgcccatat tctaaatcat ctggttggtt    3480
ttcagcctag aatttgatac gctttttaga aatatgccca gaatagaaaa gctatgttgg    3540
```

```
ggcacatgtc ctgcaaatat ggccctagaa acaagtgata tggaatttac ttggtgaata    3600
agttataaat tcccacagaa gaaaatgtg aaagactggg tgctagacaa gaaggaagca    3660
ggtaaaggga tagttgcttt gtcatccgtt tttaattatt ttaactgacc cttgacaatc    3720
ttgtcagcaa tataggactg ttgaacaatc ccggtgtgtc aggaccccca aatgtcactt    3780
ctgcataaag catgtatgtc atctattttt tcttcaataa agagatttaa tagccatttc    3840
aagaaatccc ataagaacc tctctatgtc ccttttttta atttaaaaaa aatgactctt    3900
gtctaatatt cgtctataag ggattaattt tcagacccctt taataagtga gtgccataag    3960
aaagtcaata tatattgttt aaaagatatt tcagtctagg aaagattttc cttctcttgg    4020
aatgtgaaga tctgtcgatt catctccaat catatgcatt gacatacaca gcaaagaaga    4080
tataggcagt aatatcaaca ctgctatatc atgtgtagga catttcttat ccatttttc    4140 tcttttactt gcatagttgc tatgtgtttc tcattgtaaa aggctgccgc tgggtggcag    4200
aagccaagag accttattaa ctaggctata ttttcttaa cttgatctga aatccacaat    4260
tagaccacaa tgcacctttg gttgtatcca taaaggatgc tagcctgcct tgtactaatg    4320
ttttatatat taaaaaaaaa aaatctatca accatttcat atatatccca ctactcaagg    4380
tatccatgga acatgaaaga ataacattta tgcagaggaa aaacaaaaac atccctgaaa    4440
atatacacac tcatacacac acacgcacag gggaataaaa taagaaaatc attttcctca    4500
ccatagactt gatcccatcc ttacaaccca tccttctaac ttgatgtgta taaaatatgc    4560
aaacatttca caaatgttct ttgtcatttc aaaatacttt agtatatcaa tatcagtaga    4620
taccagtggg tgggaaaggg tcattacatg aaaaatatgaa gaaatagcca tattagtttt    4680
ttaacctgca atttgcctca gcaacaaaga aaaagtgaat ttttaatgct gaagataaag    4740
taagctaaag taccagcaga agccttggct atttatagca gttctgacaa tagttttata    4800
agaacatgaa gagaacagaa tcacttgaaa atggatgcca gtcatctctt gttcccacta    4860
ctgaattctt ataagtggt ggcaagatag ggaagggata atctgagaat ttttaaaaga    4920
tgatttaatg agaagaagca caattttgat tttgatgagt cactttctgt aaacaatctt    4980
ggtctatctt taccccttata cctttatctgt aatttaccat ttattgtatt tgcaaagcta    5040
gtatggtttt taatcacagt aaatccttg tattccagac tttagggcag agccctgagg    5100
gagtattatt ttcataacc cgtcctagag taacatttta ggcaacattc ttcattgcaa    5160
gtaaaagatc cataagtggc attttacacg gctgcgagta ttgttatatc taatcctatt    5220
ttaaaagatt tttggtaata tgaagcttga atactggtaa cagtgatgca atatacgcaa    5280
gctgcacaac ctgtatattg tatgcattgc tgcgtggagg ctgtttattt caaccttttt    5340
aaaaattgtg ttttttagta aaatggctta tttttcccca aaggtggaat ttagcatttt    5400
gtaatgatga atataaaaat acctgtcatc cccagatcat ttaaaagtta actaaagtga    5460
gaatgaaaaa acaaaattcc aagacacttt ttaaaagaat gtctgccctc acacactttt    5520
atggatttgt ttttcttaca tacccatctt ttaacttaga gatagcattt tttgccctct    5580 ttatttttgtt gtttgtttct ccagagagta aacgctttgt agttctttct ttaaaaaaca    5640 tttttttaa agaagaagaa gccacttgaa ccctcaataa aggctgttgc ctaagcatgg    5700
catacttcat ctgttctcat ttgtgccatc tgccgtgatg tcgtcacttt tatggcgtta    5760
atttcctgcc actacagatc ttttgaagat tgctggaata ctggtgtctg ttagaatgct    5820
tcagactaca gatgtaatta aaggctttc ttaatatgtt ttaaccaaag atgtggagca    5880
atccaagcca catatcttct acatcaaatt tttccatttt ggttatttc ataatctggt    5940
```

```
attgcatttt gccttccctg ttcatacctc aaattgattc atacctcagt ttaattcaga    6000
gaggtcagtt aagtgacgga ttctgttgtg gtttgaatgc agtaccagtg ttctcttcga    6060
gcaaagtaga cctgggtcac tgtaggcata ggacttggat tgcttcagat ggtttgctgt    6120
atcatttttc ttcttttttct tttcctgggg acttgtttcc attaaatgag agtaattaaa    6180
atcgcttgta aatgagggca tacaagcatt tgcaacaaat attcaaatag aggctcacag    6240
cggcataagc tggactttgt cgccactaga tgacaagatg ttataactaa gttaaaccac    6300
atctgtgtat ctcaagggac ttaattcagc tgtctgtagt gaataaaagt gggaaatttt    6360
caaaagtttc tcctgctgga aataaggtat aatttgtatt ttgcagacaa ttcagtaaag    6420
ttactggctt tcttagtgaa aaaaaaaa                                       6449
```

<210> SEQ ID NO 4
<211> LENGTH: 473
<212> TYPE: PRT
<213> ORGANISM: Homo sapiens

<400> SEQUENCE: 4

```
Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
                20                  25                  30

Tyr Glu Leu Ser Val Leu Cys Asp Cys Glu Ile Ala Leu Ile Ile Phe
            35                  40                  45

Asn Ser Thr Asn Lys Leu Phe Gln Tyr Ala Ser Thr Asp Met Asp Lys
        50                  55                  60

Val Leu Leu Lys Tyr Thr Glu Tyr Asn Glu Pro His Glu Ser Arg Thr
65                  70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Pro Asn Phe Glu Met Pro
    130                 135                 140

Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255

Val Leu Ile Pro Pro Gly Ser Lys Asn Thr Met Pro Ser Val Ser Glu
            260                 265                 270

Asp Val Asp Leu Leu Leu Asn Gln Arg Ile Asn Asn Ser Gln Ser Ala
        275                 280                 285
```

Gln Ser Leu Ala Thr Pro Val Val Ser Val Ala Thr Pro Thr Leu Pro
    290                 295                 300

Gly Gln Gly Met Gly Gly Tyr Pro Ser Ala Ile Ser Thr Thr Tyr Gly
305                 310                 315                 320

Thr Glu Tyr Ser Leu Ser Ser Ala Asp Leu Ser Ser Leu Ser Gly Phe
                325                 330                 335

Asn Thr Ala Ser Ala Leu His Leu Gly Ser Val Thr Gly Trp Gln Gln
            340                 345                 350

Gln His Leu His Asn Met Pro Pro Ser Ala Leu Ser Gln Leu Gly Ala
        355                 360                 365

Cys Thr Ser Thr His Leu Ser Gln Ser Ser Asn Leu Ser Leu Pro Ser
370                 375                 380

Thr Gln Ser Leu Asn Ile Lys Ser Glu Pro Val Ser Pro Pro Arg Asp
385                 390                 395                 400

Arg Thr Thr Thr Pro Ser Arg Tyr Pro Gln His Thr Arg His Glu Ala
                405                 410                 415

Gly Arg Ser Pro Val Asp Ser Leu Ser Ser Cys Ser Ser Ser Tyr Asp
            420                 425                 430

Gly Ser Asp Arg Glu Asp His Arg Asn Glu Phe His Ser Pro Ile Gly
        435                 440                 445

Leu Thr Arg Pro Ser Pro Asp Glu Arg Glu Ser Pro Ser Val Lys Arg
450                 455                 460

Met Arg Leu Ser Glu Gly Trp Ala Thr
465                 470

```
<210> SEQ ID NO 5
<211> LENGTH: 3419
<212> TYPE: DNA
<213> ORGANISM: Homo sapiens

<400> SEQUENCE: 5
```

| | | | | | |
|---|---|---|---|---|---|
| ttggaggcgg | ccggcgcagg | ggccgcgaga | ggcttcgtcg | ccgctgcagc | tccgggggct | 60 |
| cccaggggag | cgtgcgcgga | acctccaggc | ccagcaggac | cccggctgcg | gcgaggagga | 120 |
| aggagccagc | ctagcagctt | ctgcgcctgt | ggccgcgggt | gtcctggagg | cctctcggtg | 180 |
| tgacgagtgg | gggacccgaa | ggctcgtgcg | ccacctccag | gcctggacgc | tgccctccgt | 240 |
| cttctgcccc | caataggtgc | gccggacctt | caggccctgg | ggtgaattca | gctgctccta | 300 |
| catcagcttc | cggaaccacc | aaaaattcaa | attgggattt | tccggagtaa | caagagcct | 360 |
| agcccctttt | gctcaatgct | ggatttaata | cgtatatatt | tttaagcgag | ttggtttttt | 420 |
| ccccttttgat | ttttgatctt | cgcgacagtt | cctcccacgc | atattatcgt | tgttgccgtc | 480 |
| gttttctctc | cccgcgtggc | tccttgacct | gcgagggaga | gagaggacac | cgaagccggg | 540 |
| agctcgcagg | gaccatgtat | cagagcttgg | ccatggccgc | caaccacggg | ccgccccccg | 600 |
| gtgcctacga | ggcgggcggc | cccggcgcct | tcatgcacgg | cgcggggcgcc | cgtcctcgc | 660 |
| cagtctacgt | gcccacaccg | cgggtgccct | cctccgtgct | gggcctgtcc | tacctccagg | 720 |
| gcggaggcgc | gggctctgcg | tccggaggcg | cctcgggcgg | cagctccggt | ggggccgcgt | 780 |
| ctggtgcggg | gccgggacc | cagcagggca | gccgggatg | gagccaggcg | ggagccgacg | 840 |
| gagccgctta | caccccgccg | ccggtgtcgc | cgcgcttctc | cttcccgggg | accaccgggt | 900 |
| ccctggcggc | cgccgccgcc | gctgccgcgg | cccgggaagc | tgcggcctac | agcagtggcg | 960 |
| gcggagcggc | gggtgcgggc | ctggcggccc | gcagcagta | cgggcgcgcc | ggcttcgcgg | 1020 |
| gctcctactc | cagcccctac | ccggcttaca | tggccgacgt | gggcgcgtcc | tgggccgcag | 1080 |

```
ccgccgccgc ctccgccggc cccttcgaca gcccggtcct gcacagcctg cccggccggg    1140 ccaaccggc  cgcccgacac cccaatctcg atatgtttga cgacttctca gaaggcagag    1200
agtgtgtcaa ctgtggggct atgtccaccc cgctctggag gcgagatggg acgggtcact    1260
atctgtgcaa cgcctgcggc ctctaccaca agatgaacgg catcaaccgg ccgctcatca    1320
agcctcagcg ccggctgtcc gcctcccgcc gagtgggcct ctcctgtgcc aactgccaga    1380
ccaccaccac cacgctgtgg cgccgcaatg cggaggggcga gcctgtgtgc aatgcctgcg    1440
gcctctacat gaagctccac ggggtcccca ggcctcttgc aatgcggaaa gagggggatcc   1500 aaaccagaaa acggaagccc aagaacctga ataaatctaa gacaccagca gctccttcag    1560
gcagtgagag ccttcctccc gccagcggtg cttccagcaa ctccagcaac gccaccacca    1620
gcagcagcga ggagatgcgt cccatcaaga cggagcctgg cctgtcatct cactacgggc    1680
acagcagctc cgtgtcccag acgttctcag tcagtgcgat gtctggccat gggccctcca    1740
tccaccctgt cctctcggcc ctgaagctct ccccacaagg ctatgcgtct cccgtcagcc    1800
agtctccaca gaccagctcc aagcaggact cttggaacag cctggtcttg gccgacagtc    1860
acggggacat aatcactgcg taatcttccc tcttccctcc tcaaattcct gcacggacct    1920
gggacttgga ggatagcaaa gaaggaggcc ctgggctccc aggggccggc ctcctctgcc    1980
tggtaatgac tccagaacaa caactgggaa gaaacttgaa gtcgacaatc tggttagggg    2040
aagcgggtgt tggattttct cagatgcctt tacacgctga tgggactgga gggagcccac    2100
ccttcagcac gagcacactg catctctcct gtgagttgga gacttctttc ccaagatgtc    2160
cttgtcccct gcgttcccca ctgtggccta ccgtgggt  tttgcattgt gtttctagca    2220
ccgaggatct gagaacaagc ggagggccgg gccctgggac ccctgctcca gcccgaatga    2280
cggcatctgt ttgccatgta cctggatgcg acgggcccct ggggacaggc ccttgcccca    2340
tccatccgct tgaggcatgg caccgccctg catccctaat accaaatctg actccaaaat    2400
tgtggggtgt gacatacaag tgactgaaca cttcctgggg agctacaggg gcacttaacc    2460
caccacagca cagcctcatc aaaatgcagc tggcaacttc tcccccaggt gccttccccc    2520
tgctgccggc ctttgctcct tcacttccaa catctctcaa aataaaaatc cctcttcccg    2580
ctctgagcga ttcagctctg cccgcagctt gtacatgtct ctcccctggc aaaacaagag    2640
ctgggtagtt tagccaaacg gcaccccctc gagttcactg cagacccttc gttcaccgtg    2700
tcacacatag aggggttctg agtaagaaca aaacgttctg ctgctcaagc cagtctggca    2760
agcactcagc ccagcctcga ggtccttctg gggagagtgt aagtggacag agtcctggtc    2820 aggggggcagg agtgtcccaa gggctggccc acctgctgtc tgtctgctcc tcctagccct    2880
tggtcagatg gcagccagag tccctcagga cctgcagcct cgccccggca gaagtctttt    2940
gtccaggagg caaaaagcca gagattctgc aacacgaatt cgaagcaaac aaacacaaca    3000
caacagaatt cctggaaaga agacgactgc taagacacgg cagggggggcc tggagggagc    3060 ctccgactct gagctgctcc gggatctgcc gcgttctcct ctgcacattg ctgtttctgc    3120
ccctgatgct ggagctcaag gagactcctt cctctttctc agcagagctg tagctgactg    3180
tggcattact acgcctcccc acacgcccag acccctcact ccaaaatcct actggctgta    3240
gcagagaata ccttttgaacc aagattctgt tttaatcatc atttacattg ttttcttcca    3300
aaggccccct cgtatacccct ccctaaccca caaacctgtt aacattgtct taaggtgaaa    3360
tggctggaaa atcagtattt aactaataaa tttatctgta ttcctcttaa aaaaaaaa     3419
```

```
<210> SEQ ID NO 6
<211> LENGTH: 442
<212> TYPE: PRT
<213> ORGANISM: Homo sapiens

<400> SEQUENCE: 6

Met Tyr Gln Ser Leu Ala Met Ala Ala Asn His Gly Pro Pro Gly
1               5                   10                  15

Ala Tyr Glu Ala Gly Gly Pro Gly Ala Phe Met His Gly Ala Gly Ala
            20                  25                  30

Ala Ser Ser Pro Val Tyr Val Pro Thr Pro Arg Val Pro Ser Ser Val
            35                  40                  45

Leu Gly Leu Ser Tyr Leu Gln Gly Gly Ala Gly Ser Ala Ser Gly
50                  55                  60

Gly Ala Ser Gly Gly Ser Ser Gly Gly Ala Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Ala Arg Glu
            115                 120                 125

Ala Ala Ala Tyr Ser Ser Gly Gly Gly Ala Ala Gly Ala Gly Leu Ala
            130                 135                 140

Gly Arg Glu Gln Tyr Gly Arg Ala Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Asp Met Phe
            195                 200                 205

Asp Asp Phe Ser Glu Gly Arg Glu Cys Val Asn Cys Gly Ala Met Ser
            210                 215                 220

Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
                245                 250                 255

Pro Gln Arg Arg Leu Ser Ala Ser Arg Arg Val Gly Leu Ser Cys Ala
            260                 265                 270

Asn Cys Gln Thr Thr Thr Thr Thr Leu Trp Arg Arg Asn Ala Glu Gly
            275                 280                 285

Glu Pro Val Cys Asn Ala Cys Gly Leu Tyr Met Lys Leu His Gly Val
            290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
                325                 330                 335

Ser Glu Ser Leu Pro Pro Ala Ser Gly Ala Ser Ser Asn Ser Ser Asn
            340                 345                 350

Ala Thr Thr Ser Ser Ser Glu Glu Met Arg Pro Ile Lys Thr Glu Pro
            355                 360                 365

Gly Leu Ser Ser His Tyr Gly His Ser Ser Ser Val Ser Gln Thr Phe
370                 375                 380
```

```
Ser Val Ser Ala Met Ser Gly His Gly Pro Ser Ile His Pro Val Leu
385                 390                 395                 400

Ser Ala Leu Lys Leu Ser Pro Gln Gly Tyr Ala Ser Pro Val Ser Gln
            405                 410                 415

Ser Pro Gln Thr Ser Ser Lys Gln Asp Ser Trp Asn Ser Leu Val Leu
                420                 425                 430

Ala Asp Ser His Gly Asp Ile Ile Thr Ala
            435                 440

<210> SEQ ID NO 7
<211> LENGTH: 2368
<212> TYPE: DNA
<213> ORGANISM: Homo sapiens

<400> SEQUENCE: 7
ctgtacatgg agatcttgct gggaaaatcc gcttgctccc ctcacgtcgt ccagcccagg      60
agaaccaccg ccgtcacccc ggagcttcct cggccaccgc gcagagccct ccgagagccc    120
gagccgcggt cttcgagctc caaggctcat tcagggcccc agatccttgc cccgaaagga    180
gaggatctga gaaatggat gcactgagac ctctctgaaa accctccgag agagcgcgag    240
aggagcgagg acacgttact cgcagctaaa atcacattta aggaccaaaa caacaacaac    300
caaaaatttc attaaaacaa taagcgccca agaacccaga tcgggctggt gggggaggg    360 gaagaggcgg gaagggggagg gtcgcacgga ggtagctttg cagtgagcag tcgaccccgc    420 cgcccccgg cacagctgga ccggctcctc cagccgcggc tcagactcgc cctggattc      480 cgggttagct tcggtgccag gaccgcgggcc cgggcttgga ttcccgagac tccgcgtacc    540
agcctcgcgg gagccccggc acctttgtat gagcacgaga ggattctgcc tccgcgcagc    600
agcccgggaa gcaggagccg aagcgcgggc cgtggagcaa gcgggaacc ggaggcggcg    660 gcggcggcgg ccaggggcgc acggtgccag gaccagctcg ccgcgcccca tggggagccg    720
gcggccgcag cgctgctgag gcgggccggg ctggccaggc gggggacgg ggcccgggct    780 gcagcagccc cctctgcggc tgccgggcgg gcccgggcgc ccgggggctg ggggtgggg    840 ggtggggag gacgccgagc gctgaggcag ggccccgggc cgaggcgcg gcggggctgc    900 gcgcacgctg gggcgcgtgg aggggcgcgg agggcgaaat gagtctggta ggtggttttc    960
cccaccaccc ggtggtgcac cacgagggct acccgttttgc cgccgccgcc gccgcagctg   1020
ccgccgccgc cgccagccgc tgcagccatg aggagaaccc ctacttccat ggctggctca    1080
tcggccaccc cgagatgtcg cccccccgact acagcatggc cctgtcctac agccccgagt   1140
atgccagcgg cgccgccggc ctggaccact cccattacgg gggggtgccg ccgggcgccg    1200 ggccccccggg cctggggggg ccgcgcccgg tgaagcgccg aggcaccgcc aaccgcaagg   1260
agcggcgcag gactcagagc atcaacagcg ccttcgccga actgcgcgag tgcatcccca    1320
acgtaccccg cgacaccaaa ctctccaaaa tcaagaccct gcgcctggcc accagctaca    1380
tcgcctacct catggacctg ctggccaagg acgaccagaa tggcgaggcg gaggccttca    1440
aggcagagat caagaagacc gacgtgaaag aggagaagag gaagaaggag ctgaacgaaa    1500
tcttgaaaag cacagtgagc agcaacgaca agaaaaccaa aggccggacg ggctggccgc    1560
agcacgtctg ggccctggag ctcaagcagt gaggaggagg agaaggagga ggaggagagc   1620
gcgagtgagc aggggccaag gcgccagatg cagacccagg actccggaaa agccgtccgc    1680
gctccgctct gaggactcct tgcatttgga atcatccggt ttatttatgt gcaatttcct    1740 tccctctct ttgacccct ttgaggcatc tgctccccgt ctcccctcc aaaaaaaaag     1800
```

-continued

```
tggatatttg aagaaaagca ttccatattt taatacgaag aggacactcc cgtgtggtaa    1860
gggatcccgt cgtctcatag attctgtgtg cgtgaatgtt ccctcttggc tgtgtagaca    1920
ccagcgttgc cccccgccaa cctactcaac cccttccaga taaagacagt gggcactagt    1980
gcgtttgtga agtgtatctt taatacttgg cctttggata taaatattcc tgggtattat    2040
aaagttttat ttcaaagcag aaaacagggc cgctaacatt tccgttgggg tcggtatcta    2100
gtgctatcca ttcatctgtg gtcgttccct ctttgaagat gtttccaaca gccacttgtt    2160
ttgtgcactt ccgtcctcta aaactaaatg gaatttaatt aatattgaag gtgtaaacgt    2220
tgtaagtatt caataaacca ctgtgttttt ttttacaaa aaccttaatc ttttaatggc     2280
tgatacctca aaagagtttt gaaaacaaag ctgttatact tgttttcgta atatttaaaa    2340
tattcagaag taaactaaat tatcatga                                       2368
```

<210> SEQ ID NO 8
<211> LENGTH: 217
<212> TYPE: PRT
<213> ORGANISM: Homo sapiens

<400> SEQUENCE: 8

Met Ser Leu Val Gly Gly Phe Pro His His Pro Val Val His Glu
1               5                   10                  15

Gly Tyr Pro Phe Ala Ala Ala Ala Ala Ala Ala Ala Ala Ala Ala
                20                  25                  30

Ser Arg Cys Ser His Glu Glu Asn Pro Tyr Phe His Gly Trp Leu Ile
            35                  40                  45

Gly His Pro Glu Met Ser Pro Pro Asp Tyr Ser Met Ala Leu Ser Tyr
        50                  55                  60

Ser Pro Glu Tyr Ala Ser Gly Ala Ala Gly Leu Asp His Ser His Tyr
65                  70                  75                  80

Gly Gly Val Pro Pro Gly Ala Gly Pro Pro Gly Leu Gly Gly Pro Arg
                85                  90                  95

Pro Val Lys Arg Arg Gly Thr Ala Asn Arg Lys Glu Arg Arg Arg Thr
            100                 105                 110

Gln Ser Ile Asn Ser Ala Phe Ala Glu Leu Arg Glu Cys Ile Pro Asn
        115                 120                 125

Val Pro Ala Asp Thr Lys Leu Ser Lys Ile Lys Thr Leu Arg Leu Ala
130                 135                 140

Thr Ser Tyr Ile Ala Tyr Leu Met Asp Leu Leu Ala Lys Asp Asp Gln
145                 150                 155                 160

Asn Gly Glu Ala Glu Ala Phe Lys Ala Glu Ile Lys Lys Thr Asp Val
                165                 170                 175

Lys Glu Glu Lys Arg Lys Lys Glu Leu Asn Glu Ile Leu Lys Ser Thr
            180                 185                 190

Val Ser Ser Asn Asp Lys Lys Thr Lys Gly Arg Thr Gly Trp Pro Gln
        195                 200                 205

His Val Trp Ala Leu Glu Leu Lys Gln
    210                 215

<210> SEQ ID NO 9
<211> LENGTH: 23
<212> TYPE: PRT
<213> ORGANISM: Artificial Sequence
<220> FEATURE:
<223> OTHER INFORMATION: Synthetic peptide

```
<400> SEQUENCE: 9

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Arg Arg Met Lys Trp Lys Lys
1               5

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Arg Arg Trp Arg Arg Trp Trp Arg Arg Trp Trp Arg Arg Trp Arg Arg
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Arg Gly Gly Arg Leu Ser Tyr Ser Arg Arg Phe Ser Thr Ser Thr
1               5                   10                  15

Gly Arg

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Tyr Gly Arg Lys Lys Arg Arg Gln Arg Arg
1               5                   10
```

```
<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Arg Lys Lys Arg Arg Gln Arg Arg Arg
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Tyr Ala Arg Ala Ala Ala Arg Gln Ala Arg Ala
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Arg Arg Arg Arg Arg Arg Arg Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Lys Lys Lys Lys Lys Lys Lys Lys
1               5

<210> SEQ ID NO 19
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 19

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 20

Leu Leu Ile Leu Leu Arg Arg Arg Ile Arg Lys Gln Ala Asn Ala His
1               5                   10                  15

Ser Lys

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide

<400> SEQUENCE: 21

Ser Arg Arg His His Cys Arg Ser Lys Ala Lys Arg Ser Arg His His
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Asn Arg Ala Arg Arg Asn Arg Arg Arg Val Arg
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Arg Gln Leu Arg Ile Ala Gly Arg Arg Leu Arg Gly Arg Ser Arg
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Lys Leu Ile Lys Gly Arg Thr Pro Ile Lys Phe Gly Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Arg Arg Ile Pro Asn Arg Arg Pro Arg Arg
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 26

Lys Leu Ala Leu Lys Leu Ala Leu Lys Ala Leu Lys Ala Ala Leu Lys
1               5                   10                  15

Leu Ala

<210> SEQ ID NO 27
<211> LENGTH: 14
<212> TYPE: PRT
<213> ORGANISM: Artificial Sequence
<220> FEATURE:
<223> OTHER INFORMATION: Synthetic peptide

<400> SEQUENCE: 27

Lys Leu Ala Lys Leu Ala Lys Lys Leu Ala Lys Leu Ala Lys
1               5                   10

<210> SEQ ID NO 28
<211> LENGTH: 27
<212> TYPE: PRT
<213> ORGANISM: Artificial Sequence
<220> FEATURE:
<223> OTHER INFORMATION: Synthetic peptide

<400> SEQUENCE: 28

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 29
<211> LENGTH: 21
<212> TYPE: PRT
<213> ORGANISM: Artificial Sequence
<220> FEATURE:
<223> OTHER INFORMATION: Synthetic peptide

<400> SEQUENCE: 29

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Leu Lys Lys Leu Leu Lys Lys Leu Leu Lys Lys Leu Leu Lys Lys Leu
1               5                   10                  15

Leu Lys Lys Leu
            20

<210> SEQ ID NO 31
<211> LENGTH: 34
<212> TYPE: PRT
<213> ORGANISM: Artificial Sequence
<220> FEATURE:
<223> OTHER INFORMATION: Synthetic peptide
```

```
<400> SEQUENCE: 31

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 32
<211> LENGTH: 23
<212> TYPE: PRT
<213> ORGANISM: Artificial Sequence
<220> FEATURE:
<223> OTHER INFORMATION: Synthetic peptide

<400> SEQUENCE: 32

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 33
<211> LENGTH: 26
<212> TYPE: PRT
<213> ORGANISM: Artificial Sequence
<220> FEATURE:
<223> OTHER INFORMATION: Synthetic peptide

<400> SEQUENCE: 33

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 34
<211> LENGTH: 28
<212> TYPE: PRT
<213> ORGANISM: Artificial Sequence
<220> FEATURE:
<223> OTHER INFORMATION: Synthetic peptide

<400> SEQUENCE: 34

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 35
<211> LENGTH: 24
<212> TYPE: PRT
<213> ORGANISM: Artificial Sequence
<220> FEATURE:
<223> OTHER INFORMATION: Synthetic peptide

<400> SEQUENCE: 35

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 36
<211> LENGTH: 26
<212> TYPE: PRT
<213> ORGANISM: Artificial Sequence
```

<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 36

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 37
<211> LENGTH: 14
<212> TYPE: PRT
<213> ORGANISM: Artificial Sequence
<220> FEATURE:
<223> OTHER INFORMATION: Synthetic peptide

<400> SEQUENCE: 37

Pro Pro Pro Pro Pro Pro Pro Pro Pro Pro Pro Pro
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Synthetic peptide

<400> SEQUENCE: 38

Val Arg Leu Pro Pro Pro Val Arg Leu Pro Pro Pro Val Arg Leu Pro
1               5                   10                  15

Pro Pro

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Pro Arg Pro Leu Pro Pro Pro Arg Pro Gly
1               5                   10

<210> SEQ ID NO 40
<211> LENGTH: 30
<212> TYPE: PRT
<213> ORGANISM: Artificial Sequence
<220> FEATURE:
<223> OTHER INFORMATION: Synthetic peptide

<400> SEQUENCE: 40

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 41
<211> LENGTH: 21
<212> TYPE: PRT
<213> ORGANISM: Artificial Sequence
<220> FEATURE:
<223> OTHER INFORMATION: Synthetic peptide

<400> SEQUENCE: 41

Thr Arg Ser Ser Arg Ala Gly Leu Gln Phe Pro Val Gly Arg Val His
1               5                   10                  15

Arg Leu Leu Arg Lys
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic peptide

<400> SEQUENCE: 42

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 43
<211> LENGTH: 37
<212> TYPE: PRT
<213> ORGANISM: Artificial Sequence
<220> FEATURE:
<223> OTHER INFORMATION: Synthetic peptide

<400> SEQUENCE: 43

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 44
<211> LENGTH: 28
<212> TYPE: PRT
<213> ORGANISM: Artificial Sequence
<220> FEATURE:
<223> OTHER INFORMATION: Synthetic peptide

<400> SEQUENCE: 44

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 45
<211> LENGTH: 26
<212> TYPE: PRT
<213> ORGANISM: Artificial Sequence
<220> FEATURE:
<223> OTHER INFORMATION: Synthetic peptide

<400> SEQUENCE: 45

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 46
<211> LENGTH: 14
<212> TYPE: PRT
<213> ORGANISM: Artificial Sequence
<220> FEATURE:
<223> OTHER INFORMATION: Synthetic peptide

<400> SEQUENCE: 46

```
Ile Asn Leu Lys Ala Leu Ala Ala Leu Ala Lys Lys Ile Leu
1               5                   10
```

<210> SEQ ID NO 47
<211> LENGTH: 33
<212> TYPE: PRT
<213> ORGANISM: Artificial Sequence
<220> FEATURE:
<223> OTHER INFORMATION: Synthetic peptide

<400> SEQUENCE: 47

```
Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu
```

<210> SEQ ID NO 48
<211> LENGTH: 15
<212> TYPE: PRT
<213> ORGANISM: Artificial Sequence
<220> FEATURE:
<223> OTHER INFORMATION: Synthetic peptide

<400> SEQUENCE: 48

```
Leu Ala Lys Trp Ala Leu Lys Gln Gly Phe Ala Lys Leu Lys Ser
1               5                   10                  15
```

<210> SEQ ID NO 49
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 49

```
Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25
```

<210> SEQ ID NO 50
<211> LENGTH: 41
<212> TYPE: PRT
<213> ORGANISM: Artificial Sequence
<220> FEATURE:
<223> OTHER INFORMATION: Synthetic peptide

```
<400> SEQUENCE: 50

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 51
<211> LENGTH: 18
<212> TYPE: PRT
<213> ORGANISM: Artificial Sequence
<220> FEATURE:
<223> OTHER INFORMATION: Synthetic peptide

<400> SEQUENCE: 51

Pro Ala Trp Arg Lys Ala Phe Arg Trp Ala Trp Arg Met Leu Lys Lys
1               5                   10                  15

Ala Ala

<210> SEQ ID NO 52
<211> LENGTH: 18
<212> TYPE: PRT
<213> ORGANISM: Artificial Sequence
<220> FEATURE:
<223> OTHER INFORMATION: Synthetic peptide

<400> SEQUENCE: 52

Lys Leu Lys Leu Lys Leu Lys Leu Lys Leu Lys Leu Lys Leu Lys Leu
1               5                   10                  15

Lys Leu
```